United States Patent
Massimini et al.

(10) Patent No.: US 12,171,829 B2
(45) Date of Patent: Dec. 24, 2024

(54) ABITUZUMAB FOR THE TREATMENT OF COLORECTAL CANCER

(71) Applicant: Merck Patent GmbH, Darmstadt (DE)

(72) Inventors: Giorgio Massimini, Darmstadt (DE); Ilhan Celik, Zwingenberg (DE); Josef Straub, Seeheim-Jugenheim (DE); Rolf Bruns, Darmstadt (DE); Rita Laeufle, San Diego, CA (US)

(73) Assignee: Merck Patent GmbH, Darmstadt (DE)

( * ) Notice: Subject to any disclaimer, the term of this patent is extended or adjusted under 35 U.S.C. 154(b) by 48 days.

(21) Appl. No.: 16/657,828

(22) Filed: Oct. 18, 2019

(65) Prior Publication Data

US 2020/0121788 A1 Apr. 23, 2020

Related U.S. Application Data

(60) Provisional application No. 62/748,114, filed on Oct. 19, 2018.

(51) Int. Cl.

| | |
|---|---|
| A61K 39/395 | (2006.01) |
| A61K 31/44 | (2006.01) |
| A61K 31/4745 | (2006.01) |
| A61K 31/513 | (2006.01) |
| A61K 31/519 | (2006.01) |
| A61K 31/7072 | (2006.01) |
| A61K 33/243 | (2019.01) |
| A61K 38/17 | (2006.01) |
| A61K 39/00 | (2006.01) |
| A61P 35/00 | (2006.01) |
| C07K 16/22 | (2006.01) |
| C07K 16/28 | (2006.01) |

(52) U.S. Cl.
CPC ........ *A61K 39/39558* (2013.01); *A61K 31/44* (2013.01); *A61K 31/4745* (2013.01); *A61K 31/513* (2013.01); *A61K 31/519* (2013.01); *A61K 31/7072* (2013.01); *A61K 33/243* (2019.01); *A61K 38/179* (2013.01); *A61P 35/00* (2018.01); *C07K 16/22* (2013.01); *C07K 16/2848* (2013.01); *C07K 16/2863* (2013.01); *A61K 2039/505* (2013.01); *A61K 2039/507* (2013.01); *A61K 2039/545* (2013.01); *C07K 2317/76* (2013.01)

(58) Field of Classification Search
CPC ............ A61K 39/39558; A61K 33/243; A61K 31/44; C07K 16/22
See application file for complete search history.

(56) References Cited

U.S. PATENT DOCUMENTS

| 5,985,278 A | 11/1999 | Mitjans et al. |
|---|---|---|
| 2005/0220786 A1 | 10/2005 | Mahler et al. |
| 2007/0172475 A1 | 7/2007 | Matheus et al. |
| 2008/0166346 A1 | 7/2008 | Mahler et al. |
| 2012/0076784 A1 | 3/2012 | Matheus et al. |
| 2017/0298134 A1 | 10/2017 | Straub et al. |

FOREIGN PATENT DOCUMENTS

| EP | 0 719 859 A1 | 7/1996 |
|---|---|---|
| EP | 0 719 859 B1 | 7/2003 |
| EP | 0 531 472 B1 | 8/2003 |
| JP | 2017-535516 | 11/2017 |
| WO | 03/053465 A2 | 7/2003 |
| WO | 03/053465 A3 | 12/2003 |
| WO | 2005/077414 A1 | 8/2005 |
| WO | 2009/010290 A2 | 1/2009 |
| WO | 2009/010290 A3 | 4/2009 |
| WO | 2016041614 | 3/2016 |

OTHER PUBLICATIONS

Wania et al., Comparative Effectiveness and Safety of Monoclonal Antibodies (Bevacizumab, Cetuximab, and Panitumumab) in Combination with Chemotherapy for Metastatic Colorectal Cancer: A Systematic Review and Meta-Analysis, Biodrugs (2018) 32: 585-606 (Year: 2018).*

Laeufle R., A retrospective analysis of the randomized phase I/II Poseidon study, Annals of Oncology, 29 (supple_8):viii164. Publication Date: Oct. 1, 2018 (Year: 2018).*

Pasetto et al., FOLFOX Versus FOLFIRI: A Comparison of Regimens in the Treatment of Colorectal Cancer Metastases, Anticancer Research 25:563-576, Publication Date: Feb. 2005 (Year: 2005).*

Elez et al., Abituzumab combined with cetuximab plus irinotecan versus cetuximab plus irinotecan alone for patients with KRAS wild-type metastatic colorectal cancer, Annals of Oncology, 26:132-140, including Supplement, Publication Date: Oct. 15, 2014 (Year: 2014).*

(Continued)

*Primary Examiner* — Peter J Reddig
*Assistant Examiner* — Cheng Lu
(74) *Attorney, Agent, or Firm* — Grüneberg and Myers PLLC

(57) ABSTRACT

Methods of treatment of colorectal cancer can include the administration of the anti-alpha-v integrin (receptor) antibody Abituzumab. Preferably, the methods of treating colorectal cancer can include treating Stage II-IV colorectal cancer, metastatic colorectal cancer, left-sided colorectal cancer and/or left-sided metastatic colorectal cancer, involving the administration of said Abituzumab to patients in need thereof. Abituzumab is also useful for the manufacture of a medicament for treating colorectal cancer, preferably colorectal cancer as defined herein. Abituzumab is further useful for the manufacture of a medicament for treating colorectal cancer in combination with suitable targeted therapy concepts, such as growth factor or growth factor receptor targeting monoclonal antibodies, and/or chemotherapy.

39 Claims, 11 Drawing Sheets

Specification includes a Sequence Listing.

(56) References Cited

OTHER PUBLICATIONS

Erbitux Information (Highlights of Prescribing Information, Reference ID: 4422941, Publication Date: Apr. 2019) (Year: 2019).*
Agrez et al., British Journal of Cancer; 1996, 73:887-892.
Amado et al., Journal of Clinical Oncology; 2008, 26(10):1626-1634.
Arnaout et al., Curr Opin Cell Biol; 2007, 19(5):495-507.
Arnold et al., Annals of Oncology; 2017, 28:1713-1729.
Bates et al., The Journal of Clinical Investigation; 2005, 115(2):339-347.
Bates, Cell Cycle; 2005, 4(10):1350-1352.
Bever et al., Journal of the National Comprehensive Cancer Network, 2017, 15(3):401-410.
Bisanz et al., Molecular Therapy, 2005; 12(4):634-643.
Ciombor et al., Pharmacogenomics and Personalized Medicine; 2014, 7:137-144.
Elez et al., Annals of Oncology; 2015, 26:132-140.
Elez et al., J Clin Oncol., 2012; 30:suppl. abstract 3539.
Goel et al., Cancer Treat Res; 2004, 119:15-31.
Goodman et al., Biology Open; 2012, 1:329-340.
Goodman et al., Trends in Pharmacological Sciences; 2012, 33(7):405-412.
Graselli et al., Annals of Oncology; 2017, 28:1294-1301.
Guidance for Industry—Clinical Trial Endpoints for the Approval of Cancer Drugs and Biologics—2007.
Guideline on the evaluation of anticancer medicinal products in man (2013).
Lee et al., Journal of the National Comprehensive Cancer Network, 2017, 15(3):411-419.
Lee, Journal of Clinical Oncology; 2017, 35(4):abstract 682.
McCabe et al., Oncogene; 2007, 26(42):6238-6243.
McCarty et al., Arch Pathol Lab Med; 1985, 109:716-721.
Mik et al., Arch Med Sci; 2017, 13(1):157-162.
Mitjans et al., Journal of Cell Science; 1995, 108:2825-2838.
Nemeth et al., Cancer Investigation; 2007, 25(7):632-646.
News Release dated May 2, 2018: "Merck to Develop Abituzumab in Metastatic Colorectal Cancer with SFJ Pharmaceuticals Group".
Niu et al., Cell & Bioscience; 2014, 4:23.
Normanno et al., Annals of Oncology; 2018, 29:112-118.
Pirker et al., The Lancet Oncology; 2012, 13:33-42.
Riihimäki et al., Scientific Reports, 2016; 6:29765.
Therasse et al., Journal of the National Cancer Institute; 2000, 92(3):205-216.
Travis et al., Annu Rev Immunol; 2014, 32:51-82.
Uhl et al., Invest New Drugs; 2014, 32:347-354.
Van Cutsem et al., Annals of Oncology; 2014, 25(3):iii1-iii9.
Van Krieken et al., Virchovs Arch; 2016, 468:383-396.
Vidal et al., Annals of Oncology; 2017, 28:1325-1332.
Wagner et al., Biomaterials; 2010, 31:2388-2398.
Wirth et al., European Urology; 2014, 65:897-904.
Yang et al., World Journal of Gastroenterol; 2015, 21(24):7457-7467.
Douillard et al., "Relationship Between EGFR Expression, EGFR Mutation Status, and the Efficacy of Chemotherapy Plus Cetuximab in FLEX Study patients with Advanced Non-Small-Cell lung Cancer", Journal of Thoracic Oncology, vol. 9, No. 5, May 2014, pp. 717-724.
J. Grass, "ABITUZUMAB—Anti-Integrin av (CD51, ITGAV) Mab Oncolytic", Drugs of the Future, vol. 40, No. 2, 2015, pp. 97-100.
Rüschoff et al., "Reproducibility of Immunohistochemical Scoring for Epidermal Growth Factor Receptor Expression in Non-Small Cell Lung Cancer", Arch Pathol. Lab. Med., vol. 137, Sep. 2013, pp. 1255-1261.
Straub et al., "Abstract 582: Prognostic and predictive value of plasma protein signatures in phase I/II trial of abituzumab combined with cetuximab/irinotecan in second-line KRAS wild-type metastatic colorectal cancer (mCRC)", Cancer Research, vol. 75 Issue 15, DOI:10.1158/1538, Aug. 2015, 4 pages.
Merck News Release, "Merck to Develop Abituzumab in Metastatic Colorectal Cancer with SFJ Pharmaceuticals Group", May 2, 2018, 3 pages.
Laeufle et al., Poster No. 487P, "Patient Selection for targeting integrin with abituzumab in patients with metastatic colorectal cancer (mCRC). A retrospective analysis of the of the randomized phase I/II Poseidon study", presented at European Society for Medical Oncology, of Oct. 19-23, 2018.
Boeckx et-al., "Primary tumor sidedness has an impact on prognosis and treatment outcome in metastatic colorectal cancer: results from two randomized first-line panitumumab studies", Annals of Oncology, vol. 28, Issue 8, Aug. 2017, pp. 1862-1868.

* cited by examiner

ABITUZUMAB FOR THE TREATMENT OF COLORECTAL CANCER

CROSS-REFERENCE TO RELATED APPLICATIONS

The present application claims the benefit to the provisional application 62/748,114, filed on Oct. 19, 2018, which is incorporated by reference in its entirety.

REFERENCE TO A SEQUENCE LISTING

The present application incorporates by reference the material in the ASCII text file "2019-10-07-P18-218_ST25.txt," created on Oct. 7, 2019, having a size of 7878 bytes, which is submitted herewith.

BACKGROUND OF THE INVENTION

Field of the Invention

Methods of treatment of colorectal cancer can comprise the administration of the anti-alpha-v integrin (receptor) antibody Abituzumab. Preferably, such methods relate to treating colorectal cancer, Stage II-IV colorectal cancer, metastatic colorectal cancer, left-sided colorectal cancer and/or left-sided metastatic colorectal comprising the administration of said Abituzumab to patients in need thereof. More preferably, such methods relate to treating colorectal cancer, preferably the above given kinds or stages of colorectal cancer, said methods comprising the administration of the anti-alpha-v integrin (receptor) antibody Abituzumab additionally to an existing treatment or treatment regimen for said kinds or stages of colorectal cancer. Thus, Abituzumab may be used for the manufacture of a medicament for treating colorectal cancer, preferably colorectal cancer as defined herein, and/or Abituzumab for the manufacture of a medicament for treating colorectal cancer in combination with suitable targeted therapy concepts, such as growth factor or growth factor receptor targeting monoclonal antibodies, and/or chemotherapy.

Discussion of the Background

Colorectal cancer (preferably also known as colon cancer, rectal cancer and/or bowel cancer) is when cancer develops in the colon or rectum (parts of the large intestine). It is due to the abnormal growth of cells that they generally have the ability to invade or spread to other parts of the body.

To date, treatments used for colorectal cancer may include some combination of surgery, radiation therapy, chemotherapy and targeted therapy. Cancers that are confined within the wall of the colon may be curable with surgery while cancer that has spread widely are usually not curable with management focusing on improving quality of life and symptoms. Five-year survival rates in the United States are around 65%. This, however, depends on how advanced the cancer is, whether or not all the cancer can be removed with surgery, and the person's overall health. Globally, colorectal cancer is the third most common type of cancer making up about 10% of all cases. In 2012 it resulted in 1.4 million new cases and caused 694,000 deaths. It is more common in developed countries where more than 65% of occur. It is less common in women than men.

In both cancer of the colon and rectum, chemotherapy may be used in addition to surgery in certain cases. In rectal cancer, chemotherapy may be used in the neoadjuvant setting.

If cancer has entered the lymph nodes, adding the chemotherapy agents fluorouracil or capecitabine increases life expectancy. If the lymph nodes do not contain cancer, the benefits of chemotherapy are controversial. If the cancer is widely metastatic or unresectable, up to now, treatment is mainly palliative. Typically in this setting, a number of different chemotherapy medications may be used. Chemotherapy drugs for this condition may include capecitabine, fluorouracil, irinotecan, leucovorin, oxaliplatin and UFT. Preferably, fluorouracil may be administered as its Prodrugs, such as Capecitabine and/or 5-Fluorocytosine. Another type of agent that is sometimes used are the epidermal growth factor receptor inhibitors.

While a combination of radiation and chemotherapy may be useful for rectal cancer, its use in colon cancer is not routine due to the sensitivity of the bowels to radiation. Just as for chemotherapy, radiotherapy can be used in the neoadjuvant and adjuvant setting for some stages of rectal cancer.

However, the indication colorectal cancer (CRC) is known and widely understood in the art. Preferably, colorectal cancer is a heterogeneous indication disease that can preferably be distinguished by characteristics, including, but not limited to the location of origin, the kind of tissue affected and/or the stage of the disease as it develops.

The staging of colorectal cancer is widely known and understood in the art. Preferably, the different stages of development are divided in four or five categories, preferably four categories. The earliest stage colorectal cancers are preferably categorised "stage 0" (a very early cancer), and then range from stages I (1) through IV (4). As a rule, the lower the number, the less the cancer has developed, progressed and/or spread. A higher number, such as stage IV, preferably means cancer has spread more. And within a stage, an earlier letter preferably means a lower stage. Although each person's cancer experience is unique, cancers with similar stages tend to have a similar outlook and are often treated in much the same way.

The staging system most often used for colorectal cancer is the American Joint Committee on Cancer (AJCC) TNM system, which is based on 3 key pieces of information:

The extent (size) of the tumor (T): How far has the cancer grown into the wall of the colon or rectum? These layers, from the inner to the outer layers as shown in FIG. 1, include:
  The inner lining (mucosa), which is the layer in which nearly all colorectal cancers start. This includes a thin muscle layer (muscularis mucosa).
  The fibrous tissue beneath this muscle layer (submucosa)
  A thick muscle layer (muscularis propria)
  The thin, outermost layers of connective tissue (subserosa and serosa) that cover most of the colon but not the rectum
The spread to nearby lymph nodes (N): Has the cancer spread to nearby lymph nodes?
The spread (metastasis) to distant sites (M): Has the cancer spread to distant lymph nodes or distant organs such as the liver or lungs?

The system described below is the most recent AJCC system effective January 2018. It uses the pathologic stage (also called the surgical stage) which is determined by examining tissue removed during an operation. This is also known as surgical staging. This is likely to be more accurate than clinical staging, which takes into account the results of a physical exam, biopsies, and imaging tests, preferably done before surgery.

Numbers or letters after T, N, and M provide more details about each of these factors. Higher numbers mean the cancer is more advanced. Once a person's T, N, and M categories have been determined, this information is combined in a process called stage grouping to assign an overall stage.

TABLE 1

| AJCC Stage | Stage grouping | Stage description* |
|---|---|---|
| 0 | Tis<br>N0<br>M0 | The cancer is in its earliest stage. This stage is also known as carcinoma in situ or intramucosal carcinoma (Tis). It has not grown beyond the inner layer (mucosa) of the colon or rectum. |
| I | T1 or T2<br>N0<br>M0 | The cancer has grown through the muscularis mucosa into the submucosa (T1), and it may also have grown into the muscularis propria (T2). It has not spread to nearby lymph nodes (N0) or to distant sites (M0). |
| IIA | T3<br>N0<br>M0 | The cancer has grown into the outermost layers of the colon or rectum but has not gone through them (T3). It has not reached nearby organs. It has not spread to nearby lymph nodes (N0) or to distant sites (M0). |
| IIB | T4a<br>N0<br>M0 | The cancer has grown through the wall of the colon or rectum but has not grown into other nearby tissues or organs (T4a). It has not yet spread to nearby lymph nodes (N0) or to distant sites (M0). |
| IIC | T4b<br>N0<br>M0 | The cancer has grown through the wall of the colon or rectum and is attached to or has grown into other nearby tissues or organs (T4b). It has not yet spread to nearby lymph nodes (N0) or to distant sites (M0). |
| IIIA | T1 or T2<br>N1/N1c<br>M0 | The cancer has grown through the mucosa into the submucosa (T1), and it may also have grown into the muscularis propria (T2). It has spread to 1 to 3 nearby lymph nodes (N1) or into areas of fat near the lymph nodes but not the nodes themselves (N1c). It has not spread to distant sites (M0). |
| | OR<br>T1<br>N2a<br>M0 | The cancer has grown through the mucosa into the submucosa (T1). It has spread to 4 to 6 nearby lymph nodes (N2a). It has not spread to distant sites (M0). |
| IIIB | T3 or T4a,<br>N1/N1c<br>M0 | The cancer has grown into the outermost layers of the colon or rectum (T3) or through the visceral peritoneum (T4a) but has not reached nearby organs. It has spread to 1 to 3 nearby lymph nodes (N1a or N1b) or into areas of fat near the lymph nodes but not the nodes themselves (N1c). It has not spread to distant sites (M0). |
| | OR<br>T2 or T3<br>N2a<br>M0 | The cancer has grown into the muscularis propria (T2) or into the outermost layers of the colon or rectum (T3). It has spread to 4 to 6 nearby lymph nodes (N2a). It has not spread to distant sites (M0). |
| | OR<br>T1 or T2<br>N2b<br>M0 | The cancer has grown through the mucosa into the submucosa (T1), and it may also have grown into the muscularis propria (T2). It has spread to 7 or more nearby lymph nodes (N2b). It has not spread to distant sites (M0). |
| IIIC | T4a<br>N2a<br>M0 | The cancer has grown through the wall of the colon or rectum (including the visceral peritoneum) but has not reached nearby organs (T4a). It has spread to 4 to 6 nearby lymph nodes (N2a). It has not spread to distant sites (M0). |
| | OR<br>T3 or T4a<br>N2b<br>M0 | The cancer has grown into the outermost layers of the colon or rectum (T3) or through the visceral peritoneum (T4a) but has not reached nearby organs. It has spread to 7 or more nearby lymph nodes (N2b). It has not spread to distant sites (M0). |
| | OR<br>T4b<br>N1 or N2<br>M0 | The cancer has grown through the wall of the colon or rectum and is attached to or has grown into other nearby tissues or organs (T4b). It has spread to at least one nearby lymph node or into areas of fat near the lymph nodes (N1 or N2). It has not spread to distant sites (M0). |
| IVA | Any T<br>Any N<br>M1a | The cancer may or may not have grown through the wall of the colon or rectum (Any T). It might or might not have spread to nearby lymph nodes. (Any N). It has spread to 1 distant organ (such as the liver or lung) or distant set of lymph nodes, but not to distant parts of the peritoneum (the lining of the abdominal cavity) (M1a). |

TABLE 1-continued

AJCC Stages

| AJCC Stage | Stage grouping | Stage description* |
|---|---|---|
| IVB | Any T<br>Any N<br>M1b | The cancer might or might not have grown through the wall of the colon or rectum (Any T). It might or might not have spread to nearby lymph nodes (Any N). It has spread to more than 1 distant organ (such as the liver or lung) or distant set of lymph nodes, but not to distant parts of the peritoneum (the lining of the abdominal cavity) (M1b). |
| IVC | Any T<br>Any N<br>M1c | The cancer might or might not have grown through the wall of the colon or rectum (Any T). It might or might not have spread to nearby lymph nodes (Any N). It has spread to distant parts of the peritoneum (the lining of the abdominal cavity), and may or may not have spread to distant organs or lymph nodes (M1c). |

More generally, colorectal cancer can be classified in four stages: Stage I, Stage II, Stage III and Stage IV. The higher the stage the more advanced is the colorectal cancer. Preferably, Stage I means that the cancer can be diagnosed at a specific colorectal location yet, but has not yet really started to grow. In stage II colorectal cancer, the tumor has grown in the original colorectal location, but has not extended beyond it, whereas in stage III, the cancer has spread outside the original colorectal location, e.g. via metastasis, but to a minimal extent only. Often, colorectal cancer in stage III will have spread only to nearby tissues, such as adjacent tissues and nearby lymph nodes. Finally, in stage IV, the cancer has spread outside the original location in the colorectal area to other tissues, such as distant lymph nodes, bones, liver, lungs and/or brain, see e.g. Matias Riihimäki, Akseli Hemminki, Jan Sundquist, Kari Hemminki, Scientific Reports|6: 29765|DOI: 10.1038/srep29765, the disclosure of which is preferably incorporated herein by reference in its entirety.

Since 1996, treatment options for CRC and/or mCRC have expanded, particularly with the introduction of chemotherapies such as irinotecan and oxaliplatin and targeted agents such as cetuximab, panitumumab, aflibercept, regorafenib and bevacizumab. Currently, treatment of colorectal cancer and especially advanced colorectal cancer by means of a combined chemotherapy regimen comprising 5-FU and irinotecan is an established treatment. These have improved patient outcomes, but still most patients die due to their disease.

With increasing understanding of the molecular biology of CRC and the newly found impact of side-ness on treatment outcome, novel combination therapies targeting factors essential to tumor growth and progression offer the best hope of improvement in patient outcomes. Essentially, existing treatment of mCRC is still based upon five different mechanisms of action to destroy the tumor cells, namely blocking the thymidylate synthetase, intercalating with DNA (platinum compounds), targeting Topoisomerase I (irinotecan), targeting growth factors or growth factor receptors, including, but not limited to EGF (Epidermal Growth Factor), EGFR (Epidermal Growth Factor Receptor), VEGF (Vascular Endothelial Growth Factor) and/or VEGFR (Vascular Endothelial Growth Factor Receptor).

The use of integrin inhibitors is hypothesized to affect both cancer cell survival and angiogenesis since integrins are expressed by tumor cells as well as by endothelial cells. Although it is hard to discriminate between an effect on tumor growth and an effect on angiogenesis, a maximal response of these inhibitors can be predicted when the targeted integrin is expressed by both tumor and endothelial cells.

Bone is one of the frequent metastatic sites for various cancers, including, but not limited to CRC. Bisanz et al. (Molecular Therapy 2005; 12, 634-643) illustrate a positive role for alpha-v integrins on, e.g. prostate tumor survival in the bone. Further studies (McCabe et al., Oncogene 2007; 26, 6238-6243) demonstrate that αvβ3 integrin activation on tumor cells is essential for the recognition of key bone specific matrix proteins. These data suggest that the αvβ3 integrin modulates cancer growth in distant metastasis.

Since integrins are hypothesized to mediate the interactions between tumor cells and bone microenvironment and facilitate growth in bone, a potential application of the use of integrin inhibitors is to prevent CRC cancer bone lesions. These lesions are preferably osteoblastic and/or osteolytic and are frequently detected in cancer patients. In some cancers, over 80% of patients have established bone metastasis at autopsy.

Furthermore, immunohistochemical analysis has demonstrated the presence of αv integrin in a large proportion of human CRC cancer tissues samples.

Therefore, there is high need to provide a new highly potent therapeutic agent and/or highly efficacious treatment regimen for the treatment of colorectal cancer. Thus, it is a preferred objective of the instant invention to provide a more effective, better tolerated treatment for humans, especially human patients suffering from colorectal cancer (CRC) and/or metastases thereof and especially metastatic colorectal cancer (mCRC), preferably independent from the location of the metastases, thus preferably leading to enhanced overall survival (OS), progression-free survival (PFS), quality of life (QOL) and/or increased median survival.

SUMMARY OF THE INVENTION

According to the instant invention, the high need to provide a new highly potent therapeutic agent for the treatment of colorectal cancer is met by the provision of the anti-alpha-v integrin (receptor) antibody Abituzumab for use in methods of treating colorectal cancer in patients with tumors and/or metastases with high integrin expression and especially with high αvβ6 integrin expression. More preferably, the high need to provide a new highly potent therapeutic agent for the treatment of colorectal cancer is met by the provision of the anti-alpha-v integrin (receptor) antibody Abituzumab preferably left-sided colorectal cancer, more preferably left-sided metastatic colorectal cancer, especially in patients with tumors and/or metastases with high integrin expression and especially with high αvβ6 integrin expression. Preferably, also the up to now high unmet need to provide a new highly efficacious treatment regimen for the treatment of colorectal cancer is met according to the instant invention.

In this regard, Abituzumab has been found to preferably have both a direct and indirect antitumor activity in colorectal cancer.

Abituzumab is a recombinant, humanized monoclonal IgG2 antibody antagonist directed against the alpha-beta sub-unit of human integrin receptors. Abituzumab is a pan-integrin inhibitor specific for αv integrins, inhibits all αv heterodimers (αvβ1, β3, β5, β6 and β8). Specifically, Abituzumab inhibits αvβ6 which displays enhanced activity in metastatic colorectal cancer (mCRC) and has been discussed as a negative prognostic factor for the disease (Bates R C, Bellovin D I, Brown C, et al. "Transcriptional activation of integrin 136 during the epithelial-mesenchymal transition defines a novel prognostic indicator of aggressive colon carcinoma". The Journal of Clinical Investigation. 2005; 115 (2):339-347; Niu Z, Wang J, Muhammad S, et al. "Protein expression of eIF4E and integrin αvβ6 in colon cancer can predict clinical significance, reveal their correlation and imply possible mechanism of interaction" Cell & Bioscience. 2014; Yang G Y, Guo S, Dong C Y, et al. "Integrin αvβ6 sustains and promotes tumor invasive growth in colon cancer progression". World Journal of Gastroenterol. 2015; 21(24):7457-7467), the disclosure of which is preferably incorporated herein by reference in their entirety. Integrins are a family of cell adhesion molecules that play a role in a wide range of cell-extracellular matrix (ECM) and cell-cell interactions Arnaout M A, Goodman S L, Xiong J P. Structure and mechanics of integrin-based cell adhesion. Curr Opin Cell Biol. 2007; 19(5):495-507, the disclosure of which is preferably incorporated herein by reference in its entirety. Integrins are heterodimeric transmembrane receptors for ECM proteins consisting of an alpha (α) and a beta (β) sub-unit. They are activated by binding to their respective ECM ligands. Following this interaction, integrins can trigger intracellular kinase cascades to modulate cell proliferation and survival and become associated with the actin cytoskeleton to drive cell attachment and locomotion (Goel H L, Languino L R. Integrin signaling in cancer. Cancer Treat Res. 2004; 119:15 31, the disclosure of which is preferably incorporated herein by reference in its entirety).

Alpha-v-integrins are highly expressed in angiogenic, proliferating tumor blood vessels and on certain types of tumor cells. It has been demonstrated that members of the αvβ6 integrin family play a direct role in tumor progression, tumor angiogenesis, and metastasis (Nemeth J A, Nakada M T, Trikha M, et al. Alpha-v integrins as therapeutic targets in oncology. Cancer Invest. 2007; 25(7):632-646, the disclosure of which is preferably incorporated herein by reference in its entirety).

According to the invention, the targeting of integrins, including αvβ6, but not limited to αvβ6, with Abituzumab in CRC patients with high integrin expression, preferably high αvβ6 integrin expression is a surprisingly advantageous novel approach to the treatment of CRC and/or mCRC, especially if combined with other targeted therapeutics and/or chemotherapy having shown efficacy in CRC and/or mCRC.

Thus, preferred subjects of the instant invention comprise one or more of the following:

A method of treating colorectal cancer in humans, preferably as described above and/or below, said method comprising administering Abituzumab to said humans, wherein said colorectal cancer is characterised by high αvβ6 integrin expression.

A method of treating colorectal cancer in humans command preferably as described above and/or below, said method comprising administering Abituzumab to said humans, wherein said colorectal cancer is left-sided colorectal cancer.

A method of treating left-sided colorectal cancer, preferably as described above and/or below, said method comprising administering Abituzumab to said humans, wherein said left-sided colorectal cancer is characterised by high αvβ6 integrin expression.

The method as described above and/or below wherein said colorectal cancer is metastatic colorectal cancer.

The method as described above and/or below, wherein said Abituzumab is administered to said humans in an amount of about 1000 mg every second week or in an amount of about 2000 mg per month.

The method as described above and/or below, wherein said humans also receive at least one growth factor or growth factor receptor targeting monoclonal antibody, and/or chemotherapy.

The method as described above and/or below, wherein said humans also receive one or more of the treatment options of the current standard of care (SoC) in the treatment of colorectal cancer as described above and/or below.

The method as described as above and/or below, wherein
a) said colorectal cancer is RAS wild-type and/or KRAS wild-type left-sided colorectal cancer or RAS wild-type and/or KRAS wild-type left-sided metastatic colorectal cancer,
b) said humans also receive at least one growth factor or growth factor receptor targeting monoclonal antibody, which is preferably cetuximab, and
c) said humans optionally receive chemotherapy according to the FOLFIRI or FOLFOX protocol, preferably according to the FOLFIRI protocol.

Further aspects of the instant invention are discussed in more detail below.

DETAILED DESCRIPTION OF THE INVENTION

Histochemical data show that the targets of αv-integrins are expressed on the tumor vasculature and tumor cells of CRC and/or mCRC. In particular, αvβ6 integrin expression has also been discussed as a prognostic factor in CRC as it was analyzed in more than 700 mCRC patients (Bates R C, Bellovin D I, Brown C, et al. "Transcriptional activation of integrin 136 during the epithelial-mesenchymal transition defines a novel prognostic indicator of aggressive colon carcinoma". The Journal of Clinical Investigation. 2005; 115 (2):339-347; Niu Z, Wang J, Muhammad S, et al. "Protein expression of eIF4E and integrin αvβ6 in colon cancer can predict clinical significance, reveal their correlation and imply possible mechanism of interaction" Cell & Bioscience. 2014; Yang G Y, Guo S, Dong C Y, et al. "Integrin αvβ6 sustains and promotes tumor invasive growth in colon cancer progression". World Journal of Gastroenterol. 2015; 21(24):7457-7467), the disclosure of which is preferably incorporated herein by reference in their entirety. Thus, according to the invention, high αvβ6 expression in colon and/or rectal cancer tumors are believed to be indicators of tumor's progression and poor survival of these patients.

Figure 1:
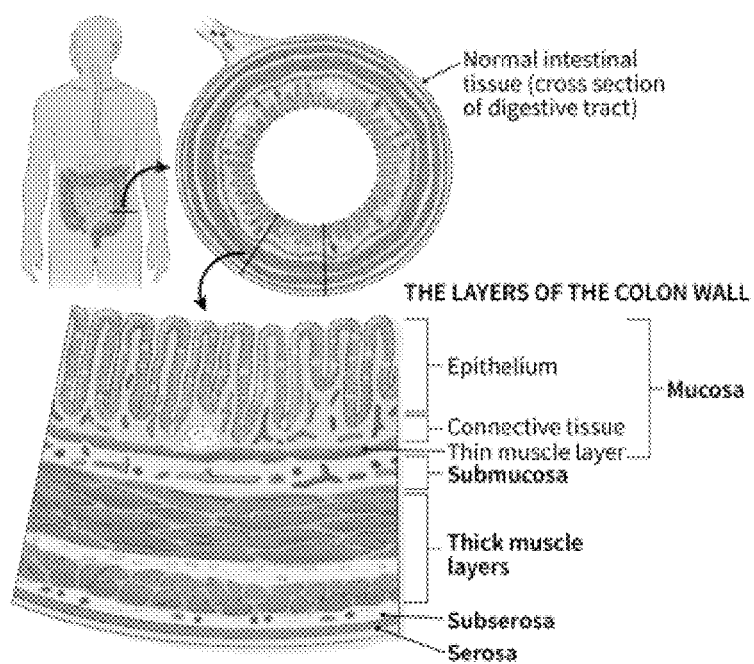
FIG. 1 shows a general structure of human intestinal tissue and colon wall layers.
Figure 2:
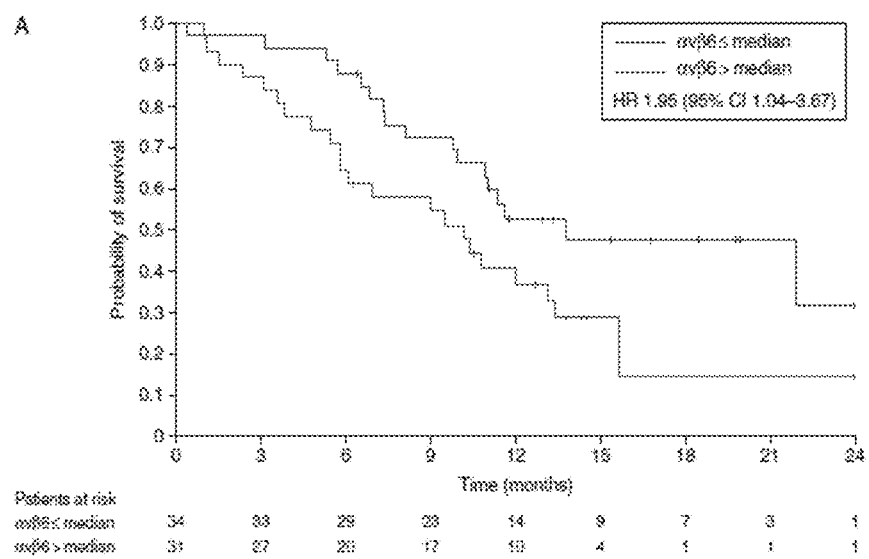
FIG. 2 shows an OS curve based on αvβ6 expression in cetuximab+irinotecan alone group (POSEIDON), where αvβ6>median is the lower curve at 24 months and αvβ6<median is the higher curve at 24 months.

In our recent re-evaluation of the data obtained from our POSEIDON study (Elez E, Kocáková I, Höhler T, et al. Abituzumab combined with cetuximab plus irinotecan versus cetuximab plus irinotecan alone for patients with KRAS wild-type metastatic colorectal cancer: the randomised phase I/II POSEIDON trial. Annals of Oncology. 2015; 26: 132-140, the disclosure of which is preferably incorporated herein by reference in its entirety), exploring the activity of Abituzumab in combination with cetuximab and irinotecan in 2nd line KRAS WT mCRC, the analysis of the cetuximab+irinotecan alone group demonstrated that high αvβ6 expression is associated with a poorer outcome, preferably showing that a high αvβ6 expression is a negative prognostic factor (FIG. 2). In addition, our recent re-evaluation of the data from the POSEIDON study showed that patients with high αvβ6 expression treated with Abituzumab achieved a higher PFS, thus preferably showing that high αvβ6 expression is predictive for response to Abituzumab.

Furthermore, in the context of Abituzumab treatment, we found increasing evidence that CRC and especially mCRC is a genetically heterogeneous disease and that tumors arising from different sides of the colon (left versus right) have different clinical outcomes (Bever K M, Le D T. An Expanding Role for Immunotherapy in Colorectal Cancers. Journal of the National Comprehensive Cancer Network. 2017; 15(3):401-410; Lee M S, Menter D G, Kopets S. Right Versus Left Colon Cancer Biology: Integrating the Consensus Molecular Subtypes. Journal of the National Comprehensive Cancer Network. 2017; 15(3):411-419, Lee B, et al. Left versus right sided colorectal cancer: Teasing out drivers of disparity in outcomes in metastatic disease. Journal of Clinical Oncology. 2017; 35:4_suppl, 682-682, the disclosure of which is preferably incorporated herein by reference in their entirety). Analyses comparing the activity of different classes of targeted agents in patients with KRAS wild-type (WT) or RAS WT mCRC suggest that primary tumor location (side), might be both, prognostic and predictive for clinical outcome in the context of mCRC.

Retrospective analysis investigated the prognostic and predictive influence of the localization of the primary tumor in patients with un-resectable RAS WT and/or KRAS WT mCRC included in six randomized trials (CRYSTAL, FIRE-3, CALGB 80405, PRIME, PEAK and 20050181), comparing chemotherapy plus EGFR antibody therapy (experimental arm) with chemotherapy or chemotherapy and bevacizumab (control arms). Hazard ratios (HRs) and 95% confidence intervals (CIs) for overall survival (OS) and progression-free survival (PFS) for patients with left-sided versus right-sided tumors, and odds ratios (ORs) for objective response rate (ORR) were estimated by pooling individual study HRs/ORs[10].

The predictive value was evaluated by retrospective correlation of treatment effect and tumor side. The result of this analysis revealed, that the primary tumor location and RAS mutation status which were available for 2,159 of the 5,760 patients (37.5%) randomized across the 6 trials, 515 right-sided and 1,644 left-sided a significantly worse prognosis was observed for patients with right-sided tumors compared with those with left-sided tumors in both the pooled control and experimental arms for OS (HRs 2.03 (95% CI: 1.69-2.42) and 1.38 (1.17-1.63), respectively), PFS (HRs 1.59 (1.34-1.88) and 1.25 (1.06-1.47)) and ORR (ORs 0.38 (0.28-0.50) and 0.56 (0.43-0.73)).

In terms of a predictive effect, a significant benefit for chemotherapy plus EGFR antibody therapy was observed in patients with left-sided tumors (HRs 0.75 (0.67-0.84) and 0.78 (0.70-0.87)) for OS and PFS, respectively, compared with no significant benefit for those with right-sided tumors (HRs 1.12 (0.87-1.45) and 1.12 (0.87-1.44)) for OS and PFS, respectively; P value were <0.001 and 0.002, respectively. For ORR, there was a trend (P value of 0.07) towards a greater benefit for chemotherapy plus EGFR antibody therapy in the patients with left-sided tumors (HR 2.12 (1.77-2.55)) compared with those with right-sided tumors (HR 1.47 (0.94-2.29)).

This analysis shows a worse prognosis for OS, PFS and ORR for patients with right-sided tumors compared with those with left-sided tumors in patients with RAS WT and/or KRAS WT mCRC and a predictive effect of tumor side, with a greater effect of chemotherapy plus cetuximab compared with chemotherapy or chemotherapy and bevacizumab, the effect being greatest in patients with left-sided tumors although the results are based on subpopulations of patients in these trials and the retrospective nature of the analysis.

Non-Clinical Study Data

αv-integrins are expressed on a variety of tumor cells, tumor-invasive vessels, and tumor stroma cells of primary tumors and metastases across a large number of tumor indications.

Preferably, Abituzumab has the power to inhibit tumor progression by inhibiting angiogenesis, by modifying the stroma and/or by targeting tumor cells directly.

In vitro, Abituzumab has been shown to preferably interfere with several aspects involved in tumor angiogenesis, such as endothelial cell attachment to the EMC, destabilization of focal contacts, endothelial cell migration, transmission of angiogenic growth factor signals, and/or endothelial cell viability. In vivo, the anti-angiogenic effect of Abituzumab can be and preferably has demonstrated in a variety of animal models.

Abituzumab preferably also directly affects tumor cells. Abituzumab preferably reduces tumor cell adhesion to αv integrin ligands. Abituzumab preferably inhibits tumor growth in several tumor xenograft models of different indications with differential αv-integrin heterodimer expression. In addition to its monotherapeutic activity, Abituzumab can be shown to enhance the effect of several chemotherapeutics and cetuximab in a variety of models.

No relevant findings for major body systems such as cardiovascular and respiratory system or clinical behavior were observed during the safety pharmacological evaluation within the repeated-dose toxicity studies of Abituzumab in cynomolgus monkeys. No treatment-related impairment of heart rate, ECG parameters including QTc interval were observed in chronic 6-month IV infusion toxicity study.

In summary, the scientific evidence provided herein support for the use of Abituzumab as a drug with antiangiogenic and direct antitumor activity, which, when administered alone or in combination with Standard of Care (SoC) treatment options or preferably in combination with growth factor targeting monoclonal antibodies or growth factor receptor targeting monoclonal antibodies, including, but not limited to cetuximab, and/or chemotherapy, preferably provides a surprisingly advantageous therapeutic concept for the treatment of colorectal cancer, and especially metastatic colorectal cancer, preferably as described herein.

Clinical Study Data

Phase I/II Study for Patients with KRAS WT mCRC

EMR 62242-004 "POSEIDON Study[7]" was an open-label, randomized, controlled, multicenter, phase I/II Trial investigating Abituzumab in two doses (i.e., 500 mg and 1,000 mg IV) in combination with cetuximab+irinotecan versus cetuximab+irinotecan alone, as second-line treatment for patients with KRAS WT, mCRC. Patients with KRAS WT mCRC were eligible for enrollment if they were refractory to or progressive after first-line chemotherapy with an Oxaliplatin-containing therapeutic regimen.

The study was a Phase I/II study dose finding/safety study to characterize the safety and tolerability profile of repeated administration of different dose levels of Abituzumab, in combination with cetuximab+irinotecan. The study had as the primary objective to assess the anticancer activity of the two Abituzumab doses in terms of PFS.

The secondary objectives were to evaluate the efficacy of the two Abituzumab doses with respect to overall survival (OS), time to tumor progression (TTP), tumor response (Response Evaluation Criteria in Solid Tumors [RECIST], Version 1.0), and time to treatment failure (TTF).

Other objectives included to identify potential predictive markers of response for the treatment under investigation by exploring the relationship between candidate proteins circulating in the blood and/or expressed by the tumor and the efficacy and safety endpoints.

A total of 232 patients were enrolled, 16 in the phase I part and 216 patients in the randomized phase II part of the study.

In the phase II part, seventy-three patients were randomized to the Abituzumab 500 mg IV dose in combination with cetuximab+irinotecan group, 71 to the Abituzumab 1000 mg IV dose in combination with cetuximab+irinotecan group, and 72 to the cetuximab+irinotecan alone group. The number of patients in the per-protocol (PP) analysis set was 197 (66 in the Abituzumab 500 mg in combination with cetuximab+irinotecan group, 65 in the Abituzumab 1000 mg in combination with cetuximab+irinotecan group, 66 in the cetuximab+irinotecan alone group). The incidence of patients with major protocol deviations was low and generally similar between all the treatment groups.

Efficacy Results in ITT Population:

The primary efficacy endpoint was PFS based on the investigator's assessment. As of the data cutoff date, the estimated HRs from a Cox proportional hazard model for the individual Abituzumab 500 mg in combination with cetuximab+irinotecan and 1000 mg in combination with cetuximab+irinotecan groups versus cetuximab+irinotecan alone were 1.13 (95% CI: 0.78, 1.64) and 1.11 (95% CI: 0.77, 1.61), respectively, indicating no difference between the groups. The median PFS time was comparable across the Abituzumab 500 mg in combination with cetuximab+irinotecan, Abituzumab 1000 mg in combination with cetuximab+irinotecan, and cetuximab+irinotecan alone groups (5.4 months [95% CI: 4.1, 6.0], 5.6 months [95% CI: 4.1, 6.9], and 5.6 months [95% CI: 4.2, 6.9], respectively).

Results from the OS analysis showed a possible trend toward favorable findings for Abituzumab. The number and percent of patients with an event (death from any cause) was lower in the Abituzumab in combination with cetuximab+irinotecan groups than cetuximab+irinotecan alone group, with 39 (53.4%), 35 (49.3%), and 45 (62.5%) patients in the Abituzumab 500 mg in combination with cetuximab+irinotecan, Abituzumab 1000 mg in combination with cetuximab+irinotecan, and cetuximab+irinotecan alone groups, respectively. The HRs for the Abituzumab 500 mg and 1000 mg in combination with cetuximab+irinotecan groups versus cetuximab+irinotecan alone groups were 0.83 (95% CI: 0.54, 1.28) and 0.80 (95% CI: 0.52, 1.25), respectively, favoring Abituzumab. The median OS was 15.0 months (95% CI: 10 Abituzumab 500 mg in combination with cetuximab+irinotecan, Abituzumab 1000 mg in combination with cetuximab+irinotecan, and cetuximab+irinotecan alone, respectively. 0.9, 19.2), 14.4 months (95% CI: 9.8, 19.3), and 11.6 months (95% CI: 9.8, 15.7) for Exploratory Biomarker Results:

The following high-level overview summarizes the main biomarker findings:

An immunohistochemistry-based target ($\alpha v\beta 3$, $\alpha v\beta 5$, $\alpha v\beta 6$, $\alpha v\beta 8$, pan $\alpha v\beta$) and target ligand (Osteopontin, Vitronectin) expression analysis was performed.

A high expression of the integrin $\alpha v\beta 6$ was identified as negative prognostic (predicting shorter survival in the cetuximab+irinotecan alone group) and predictive of prolonged OS with Abituzumab treatment. The $\alpha v\beta 6$ biomarker subset consisted of 197 patients representing 91% of the ITT population of the Randomized Part of the POSEIDON study.

Additional immunohistochemistry was performed for candidate markers including integrins $\alpha v\beta 3$, $\alpha v\beta 5$, $\alpha v\beta 8$, pan $\alpha v\beta$ and Osteopontin, however, none of the additional makers tested showed a prognostic or predictive correlation.

The analysis of the influence of VEGF-containing first-line treatments on the OS of patients with a high $\alpha v\beta 6$ histoscore revealed no difference regarding HR in the 2 groups.

Immunogenicity Results:

The immunogenicity characteristics of Abituzumab are advantageously positive, as no patient tested positive for neutralizing antibodies to Abituzumab.

Safety Results:

All patients in the study experienced 1 or more treatment-emergent AEs with the exception of 1 patient in the cetuximab+irinotecan alone group. The number and percent of patients with TEAEs that were considered related to at least 1 of the 3 study medications were comparable across the 3 groups; the number and percent of patients with TEAEs that were considered related to Abituzumab were 35 (48.6%) patients and 39 (56.5%) patients in the Abituzumab 500 mg and 1000 mg groups, respectively.

TEAEs that were Grade 3 or higher were reported at a slighter higher incidence in the Abituzumab 500 mg and 1000 mg groups versus cetuximab+irinotecan alone group (52 [72.2%], 54 [78.3%], and 49 [67.1%] patients, respectively). The TEAEs that led to discontinuation of Abituzumab were reported in 16 (22.2%) and 12 (17.4%) patients in the Abituzumab 500 mg and 1000 mg groups, respectively; there was no apparent relationship to dose. The incidence of serious TEAEs was highest in the Abituzumab 1000 mg treatment group versus the other treatment groups: across the Abituzumab 500 mg, Abituzumab 1000 mg, and cetuximab+irinotecan alone groups, the incidence was 26 (36.1%), 34 (49.3%), and 29 (39.7%) patients, respectively. TEAEs with a fatal outcome occurred in 9 (12.5%), 7 (10.1%), and 6 (8.2%) patients, respectively.

In conclusion, rising doses from 250 mg to 1000 mg of Abituzumab in the POSEIDON study were well tolerated and no major safety concerns were observed.

Figure 3:
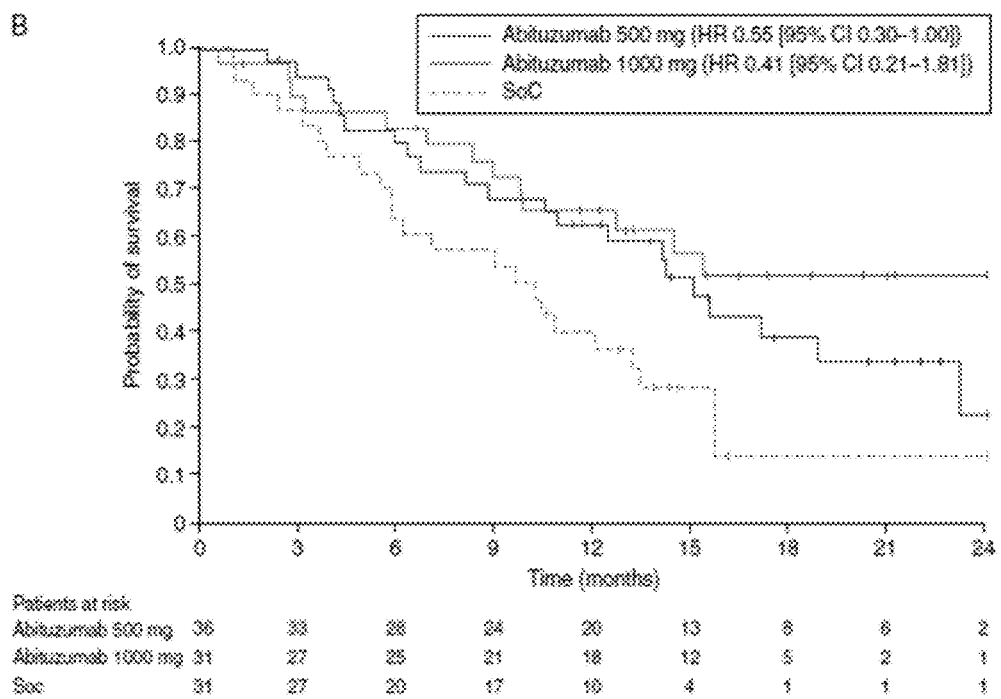
FIG. 3 shows an OS curve based on high αvβ6 expression and treated with Abituzumab+Cetuximab+Irinotecan versus Cetuximab+Irinotecan alone (SOC) in patients with both right and left-sided tumors (POSEIDON), where SoC is the lowest curve at 24 months; Abituzumab 500 mg is the median curve at 24 months; and Abituzumab 1000 mg is the highest curve at 24 months.

Biomarker Results:

The POSEIDON study included a pre-planned test for $\alpha v\beta 6$ expression by immunohistochemistry. High versus low $\alpha v\beta 6$ expression appeared to be a prognostic marker in these patients for survival and patients with a high $\alpha v\beta 6$ expression appeared to benefit from the treatment with Abituzumab (FIG. 3).

In order to identify a patient population that would benefit most from the addition of Abituzumab, further analysis were conducted. As high $\alpha v\beta 6$ expression is suggestive to be a negative prognostic factor for survival when expressed in the tumor, treatment effect of cetuximab+irinotecan alone seems to be limited. As in addition high $\alpha v\beta 6$ expression is being found to be a predictive factor for response to Abituzumab, it is postulated that Abituzumab as a $\alpha v\beta 6$ integrin inhibitor will result in longer PFS and OS in a subset of these patients.

Efficacy Results in Left-Sided Population with High $\alpha v\beta 6$ Expression (POSEIDON):

Our re-evaluation of the data of the POSEIDON study revealed that in ~73% of patients, the location of the tumor is found to have been on the left side of the colon and to be evenly distributed between the Abituzumab in combination with cetuximab+irinotecan and cetuximab+irinotecan alone groups. Based on the recommendation for left-sided tumor in RAS WT and/or KRAS WT mCRC by international guidelines (NCCN, ESMO 2017), further exploratory analysis was conducted on the POSEIDON study data to explore the treatment effect with Abituzumab in left-sided patients with high $\alpha v\beta 6$ expression, compared to right-sided CRC. Surprisingly, a very favorable treatment effect was observed in left-sided CRC patient population.

TABLE 2

Results of the POSEIDON study

| | High Histoscore | | | Low Histoscore | |
|---|---|---|---|---|---|
| | Abituzumab 1000 mg + Cetuximab + Irinotecan | Abituzumab 500 mg + Cetuximab + Irinotecan | Cetuximab + Irinotecan | Abituzumab 1000 mg + Cetuximab + Irinotecan | Cetuximab + Irinotecan |
| PFS months (n) | | | | | |
| All patients | 6.9 (31) | 5.6 (36) | 4.2 (26) | 4.9 (35) | 5.8 (34) |
| Right CRC | 2.6 (11) | 2.8 (6) | 4.2 (9) | 3.5 (8) | 4.2 (5) |
| Left CRC | 8.6 (20) | 5.6 (30) | 4.2 (22) | 5.4 (27) | 6.5 (29) |
| Objective Response Rate % (n) | | | | | |
| All patients | 35.5 (31) | 30.6 (36) | 16.1 (31) | 20.0 (35) | 32.4 (34) |
| Right CRC | 18.2 (11) | 0 (6) | 0 (9) | 12.5 (8) | 20.0 (5) |
| Left CRC | 45.0 (20) | 36.7 (30) | 22.7 (22) | 22.2 (27) | 34.5 (29) |

TABLE 2-continued

Results of the POSEIDON study

Overall Survival months (n)

| | | | | | |
|---|---|---|---|---|---|
| All patients | 20.6 (31) | 15.5 (36) | 10.2 (31) | 12.8 (35) | 15.9 (34) |
| Right CRC | 9.8 (11) | 5.1 (6) | 9.5 (9) | 8.6 (8) | 10.0 (5) |
| Left CRC | 25.6 (20) | 17.1 (30) | 10.2 (22) | 13.6 (27) | 15.9 (29) |

Hazard Ratio for OS

| Abituzumab | Population | HR | HR. 95CILL | HR.95CIUL | p- value |
|---|---|---|---|---|---|
| 500/1000 mg | Left/αvβ6 - above | 0.454 | 0.257 | 0.805 | 0.0068 |
| 500 mg | Left/αvβ6 - above | 0.527 | 0.284 | 0.976 | 0.0416 |
| 1000 mg | Left/αvβ6 - above | 0.357 | 0.171 | 0.746 | 0.0061 |

Left-Sided Colorectal Cancer

The terms "left-sided colorectal cancer" and "left-sided colon cancer" are known and understood in the art, including the respective localisation of the cancer or tumor, and can be differentiated from "right-sided colorectal cancer" or "right-sided colon cancer". According to the instant invention, methods of treating "left-sided colorectal cancer" and "left-sided colon cancer" are preferred.

To go into more detail, the proximal and distal segments of the colon are preferably deemed to have different embryologic origins. The segment extending from the cecum to the proximal two thirds of the transverse colon is preferably deemed to derive from the midgut. The segment comprising the distal third of the transverse colon to the upper anal canal is preferably deemed to derive from the hindgut. If the distal transverse colon it is considered as the boundary between the right colon and left colon, the right colon preferably includes the cecum, ascending colon, liver flexure, and transverse colon, and the left colon preferably includes the splenic flexure, descending colon and sigmoid colon. Based on these findings, we suggest that colorectal cancer can be divided into three distinct disease entities: cancer of the right colon, left colon and rectal cancer, see e.g.: Michal Mik, Maciej Berut, Lukasz Dziki, Radzislaw Trzcinski, Adam Dziki; Arch Med Sci 2017; 13, 1: 157-162, the disclosure of which is preferably incorporated herein by reference in its entirety.

More specifically, in the context of the instant invention, "left-sided colorectal cancer" and "left-sided colon cancer" is preferably that part of the colon, preferably including the rectum and more preferably excluding the rectum, which is defined by a natural anatomic separation line which is the colon flexure.

In the context of the instant invention, the left-sided colorectal cancer or left-sided colon cancer is defined to be cancer located in the tissue left of said colon flexure. Thus, in the context of the instant invention, cancer located right of the colon flexure, preferably including the transversum, is to be regarded as "right-sided colorectal cancer" or "right-sided colon cancer".

Methods for the actual diagnosis and/or localisation of the cancer or tumor as left-sided are known and understood in the art. Preferably, the localisation as left-sided is performed anatomically, optically or sensorically, preferably optically, e.g. explorative during surgery or via colonoscopy. However, imaging methods, including, but not limited to CT, MRT, MRI, X-ray, ultrasonics and medical ultrasound are likewise suitable for determining whether a human being, human patient or patient is having left-sided CRC and/or mCRC, or not. For further information see also the American Cancer Society Guideline for Colorectal Cancer Screening.

High αvβ6 Integrin Expression

Methods for the determination of high αvβ6 integrin expression in the context of CRC and/or mCRC are known and understood in the art. Known procedures include the determination of αvβ6 integrin expression via histological methods, such as immunohistochemistry, preferably using tumor tissue. Suitable such methods are known in the art and for example described in: Simon L. Goodman, Hans Juergen Grote and Claudia Wilm; Biology Open 1, 329-340 (2012), the disclosure of which is preferably included into this document by reference.

Integrin αvβ3, αvβ5, αvβ6, αvβ8 and pan-αv expression and especially αvβ6 integrin expression is preferably assessed using immunohistochemistry on formalin-fixed, paraffin-embedded tumour tissue, preferably as previously described in: Goodman S L, Grote H J, Wilm C. "Matched rabbit monoclonal antibodies against αv-series integrins reveal a novel αvβ3-LIBS epitope, and permit routine staining of archival paraffin samples of human tumors". Biol Open 2012; 1: 329-340, the disclosure of which is preferably incorporated herein by reference in its entirety.

Data on intensity and frequency of staining were used to calculate histoscores on a continuous scale of 0-300, as previously described in: Pirker R, Pereira J R, von Pawel J et al. "EGFR expression as a predictor of survival for first-line chemotherapy plus cetuximab in patients with advanced non-small cell lung cancer: analysis of data from the phase 3 FLEX study". Lancet Oncol 2012; 13: 33-42, the disclosure of which is preferably incorporated herein by reference in its entirety.

Preferably, the thus obtained immunohistochemically stained FFPE samples are evaluated pathologically. In general, the pathologist quantifies the predominant staining intensity, specifies the staining pattern and estimates the percentages of positively stained tumor tissue. Preferably, a semi-quantitative evaluation of the immunohistochemically stained tumor tissue the H-score classification is to be applied, preferably in accordance with the procedure described in McCarty K S Jr et al., 1985 as cited above.

Therefore, negative (0), weakly stained (1), moderately stained (2) and strongly stained (3) areas are preferably to be estimated as percentage of tumor tissue. Subsequently the respective histoscore (H-score) is preferably calculated as follows:

$$H\text{-score}=(\text{weak})\%+(\text{moderate})\%\times 2+(\text{strong})\%\times 3$$

The obtained histoscores are preferably classified as given below:

TABLE 3

| Histoscores | |
|---|---|
| H-score | Classification |
| 0-50 | negative |
| 51-100 | weak positive |
| 101-200 | moderate positive |
| 201-3011 | strong positive |

In the context of the instant invention, the αvβ6 integrin expression is to be classified as high, if declassification is at least weak positive, preferably if it is moderate positive and especially if it is strong positive.

Alternatively, an αvβ6 integrin expression above median level can preferably be also regarded as high αvβ6 integrin expression.

More preferably, for use according to the invention, high αvβ6 integrin expression is characterised by histoscores, preferably histoscores obtained as described herein and/or the literature cited herein in this regard, or his disc as obtained in analogy to the methods as described and/or cited herein, of higher than 60 (>60), preferably higher than 70 (>70), more preferably higher than 80 (>70), even more preferably higher than 90 (>90) and especially higher than 100 (>100). However, even higher histoscores are likewise preferred, such as >110, >120, >130, >140, >150, >160, >170, >180, >190 or >200.

However, histoscore of higher than 70 (>70) has proven in the POSEIDON Study to be a suitable threshold for fulfilling the criterion of "high αvβ6 integrin expression" in the context of Abituzumab treatment.

RAS Wild-Type and/or KRAS Wild-Type Status

The importance RAS testing in colorectal cancer and/or metastatic colorectal cancer and methods for its determination, preferably including, but not limited to for the determination of RAS wild-type and/or KRAS wild-type status are known and understood in the art, and e.g. described in: J Han J M Van Krieken, Etienne Rouleau, Marjolijn J. L. Ligtenberg, Nicola Normanno, Scott D. Patterson, Andreas Jung, Virchows Arch (2016) 468:383-396.

Suitable tests for determining RAS WT, KRAS WT and/or NRAS WT status in CRC and/or mCRC patients are worldwide commercially available and are performed in hospitals around the globe, and preferably have undergone EMA and/or FDA approval. Suitable tests and test procedures for determining RAS WT, KRAS WT and/or NRAS WT status are described in the Experimental Section herein.

Furthermore, N. Normanno, R. Esposito Abate, M. Lambiase, L. Forgione, C. Cardone, A. Iannaccone, A. Sacco, A. M. Rachiglio, E. Martinelli, D. Rizzi, S. Pisconti, M. Biglietto, R. Bordonaro, T. Troiani, T. P. Latiano, F. Giuliani, S. Leo, A. Rinaldi, E. Maiello, F. Ciardiello; Annals of Oncology 29: 112-118, 2018, J. Vidal et al., Annals of Oncology 28: 1325-1332, 2017, J. Grasselli et al., Annals of Oncology 28: 1294-1301, 2017, the disclosure of which is preferably incorporated herein by reference in their entirety, describe suitable alternative methods for determining RAS WT, KRAS WT and/or NRAS WT status.

In the context of the instant invention, RAS preferably includes KRAS and/or NRAS, and preferably both KRAS and NRAS. Especially preferably, for the treatments according to the invention comprising cetuximab, RAS preferably consists of KRAS and NRAS. The respective wild-type status has been found to be an important biomarker for at least some growth factor or growth factor receptor targeting monoclonal antibodies, including, but not limited to cetuximab and panitumumab. For some time, cetuximab efficacy has primarily be associated with KRAS wild-type status, but it is currently preferably also associated with RAS wild-type status. In contrast thereto, Panitumumab efficacy preferably has primarily be associated with NRAS wild-type status. However, Panitumumab efficacy can preferably also assessed by RAS and/or wild-type testing, see e.g. Rafael G. Amado, Michael Wolf, Marc Peeters, Eric Van Cutsem, Salvatore Siena, Daniel J. Freeman, Todd Juan, Robert Sikorski, Sid Suggs, Robert Radinsky, Scott D. Patterson, and David D. Chang, Clin Oncol 26:1626-1634 (2008), the disclosure of which is incorporated herein by reference in its entirety.

In addition, major guidelines recommend Cetuximab for treatment for first-line left-sided RAS WT mCRC (NCCN Guidelines version 2.2017 updates colon cancer; Arnold D, Cutsem E. V, Cervantes A, et al. Metastatic Colorectal Cancer: ESMO Clinical Practice Guidelines. Annals of Oncology. 2014; 25 (suppl 3): iii1-iii9).

The determination of RAS WT status, as preferably to be used according to the invention, preferably differs from determination of the KRAS WT status, e.g. as performed at the time of the conduct of the POSEIDON study, in that at that time only KRAS exon 2, and not exon 4 and NRAS exon 2-4 mutations (=RAS mutations) were excluded. Therefore, for methods of treatment according to the invention, the patients to be treated are preferably the RAS WT CRC/mCRC patients, rather than in KRAS WT CRC/mCRC patients. As a result of said RAS testing, patients with both KRAS exon 2-4 and NRAS exon 2-4 mutations (=RAS mutations) will be preferably excluded from the preferred patient subgroup to be treated according to the methods of the invention.

Thus, RAS wild-type testing will preferably exclude both KRAS mutated and NRAS mutated patients.

As a consequence, RAS wild-type status preferably comprises KRAS wild-type status and NRAS wild-type status, and more preferably is comprised of KRAS wild-type status and NRAS wild-type status.

Thus, in the context of the instant invention, RAS WT testing preferably includes KRAS WT testing and/or NRAS WT testing, and preferably both KRAS WT testing and NRAS WT testing. Especially preferably, for the treatments according to the invention comprising cetuximab, RAS WT testing preferably consists of KRAS WT testing and NRAS WT testing.

Thus, preferred subjects of the instant invention thus are:

[1] A method of treating colorectal cancer in humans, said method comprising administering Abituzumab to said humans, wherein said colorectal cancer is characterised by high αvβ6 integrin expression.

[2] A method of treating colorectal cancer in humans, said method comprising administering Abituzumab to said humans, wherein said colorectal cancer is left sided colorectal cancer.

[3] A method of treating left-sided colorectal cancer as described herein, preferably as described above and/or below, said method comprising administering Abituzumab to said humans, wherein said left-sided colorectal cancer is characterised by high αvβ6 integrin expression

[4] A method as described herein, preferably as described above and/or below, more preferably as described in the numbered sections above and/or below, and especially as described in one or more of sections numbered [1], [2] or [3], wherein said humans also receive at least one growth factor or growth factor receptor targeting monoclonal antibody, and/or chemotherapy.

[5] A method as described herein, preferably as described above and/or below, more preferably as described in the numbered sections above and/or below, and especially as described in one or more of sections numbered [1], [2], [3] and/or [4], wherein said colorectal cancer is stage II, stage III or stage IV colorectal cancer.

[6] A method as described herein, preferably as described above and/or below, more preferably as described in the numbered sections above and/or below, and especially as described in one or more of sections numbered [1], [2], [3], [4] and/or [5], wherein said colorectal cancer is metastatic colorectal cancer or left-sided metastatic colorectal cancer.

[7] A method as described herein, preferably as described above and/or below, more preferably as described in the numbered sections above and/or below, and especially as described in one or more of sections numbered [1], [2], [3], [4], [5] and/or [6], wherein said colorectal cancer is left-sided colorectal cancer or left-sided metastatic colorectal cancer, characterised by high αvβ6 integrin expression.

[8] A method as described herein, preferably as described above and/or below, more preferably as described in the numbered sections above and/or below, and especially as described in one or more of sections numbered [1] to [7], wherein said colorectal cancer is RAS wild-type and/or KRAS wild-type colorectal cancer.

[9] A method as described herein, preferably as described above and/or below, more preferably as described in the numbered sections above and/or below, and especially as described in one or more of sections numbered [1] to [8], wherein said colorectal cancer is RAS wild-type and/or KRAS wild-type left-sided colorectal cancer or RAS wild-type and/or KRAS wild-type left-sided metastatic colorectal cancer.

[10] A method as described herein, preferably as described above and/or below, more preferably as described in the numbered sections above and/or below, and especially as described in one or more of sections numbered [1] to [9], wherein said colorectal cancer is stage II, stage III or stage IV RAS wild-type and/or KRAS wild-type left-sided colorectal cancer or RAS wild-type and/or KRAS wild-type left-sided metastatic colorectal cancer, characterised by high αvβ6 integrin expression.

[11] A method as described herein, preferably as described above and/or below, more preferably as described in the numbered sections above and/or below, and especially as described in one or more of sections numbered [1] to [10], wherein said colorectal cancer is RAS wild-type and/or KRAS wild-type left-sided metastatic colorectal cancer characterised by high αvβ6 integrin expression.

[12] A method as described herein, preferably as described above and/or below, more preferably as described in the numbered sections above and/or below, and especially as described in one or more of sections numbered [1] to [11], wherein said left-sided colorectal cancer is newly diagnosed colorectal cancer.

[13] A method as described herein, preferably as described above and/or below, more preferably as described in the numbered sections above and/or below, and especially as described in one or more of sections numbered [1] to [12], wherein said method is applied in a first-line treatment setting.

[14] A method as described herein, preferably as described above and/or below, more preferably as described in the numbered sections above and/or below, and especially as described in one or more of sections numbered [4] to [13], wherein said method is applied in a concomitant treatment setting.

[15] A method as described herein, preferably as described above and/or below, more preferably as described in the numbered sections above and/or below, and especially as described in one or more of sections numbered [4] to [14], wherein said method is applied in an adjuvant treatment setting.

[16] A method as described herein, preferably as described above and/or below, more preferably as described in the numbered sections above and/or below, and especially as described in one or more of sections numbered [4] to [15], wherein said method is applied in a neoadjuvant treatment setting.

[17] A method as described herein, preferably as described above and/or below, more preferably as described in the numbered sections above and/or below, and especially as described in one or more of sections numbered [4] to [15], wherein said humans receive said at least one growth factor or growth factor receptor targeting monoclonal antibody and/or said optional chemotherapy concomitantly to said Abituzumab.

[18] A method as described herein, preferably as described above and/or below, more preferably as described in the numbered sections above and/or below, and especially as described in one or more of sections numbered [4] to [16], wherein said at least one growth factor or growth factor receptor targeting monoclonal antibody comprises cetuximab, bevacizumab and/or panitumumab.

[19] A method as described herein, preferably as described above and/or below, more preferably as described in the numbered sections above and/or below, and especially as described in one or more of sections numbered [4] to [18], wherein said at least one growth factor or growth factor receptor targeting monoclonal antibody is selected from the group consisting of cetuximab and bevacizumab.

[20] A method as described herein, preferably as described above and/or below, more preferably as described in the numbered sections above and/or below, and especially as described in one or more of sections numbered [5] to [18], wherein said chemotherapy comprises one or more compounds selected from the group consisting of irinotecan, fluorouracil (5-FU), or prodrugs thereof, preferably capecitabine and/or 5-fluorocytosine, tegafur/uracil (UFT), folinic acid (leucovorin), Oxaliplatin (Eloxatin), aflibercept, regorafenib, capecitabine, and the prodrugs thereof, and the salts and solvates thereof.

[21] A method as described herein, preferably as described above and/or below, more preferably as described in the numbered sections above and/or below, and especially as described in one or more of sections numbered [4] to [20], wherein said chemotherapy is administered according to a FOLFIRI protocol.

[22] A method as described herein, preferably as described above and/or below, more preferably as described in the numbered sections above and/or below, and especially as described in one or more of sections numbered [4] to [20], wherein said chemotherapy is administered according to a FOLFOX protocol.

[23] A method as described herein, preferably as described above and/or below, more preferably as described in the numbered sections above and/or below, and especially as described in one or more of sections numbered [4] to [22], wherein said chemotherapy comprises
  a) one or more compounds selected from irinotecan, fluorouracil (5-FU), and folinic acid (leucovorin), and the prodrugs thereof,
  or
  b) one or more compounds selected from oxaliplatin (e.g. eloxatin), fluorouracil (5-FU), and folinic acid (e.g. leucovorin), and the prodrugs thereof, and the salts and solvates thereof.

[24] A method as described herein, preferably as described above and/or below, more preferably as described in the numbered sections above and/or below, and especially as described in one or more of sections numbered [1] to [23], wherein said Abituzumab is administered to said humans in an amount of 375 mg to 750 mg per week, in an amount of 750 mg to 1500 mg every second week or in an amount of 1500 mg to 3000 mg per month.

[25] A method as described herein, preferably as described above and/or below, more preferably as described in the numbered sections above and/or below, and especially as described in one or more of sections numbered [1] to [24], wherein said Abituzumab is administered to said humans in an amount of about 500 mg per week, in an amount of about 1000 mg every second week or in an amount of about 2000 mg per month.

[26] A method as described herein, preferably as described above and/or below, more preferably as described in the numbered sections above and/or below, and especially as described in one or more of sections numbered [1] to [25], wherein said Abituzumab is administered to said humans for at least 6 cycles, preferably at least 8 cycles, more preferably at least 10 cycles and especially at least 12 cycles, each cycle having a duration of about 1 week, of about 2 weeks, of about 4 weeks or of about a month.

[27] A method as described herein, preferably as described above and/or below, more preferably as described in the numbered sections above and/or below, and especially as described in one or more of sections numbered [1] to [26], wherein said Abituzumab is administered to said humans for at least 6 cycles, preferably at least 8 cycles, more preferably at least 10 cycles and especially at least 12 cycles, each cycle having a duration of about 2 weeks.

[28] A method as described herein, preferably as described above and/or below, more preferably as described in the numbered sections above and/or below, and especially as described in one or more of sections numbered [4] to [27], wherein said at least one growth factor or growth factor receptor targeting monoclonal antibody is administered to said humans in an amount of 75 mg to 1000 mg per week, 150 mg to 2000 mg every second week, or in an amount of 300 mg to 4000 mg per month.

[29] A method as described herein, preferably as described above and/or below, more preferably as described in the numbered sections above and/or below, and especially as described in one or more of sections numbered [18] to [28], wherein said cetuximab is administered to said humans in an amount of about 150 mg/m$^2$ to 550 mg/m$^2$ per week, 300 mg/m$^2$ to 1100 mg/m$^2$ every second week, or in an amount of about 600 mg/m$^2$ to per 2200 mg/m$^2$ per month.

[30] A method as described herein, preferably as described above and/or below, more preferably as described in the numbered sections above and/or below, and especially as described in one or more of sections numbered [18] to [29], wherein said Cetuximab is administered to said humans for at least 6 cycles, preferably at least 8 cycles, more preferably at least 10 cycles and especially at least 12 cycles, each cycle having a duration of about 1 week, of about 2 weeks, of about 4 weeks, or of about a month.

[31] A method as described herein, preferably as described above and/or below, more preferably as described in the numbered sections above and/or below, and especially as described in one or more of sections numbered [18] to [30], wherein said Cetuximab is administered to said humans for at least 6 cycles, preferably at least 8 cycles, more preferably at least 10 cycles and especially at least 12 cycles, each cycle having a duration of about 2 weeks, wherein said Cetuximab is administered to said humans every week or every second week.

[32] A method as described herein, preferably as described above and/or below, more preferably as described in the numbered sections above and/or below, and especially as described in one or more of sections numbered [18] to [31], wherein said Cetuximab is administered to said humans for at least 6 cycles, preferably at least 8 cycles, more preferably at least 10 cycles and especially at least 12 cycles, each cycle having a duration of about 2 weeks, wherein said Cetuximab is administered to said humans either
  a) in an amount of about 500 mg/m$^2$ during each cycle, and preferably at the beginning of each cycle,
  or
  b) in an amount of about 400 mg/m$^2$ at the beginning of the first week of each cycle and in an amount of about 250 mg/m$^2$ at the beginning of the second week of each cycle.

[33] A method as described herein, preferably as described above and/or below, more preferably as described in the numbered sections above and/or below, and especially as described in one or more of sections numbered [18] to [28], wherein said bevacizumab is administered to said humans in an amount of about 1 mg/kg to 10 mg/kg per week, 3 mg/kg to 15 mg/kg every second week, or in an amount of about 6 mg/kg to per 30 mg/kg per month.

[34] A method as described herein, preferably as described above and/or below, more preferably as described in the numbered sections above and/or below, and especially as described in one or more of sections numbered [18] to [28] and [33], wherein said bevacizumab is administered to said humans for at least 6 cycles, preferably at least 8 cycles, more preferably at least 10 cycles and especially at least 12 cycles, each cycle having a duration of about 1 week, of about 2 weeks, of about 4 weeks, or of about a month.

[35] A method as described herein, preferably as described above and/or below, more preferably as described in the numbered sections above and/or below, and especially as described in one or more of sections numbered [18] to [28] and [33] to [34], wherein said bevacizumab is administered to said humans for at least 6 cycles, preferably at least 8 cycles, more preferably at least 10 cycles and especially at least 12 cycles, each cycle having a duration of about 2 weeks, wherein said bevacizumab is administered to said humans every week or every second week.

[36] A method as described herein, preferably as described above and/or below, more preferably as described in the numbered sections above and/or below, and especially as described in one or more of sections numbered [18] to [28] and [33] to [35], wherein said bevacizumab is administered to said humans for at least 6 cycles, preferably at least 8 cycles, more preferably at least 10 cycles and especially at least 12 cycles, each cycle having a duration of about 2 weeks, wherein said bevacizumab is administered to said humans either
- a) in an amount of 3 mg/kg to 15 mg/kg or in an amount of 5 mg/kg to 10 mg/kg during each cycle, and preferably at the beginning of each cycle, or
- b) in an amount of about 7.5 mg/kg during each cycle, and preferably at the beginning of each cycle.

[37] A method as described herein, preferably as described above and/or below, more preferably as described in the numbered sections above and/or below, and especially as described in one or more of sections numbered [18] to [28], wherein said panitumumab is administered to said humans in an amount of about 1 mg/kg to 10 mg/kg per week, 3 mg/kg to 15 mg/kg every second week, or in an amount of about 6 mg/kg to per 30 mg/kg per month.

[38] A method as described herein, preferably as described above and/or below, more preferably as described in the numbered sections above and/or below, and especially as described in one or more of sections numbered [18] to [28] and [37], wherein said panitumumab is administered to said humans for at least 6 cycles, preferably at least 8 cycles, more preferably at least 10 cycles and especially at least 12 cycles, each cycle having a duration of about 1 week, of about 2 weeks, of about 4 weeks, or of about a month.

[39] A method as described herein, preferably as described above and/or below, more preferably as described in the numbered sections above and/or below, and especially as described in one or more of sections numbered [18] to [28] and [37] to [38], wherein said panitumumab is administered to said humans for at least 6 cycles, preferably at least 8 cycles, more preferably at least 10 cycles and especially at least 12 cycles, each cycle having a duration of about 2 weeks, wherein said panitumumab is administered to said humans every week or every second week.

[40] A method as described herein, preferably as described above and/or below, more preferably as described in the numbered sections above and/or below, and especially as described in one or more of sections numbered [18] to [28] and [37] to [39], wherein said panitumumab is administered to said humans for at least 6 cycles, preferably at least 8 cycles, more preferably at least 10 cycles and especially at least 12 cycles, each cycle having a duration of about 2 weeks, wherein said panitumumab is administered to said humans either
- a) in an amount of 3 mg/kg to 15 mg/kg or in an amount of 4 mg/kg to 10 mg/kg during each cycle, and preferably at the beginning of each cycle, or
- b) in an amount of about 6 mg/kg during each cycle, and preferably at the beginning of each cycle.

[41] A method as described herein, preferably as described above and/or below, more preferably as described in the numbered sections above and/or below, and especially as described in one or more of sections numbered [29] to [32] and/or sections numbered numbered [37] to [40], wherein said colorectal cancer is RAS wild-type and/or KRAS wild-type colorectal cancer.

[42] A method as described herein, preferably as described above and/or below, more preferably as described in the numbered sections above and/or below, and especially as described in one or more of sections numbered [29] to [32] and/or sections numbered [37] to [40], wherein said colorectal cancer is RAS wild-type and/or KRAS wild-type left-sided colorectal cancer or RAS wild-type and/or KRAS wild-type left-sided metastatic colorectal cancer.

[43] A method as described herein, preferably as described above and/or below, more preferably as described in the numbered sections above and/or below, and especially as described in one or more of sections numbered [4] to [42], wherein said chemotherapy is administered to said humans for at least 6 cycles, preferably at least 8 cycles, more preferably at least 10 cycles and especially at least 12 cycles, each cycle having a duration of about 2 weeks, wherein
- a) said irinotecan, and/or a prodrug, a salt and/or a solvate thereof,
- b) said folinic acid, and/or a prodrug, a salt and/or a solvate thereof, and/or
- c) said fluorouracil (5-FU), and/or a prodrug, a salt and/or a solvate thereof, is administered to said humans during each cycle, preferably at the beginning of each cycle and/or at the beginning of each week of each cycle.

[44] A method as described herein, preferably as described above and/or below, more preferably as described in the numbered sections above and/or below, and especially as described in one or more of sections numbered [4] to [43], wherein said humans also receive chemotherapy, said chemotherapy comprising,
- a) irinotecan, and/or a prodrug, a salt and/or a solvate thereof, in an amount of 50 mg/m$^2$ to 150 mg/m$^2$ per week, in an amount of 100 mg/m$^2$ to 300 mg/m$^2$ every second week, or in an amount of 200 mg/m$^2$ to 600 mg/m$^2$ per month,
- b) folinic acid (racemic), and/or a prodrug, a salt and/or a solvate thereof, in an amount of 150 mg/m$^2$ to 250 mg/m$^2$ per week, in an amount of 300 mg/m2 to 500 mg/m$^2$ every second week, or in an amount of 600 mg/m$^2$ to 1000 mg/m$^2$ per month, and/or
- c) fluorouracil (5-FU), and/or a prodrug, a salt and/or a solvate thereof, in an amount of 150 mg/m$^2$ to 250 mg/m$^2$ per week, in an amount of 300 mg/m$^2$ to 500 mg/m$^2$ every second week, or in an amount of 600 mg/m$^2$ to 1000 mg/m$^2$ per month.

[45] A method as described herein, preferably as described above and/or below, more preferably as described in the numbered sections above and/or below, and especially as described in one or more of sections numbered [4] to [44], wherein said humans also receive chemotherapy, said chemotherapy comprising,
- a) irinotecan, and/or a prodrug, a salt and/or a solvate thereof, in an amount of 50 mg/m$^2$ to 150 mg/m$^2$ per week, in an amount of 100 mg/m$^2$ to 300 mg/m$^2$ every second week, or in an amount of 200 mg/m$^2$ to 600 mg/m$^2$ per month,
- b) folinic acid (racemic), and/or a prodrug, a salt and/or a solvate thereof, in an amount of 150 mg/m$^2$ to 250 mg/m$^2$ per week, in an amount of 300 mg/m$^2$ to 500 mg/m$^2$ every second week, or in an amount of 600 mg/m$^2$ to 1000 mg/m$^2$ per month, and/or
- c) fluorouracil (5-FU), and/or a prodrug, a salt and/or a solvate thereof, in an amount of 1000 mg/m$^2$ to 3000 mg/m$^2$ per week, in an amount of 2000 mg/m$^2$ to 6000 mg/m$^2$ every second week, or in an amount of 4000 mg/m$^2$ to 12000 mg/m$^2$ per month, preferably in an amount of 2000 mg/m$^2$ to 3200 mg/m$^2$ every second week.

[46] A method as described herein, preferably as described above and/or below, more preferably as described in the numbered sections above and/or below, and especially as described in one or more of sections numbered [4] to [45], wherein said chemotherapy is administered to said humans for at least 6 cycles, preferably at least 8 cycles, more preferably at least 10 cycles and especially at least 12 cycles, each cycle having a duration of about 1 week, of about 2 weeks, of about 4 weeks, or of about a month.

[47] A method as described herein, preferably as described above and/or below, more preferably as described in the numbered sections above and/or below, and especially as described in one or more of sections numbered [4] to [42], wherein said chemotherapy is administered to said humans for at least 6 cycles, preferably at least 8 cycles, more preferably at least 10 cycles and especially at least 12 cycles, each cycle having a duration of about 2 weeks, wherein
 a) said oxaliplatin, and/or a prodrug, a salt and/or a solvate thereof,
 b) said folinic acid, and/or a prodrug, a salt and/or a solvate thereof, and/or
 c) said fluorouracil (5-FU), and/or a prodrug, a salt and/or a solvate thereof, is administered to said humans during each cycle, and preferably at the beginning of each cycle.

[48] A method as described herein, preferably as described above and/or below, more preferably as described in the numbered sections above and/or below, and especially as described in one or more of sections numbered [4] to [42] and [47], wherein said humans also receive chemotherapy, said chemotherapy comprising,
 a) oxaliplatin, and/or a prodrug, a salt and/or a solvate thereof, in an amount of 20 mg/m$^2$ to 120 mg/m$^2$ per week, in an amount of 40 mg/m$^2$ to 240 mg/m$^2$ every second week, or in an amount of 80 mg/m$^2$ to 480 mg/m$^2$ per month,
 b) folinic acid (racemic), and/or a prodrug, a salt and/or a solvate thereof, in an amount of 150 mg/m$^2$ to 250 mg/m$^2$ per week, in an amount of 300 mg/m$^2$ to 500 mg/m$^2$ every second week, or in an amount of 600 mg/m$^2$ to 1000 mg/m$^2$ per month, and/or
 c) 5-FU, and/or a prodrug, a salt and/or a solvate thereof, in an amount of 150 mg/m2 to 250 mg/m$^2$ per week, in an amount of 300 mg/m$^2$ to 500 mg/m$^2$ every second week, or in an amount of 600 mg/m$^2$ to 1000 mg/m$^2$ per month.

[49] A method as described herein, preferably as described above and/or below, more preferably as described in the numbered sections above and/or below, and especially as described in one or more of sections numbered [4] to [42] and [47] to [48], wherein said humans also receive chemotherapy, said chemotherapy comprising,
 a) oxaliplatin, and/or a prodrug, a salt and/or a solvate thereof, in an amount of 20 mg/m$^2$ to 120 mg/m$^2$ per week, in an amount of 40 mg/m$^2$ to 240 mg/m$^2$ every second week, or in an amount of 80 mg/m$^2$ to 480 mg/m$^2$ per month,
 b) folinic acid (racemic), and/or a prodrug, a salt and/or a solvate thereof, in an amount of 150 mg/m$^2$ to 250 mg/m$^2$ per week, in an amount of 300 mg/m$^2$ to 500 mg/m$^2$ every second week, or in an amount of 600 mg/m$^2$ to 1000 mg/m$^2$ per month, and/or
 c) 5-FU, and/or a prodrug, a salt and/or a solvate thereof, in an amount of 1000 mg/m$^2$ to 3000 mg/m$^2$ per week, in an amount of 2000 mg/m$^2$ to 6000 mg/m$^2$ every second week, or in an amount of 4000 mg/m$^2$ to 12000 mg/m$^2$ per month, preferably in an amount of 2000 mg/m$^2$ to 3200 mg/m$^2$ every second week.

[50] A method as described herein, preferably as described above and/or below, more preferably as described in the numbered sections above and/or below, and especially as described in one or more of sections numbered [4] to [42] and [47] to [49], wherein said chemotherapy is administered to said humans for at least 6 cycles, preferably at least 8 cycles, more preferably at least 10 cycles and especially at least 12 cycles, each cycle having a duration of about 1 week, of about 2 weeks, of about 4 weeks, or of about a month.

[51] A method as described herein, preferably as described above and/or below, more preferably as described in the numbered sections above and/or below, and especially as described in one or more of sections numbered [4] to [42] and [47] to [50], wherein said chemotherapy is administered to said humans for at least 6 cycles, preferably at least 8 cycles, more preferably at least 10 cycles and especially at least 12 cycles, each cycle having a duration of about 2 weeks, wherein
 a) said oxaliplatin, and/or a prodrug, a salt and/or a solvate thereof,
 b) said folinic acid, and/or a prodrug, a salt and/or a solvate thereof, and/or
 c) said 5-FU, and/or a prodrug, a salt and/or a solvate thereof, is administered to said humans during each cycle, and preferably at the beginning of each cycle.

[52] A method as described herein, preferably as described above and/or below, more preferably as described in the numbered sections above and/or below, and especially as described in one or more of sections numbered [1] to [51], wherein the primary tumor is located in the colon.

[53] A method as described herein, preferably as described above and/or below, more preferably as described in the numbered sections above and/or below, and especially as described in one or more of sections numbered [1] to [52], wherein the primary tumor is located in the left side of the colon.

[54] A method for the treatment of RAS wild-type and/or KRAS wild-type left-sided metastatic colorectal cancer (mCRC) in patients with high αvβ6 integrin expression, said method comprising administering to said patient Abituzumab in combination with cetuximab and/or FOLFIRI.

[55] A method for the treatment of RAS wild-type left-sided metastatic colorectal cancer (mCRC) in patients with high αvβ6 integrin expression said method comprising administering to said patient Abituzumab in combination with cetuximab and FOLFIRI.

[56] A method for the treatment of RAS wild-type and/or KRAS wild-type left-sided metastatic colon cancer in patients with high αvβ6 integrin expression, said method comprising administering to said patient Abituzumab in combination with cetuximab and/or FOLFIRI.

[57] A method for the treatment of RAS wild-type and/or KRAS wild-type left-sided metastatic colon cancer or metastatic colorectal cancer in patients with high αvβ6 integrin expression, said method comprising administering to said patient Abituzumab in combination with cetuximab and/or irinotecan.

[58] A method for the treatment of RAS wild-type left-sided metastatic colon cancer or metastatic colorectal cancer in patients with high αvβ6 integrin expression, said method comprising administering to said patient Abituzumab in combination with cetuximab and irinotecan, preferably in combination with folinic acid and/or 5-FU.

[59] The method according to one or more of sections numbered numbered [54] to [58], wherein said treatment is a first-line treatment.

[60] The method according to one or more of sections numbered numbered [54] to [59], wherein the metastatic colon cancer and/or metastatic colorectal cancer to be treated is Stage III and/or Stage IV cancer.

[61] The method according to one or more of sections numbered [54] to [60], wherein said medicament is to be administered to a patient in a manner that the amount of Abituzumab administered is about 1000 mg every second week or about 2000 mg per month.

[62] The method according to one or more of sections numbered [54] to [61], wherein said patients with high αvβ6 integrin expression are characterised by a αvβ6 integrin Histoscore of higher than 70, preferably higher than 80, more preferably higher than 90 and especially higher than 100, higher than 120 or higher than 150.

[63] The method according one or more of sections numbered [54] to [62], wherein said treatment is administered for at least 6, at least 8, at least 10 or at least 12 cycles, each cycle consisting of two weeks or about two weeks.

[64] The method according to one or more of sections numbered [54] to [63], wherein said Abituzumab, said cetuximab and/or said FOLFIRI is to be administered to said patients every second week, preferably in cycles of two weeks or about two weeks.

[65] The method according to one or more sections numbered [54] to [64], wherein said method is further defined as described in one or more sections numbered [1] to [53].

[65] The method according to one or more of sections numbered [1] to [64], wherein the humans or patients to be treated with Abituzumab are characterised by high αvβ6 integrin expression, preferably quantified by a αvβ6 integrin Histoscore of higher than 70, preferably higher than 80, more preferably higher than 90 and especially higher than 100, higher than 120 or higher than 150, wherein said Histoscore is determined by immunohistochemistry performed according to Simon L. Goodman, Biology Open 1, 329-340 (2012), and Histoscore classification performed according to McCarty Jr K S, Arch Pathol Lab Med 109: 716-721 (1985).

Thus, a preferred subject of the instant invention is the use of Abituzumab in the treatment of colorectal cancer, preferably colorectal cancer in left-sided CRC and/or mCRC patients with high αvβ6 expression, preferably patients receiving first-line treatment. Especially preferred is the use of Abituzumab in the treatment of colorectal cancer in combination with at least one growth factor or growth factor receptor targeting monoclonal antibody, preferably selected from the group consisting of cetuximab and panitumumab, in RAS Wild-Type (WT) and/or KRAS Wild-Type CRC and/or mCRC patients.

Also especially preferred is the use of Abituzumab, preferably as described above and/below, in combination with the recommended standards of care (SOC) for colorectal cancer and especially the recommended standards of care (SOC) treatment regimen, preferably selected from the group consisting of the recommended standards of care (SOC) treatment regimen
  i) for the treatment of RAS WT CRC and/or mCRC,
  ii) for the treatment of KRAS WT CRC and/or mCRC,
  iii) for the treatment of left-sided RAS WT CRC and/or mCRC,
  iv) for the treatment of left-sided KRAS WT CRC and/or mCRC,
  v) for the treatment of first-line left-sided RAS WT CRC and/or mCRC, and
  vi) for the treatment of first-line left-sided KRAS WT CRC and/or mCRC, that preferably include cetuximab or panitumumab, more preferably cetuximab, optionally in combination with FOLFIRI or FOLFOX, preferably for FOLFIRI. These treatment options are well established, established, especially in first-line RAS WT and/or KRAS WT CRC and/or mCRC, preferably in first-line RAS WT and/or KRAS WT mCRC, and, according to most recent analysis, especially preferred in left-sided CRC and/or mCRC, an even more preferred in left-sided CRC and/or mCRC.

In addition, major guidelines recommend this treatment i.a. for first-line left-sided RAS WT and/or KRAS WT mCRC (reference NCCN guideline) 1, ESMO guideline12).

The use of Abituzumab as described above and/or below and the methods of treatment according to the invention is especially preferred with regard to humans or human patients having confirmed RAS WT status. This patient group preferably differs from the humans or human patients with confirmed KRAS WT status, e.g. the humans or human patients treated in the POSEIDON study, insofar that only KRAS exon 2, and not exon 4 and NRAS exon 2-4 mutations (=RAS mutations) were excluded. Therefore, RAS WT CRC patients are more preferred to be treated according to the instant invention than KRAS WT CRC patients. Thus, patients with KRAS exon 2-4 and NRAS exon 2-4 mutations (=RAS mutations) are not part of the most preferred population of humans or human patients to be treated according to the invention. In addition, humans or human patients showing BRAF mutations in CRC are preferably deemed to be subset of CRC patients with a poor outcome which preferably require a different treatment approach. However, BRAF mutations are deemed to occur in right-sided CRC.

Thus, synergy of the methods according to the invention is preferably deemed to be established, especially with regard to methods according to the invention comprising Abituzumab+cetuximab+irinotecan, especially in humans or human patients with high αvβ6 integrin expression.

Thus, especially preferred according to the invention are methods of treating CRC and/or mCRC, preferably mCRC, preferably as described herein, wherein the selection of the backbone treatment is irinotecan based chemotherapy, preferably FOLFIRI, especially for first-line treatment. Furthermore, cetuximab+FOLFIRI is recommended as SOC by international guidelines for CRC and/or mCRC and especially recommended as SOC for the treatment of left-sided RAS WT mCRC. Preferably, the selection of the backbone treatment is driven by the tumor biology, especially in these first-line patients. Especially preferred according to the invention are methods of treating CRC and/or mCRC, preferably mCRC, as described herein that comprise the addition of 5-FU to the treatment regimen. Thus, especially preferred in the context of the instant invention are treatment regimen comprising Abituzumab added to cetuximab and FOLFIRI, preferably including 5-FU.

Backbone treatments comprising cetuximab and/or FOLFOX, or backbone treatments comprising bevacizumab, optionally in combination FOLFIRI or FOLFOX, are also preferred.

In methods of treatment or uses in the treatment described herein, Abituzumab is preferably administered to said humans, humans patients, or patients in an amount of at least 250 mg per week, in an amount of at least 500 mg every second week, or in an amount of at least 1000 mg per month. Abituzumab is preferably administered to said humans, humans patients, or patients in a maximum amount of 1000 mg or less per week, in a maximum amount of 2000 mg or less every second week, or in a maximum amount of 4000 mg or less per month. Preferably, Abituzumab is administered according to a so-called "flat dosing" scheme, which means that every human (being), human patient or just patient receives a defined amount or dose of Abituzumab, independently of body weight or body surface, or the like.

If not explicitly defined otherwise, administration of Abituzumab preferably means the administration of Abituzumab to a human (being)/humans, a human patient or just patient, and the amounts given with respect thereto are preferably amounts per human (being), per human patient or just per patient. The same preferably applies to all active ingredients, active principles or medicaments in the context of the methods of treatment, the medical uses and/or treatment regimens according to the invention described herein.

More preferably, Abituzumab is administered in an amount of 375 mg to 750 mg per week, in an amount of 750 mg to 1500 mg every second week or in an amount of 1500 mg to 3000 mg per month.

Even more preferably, Abituzumab is administered in an amount of 450 mg to 550 mg per week, in an amount of 900 mg to 1100 mg every second week or in an amount of 1800 mg to 2200 mg per month.

Typically, oncologic treatments are repeated within defined time intervals, which intervals are preferably called "cycles". The term "cycle" or "cycles" is known and understood in the art. Typically, a cycle is a time interval of one or more weeks, preferably one week, two weeks, three weeks or four weeks, after which basically the same treatment is repeated with regard to the specific human being, human patient or just patient. According to the invention, a cycle preferably has a duration of two weeks or about two weeks, especially with regard to the administration of Abituzumab.

Even more preferably, Abituzumab is administered in an amount of 900 mg to 1100 mg per cycle, each cycle preferably consisting of two weeks or about two weeks. Preferably, said Abituzumab is administered at the beginning of each cycle, preferably on day 1 or day 2 of each cycle, more preferably day 1 of each cycle.

Especially preferably, Abituzumab is administered in an amount of about 1000 mg per cycle, each cycle preferably consisting of two weeks or about two weeks. Preferably, said Abituzumab is administered at the beginning of each cycle, preferably on day 1 or day 2 of each cycle, more preferably day 1 of each cycle.

Especially preferably, Abituzumab is administered to a patient in an amount (flat dose) of about 1000 mg per cycle, each cycle preferably consisting of two weeks or about two weeks. Preferably, said Abituzumab is administered at the beginning of each cycle, preferably on day 1 or day 2 of each cycle, more preferably day 1 of each cycle.

Preferably, Abituzumab is administered in combination with at least one growth factor or growth factor receptor targeting monoclonal antibody, and/or chemotherapy. Growth factor or growth factor receptor targeting monoclonal antibodies are known in the art. Preferred growth factor or growth factor receptor targeting monoclonal antibodies comprise cetuximab, bevacizumab and/or panitumumab. preferably, said growth factor or growth factor receptor targeting monoclonal antibodies are selected from the group of cetuximab, bevacizumab and/or panitumumab, of which cetuximab is especially preferred.

Cetuximab as such and suitable dose regimen of administering Cetuximab are known in the art. Preferably, cetuximab is administered in an amount of about 150 mg/m$^2$ to 550 mg/m$^2$ per week, 300 mg/m$^2$ to 1100 mg/m$^2$ every second week, or in an amount of about 600 mg/m$^2$ to per 2200 mg/m$^2$ per month.

More preferably, cetuximab is administered in an amount of about 200 mg/m$^2$ to 350 mg/m$^2$ per week, 400 mg/m$^2$ to 700 mg/m$^2$ every second week, or in an amount of about 800 mg/m$^2$ to 1400 mg/m$^2$ per month.

Even more preferably, cetuximab is administered in an amount of 450 mg/m$^2$ to 750 mg/m$^2$ per cycle, each cycle preferably consisting of two weeks or about two weeks.

Preferably, said cetuximab is administered at the beginning of each cycle of two weeks, preferably on day 1 or day 2 of each cycle, more preferably day 1 of each cycle (consisting of two weeks or about two weeks), or alternatively, the amount of cetuximab to be administered is divided into two portions, one portion given at the beginning of the first week of each cycle, and the second portion given at the beginning of the second week of each cycle. Preferably, the portions are divided either in a ratio of about 1:1 or in a ratio between 2:1 and 4:1, and especially preferably in a ratio of about 3:2. Especially preferably, said cetuximab is either administered in an amount of about 500 mg/m$^2$ per cycle (consisting of two weeks or about two weeks), preferably on day 1 or day 2 of each cycle, more preferably day 1 of each cycle, or it is administered in an amount of about 650 mg/m$^2$ per cycle, the first about 400 mg/m$^2$ at the beginning of the first week of each cycle, and the residual about 250 mg/m$^2$ at the beginning of the second week (and last week) of each cycle.

Preferably, said Abituzumab is administered in combination with FOLFIRI. Even more preferably, said Abituzumab is administered in combination with said cetuximab and FOLFIRI. FOLFIRI comprises folinic acid (leucovorin), fluorouracil (5-FU), and irinotecan, and/or a prodrug, a salt and/or a solvate thereof, or more preferably consists of folinic acid (leucovorin), fluorouracil (5-FU), and irinotecan, and/or a prodrug, a salt and/or a solvate thereof.

FOLFIRI as such and also its administration is known and understood in the art. Preferably, FOLFIRI is administered in accordance with the FOLFIRI protocol. Even more preferably, FOLFIRI is administered us as described below:

Folinic acid (preferably racemic follinic acid), and/or a prodrug, a salt and/or a solvate thereof, as such and suitable dose is regimen for it are known in the art. Preferably, it is administered in an amount of 150 mg/m$^2$ to 250 mg/m$^2$ per week, in an amount of 300 mg/m$^2$ to 500 mg/m$^2$ every second week, or in an amount of 600 mg/m$^2$ to 1000 mg/m$^2$ per month. More preferably, it is administered in an amount of 300 mg/m$^2$ to 500 mg/m$^2$ per cycle, each cycle preferably consisting of two weeks or about two weeks. Even more preferably it is administered in an amount of about 400 mg/m$^2$ per cycle, each cycle preferably consisting of two weeks or about two weeks. Preferably, it is administered at the beginning of each cycle, preferably on day 1 or day 2 of each cycle, more preferably day one of each cycle, said cycle consisting of two weeks or about two weeks.

Fluorouracil (5-FU), and/or a prodrug, a salt and/or a solvate thereof, as such and suitable dose regimen for its administration are known in the art. Preferably, it is administered in an amount of 1000 mg/m$^2$ to 3000 mg/m$^2$ per week, in an amount of 2000 mg/m$^2$ to 6000 mg/m$^2$ every second week, or in an amount of 4000 mg/m$^2$ to 12000 mg/m$^2$ per month, more preferably in an amount of 2000 mg/m$^2$ to 3200 mg/m$^2$ every second week. Even more preferably, it is administered in an amount of 1200 mg/m$^2$ to 1500 mg/m$^2$ per week, in an amount of 2400 mg/m$^2$ to 3000 mg/m² every second week, or in an amount of 4800 mg/m² to 6000 mg/m² per month, more preferably in an amount of 2000 mg/m² to 3000 mg/m² every second week. even more preferably, it is administered in an amount of about 2000 mg/m² or of about 2800 mg/m² per cycle, each cycle preferably consisting of two weeks or about two weeks. Preferably, it is administered at the beginning of each cycle of two weeks, preferably on day 1 and/or day 2 of each cycle. More preferably, it is administered as a i.V. bolus of about 400 mg/m² on day 1 and as one or more additional intravenous infusions of in total about 2400 mg/m² on day 1 and/or day 2 or alternatively as a continuous infusion of 2400 mg/m² on day 1 and day 2.

Irinotecan, and/or a prodrug, a salt and/or a solvate thereof, as such and suitable dose regimen for its administration are known in the art. Preferably, it is administered in an amount of 50 mg/m² to 150 mg/m² per week, in an amount of 100 mg/m² to 300 mg/m² every second week, or in an amount of 200 mg/m² to 600 mg/m² per month, more preferably in an amount of 80 mg/m² to 100 mg/m² per week, in an amount of 160 mg/m² to 200 mg/m² every second week, or in an amount of 320 mg/m² to 400 mg/m² per month. Even more preferably, it is administered in an amount of 160 mg/m² to 200 mg/m² per cycle, each cycle preferably consisting of two weeks or about two weeks. Preferably, it is administered at the beginning of each cycle, preferably on day 1 or day 2 of each cycle, more preferably day 1 of each cycle, said cycle consisting of two weeks or about two weeks.

Build on the newly observed efficacy of the 1000 mg Abituzumab dose without significant increase of toxicity, with the largest number of patients tested, the 1000 mg dose is the most preferred one, preferably given in 2-weekly administration intervals, preferably also referred to as cycles of two weeks or about two weeks. In addition, with said 1000 mg dose at steady state the serum trough concentration of Abituzumab is constantly above the IC99 of the non-linear clearance pathway during 2-weekly administration intervals.

Preferably, said 1000 mg Abituzumab dose, preferably administered IV, is given in combination with cetuximab+FOLFIRI, preferably also administered IV, to patients with RAS WT, left-sided, mCRC with high αvβ6 integrin expression, more preferably to newly diagnosed patients with RAS WT, left-sided, mCRC with high αvβ6 integrin expression, and especially those who are eligible for first-line treatment.

In the context of cetuximab administration, confirmation of RAS WT or KRAS WT mCRC by the local laboratory is highly recommended before cetuximab administration. Determination of a high αvβ6 integrin expression by the central laboratory is especially preferred, and preferably done at screening.

Preferably, patients with confirmed high αvβ6 integrin expression and RAS WT or KRAS WT status, will be treated with Abituzumab 1000 mg (every second week=1 cycle) plus Cetuximab+FOLFIRI according to the Standard of Care protocol in this regard.

Preferably, treatment is continued for at least 6 cycles, more preferably at least 8 cycles and especially at least 10 cycles. Typically, not less than 6 or 8 cycles are administered. Typically, a maximum of about 20 cycles, preferably of about 18 cycles, of about 16 cycles, of about 14 cycles or about 12 cycles are performed. However, the number of cycles administered to each patient is in the sole discretion of the oncologist in charge.

Preferably, Abituzumab treatment according to the invention, added to SoC, and more preferably added to cetuximab+FOLFIRI, is superior to SoC, and more preferably superior to cetuximab+FOLFIRI alone with respect to Progression Free Survival (PFS), preferably to Progression Free Survival (PFS) by investigator.

Preferably, the methods of treatment according to the invention are superior to the treatment regimen according to prior art with respect to one or more of the following criteria, selected from the group consisting of: Overall Survival (OS), Objective Response Rate (ORR), Depth of Response (DPR) and Early Tumor Shrinkage (ETS) by investigator.

More preferably, the methods of treatment according to the invention are comparable to the treatment regimen according to prior art with respect to safety and tolerability, preferably even in view of the higher efficacy.

Thus, the methods treatment according to the invention preferably show favourable outcomes in one or more of the below given characteristics:

higher Overall Survival (OS), higher Objective Response Rate (ORR), higher Depth of Response (DPR) and Early Tumor Shrinkage (ETS).

higher likelihood of secondary resection rate with a potentially curative intent favourable Overall safety profile, e.g. and at least reasonable outcome in one or more of the following: frequency, severity and seriousness of AEs (including AEs with fatal outcome), frequency and nature of AEs leading to discontinuation, frequency and nature of clinically significant abnormal laboratory parameters and vital signs, frequency of anti-drug antibodies (binding and/or neutralizing).

In order to achieve the benefit of the treatments according to the invention and especially the preferred treatments according to the invention, the humans, human patients or patients preferably shall fulfil one or more, preferably two or more and especially three or more of the following criteria:

Evidence of metastatic colorectal cancer, preferably stage IV metastatic colorectal cancer, more preferably newly diagnosed metastatic colorectal cancer or newly diagnosed stage IV metastatic colorectal cancer;

Primary tumor location on the left side of the Colon (including left splenic flexure) or rectum; or preferably primary tumor location on the left side of the Colon (including left splenic flexure), but excluding rectum;

Demonstrated wild-type RAS mutation status in the tumor (primary tumor or metastasis) by local assessment; or preferably demonstrated wild-type KRAS mutation status in the tumor (primary tumor or metastasis) by local assessment;

Tumor tissue specimen shows high αvβ6 integrin expression, as determined by central laboratory assessment; or preferably tumor tissue specimen (formalin-fixed, paraffin-embedded block), preferably from primary resection and/or if available from a surgical sample from metastatic site;

In order to achieve the benefit of the treatments according to the invention and especially the preferred treatments according to the invention, the humans, human patients or patients shall preferably not have any RAS or BRAF mutation and especially any demonstrated RAS or BRAF mutation.

An especially preferred dose regimen according to the invention are described directly below and comprise or preferably consist of:

Treatment will be administered IV as 2-week cycles, each cycle (2 weeks) consisting of:

Cetuximab:
  400 mg/m² (preferably by IV infusion over 120 min), followed by 250 mg/m² weekly (preferably by IV infusion over 60 min)
  or
  500 mg/m² every two weeks, (preferably by IV infusion, initially over 120 min followed by 60 to 90 min)
    +(60 min [±5 min] after completion of the cetuximab infusion):

Abituzumab:
  1000 mg: every 2 weeks (preferably by IV infusion over 60 min)
    +(60 min [±5 min] after completion of the Abituzumab infusion)

FOLFIRI:
  every 2 weeks
  Irinotecan 180 mg/m² IV, 30-90 min day 1
  Folinic acid (preferably racemic) 400 mg/m² IV, 120 min day 1
  5-FU 400 mg/m² bolus day 1
  5-FU 2400 mg/m² IV, preferably over a period of 46 h day 1-2.

However, Cetuximab and FOLFIRI are preferred administered according to local standard and in line with recommendation of international guidelines (such as NCCN, ESMO). Dose adjustment for cetuximab and FOLFIRI is preferably at the investigators discretion according to the label or to the locally accepted practice.

Typically, the administration schedule will be cetuximab followed by Abituzumab (or other growth factor or growth factor receptor targeting monoclonal antibody) and FOLFIRI (or other chemotherapy, preferably FOLFOX), respectively.

Preferably, one hour should always be left between the end of cetuximab (or other growth factor or growth factor receptor targeting monoclonal antibody) infusion and the start of the Abituzumab infusion. Preferably, one hour should always be left between the end of the Abituzumab infusion and the start of FOLFIRI (or other chemotherapy, preferably FOLFOX) infusion in order to allow for the assessment of any medication related side effect, respectively.

The treatment regimens according to the invention should preferably applied for a minimum of 6 and more preferably minimum of 8 cycles and especially a minimum of 10 cycles. The treatment regimens according to the invention are preferably continued until disease regression or disease progression, unless unacceptable toxicities appear.

Abituzumab (EMD 525797) (mAb DI-17E6), is preferably currently available as a sterile solution for IV infusion. Abituzumab is preferably formulated as a 25 mg/mL solution in buffered saline containing a stabilizer and sodium chloride as an isotonicity agent.

Typically, Abituzumab 1000 mg is administered as a 1-hour (±5 minutes) IV infusion. A constant infusion rate can preferably be achieved by using a microprocessor-controlled infusion pump.

Typically, administration of Abituzumab will occur on Day 1 (preferably 60 minutes [±5 minutes] after completion of the cetuximab (or other growth factor or growth factor receptor targeting monoclonal antibody) infusion) and subsequently every 2 weeks, i.e. preferably on day 1 of each cycle of two weeks or about two weeks.

Confirmation of RAS WT mCRC by the local laboratory is preferably required prior to treatment and/or screening. Determination of a high $\alpha v\beta 6$ integrin expression by the central laboratory is preferably required before treatment and/or at screening phase.

Screening preferably comprises one or more of the following items:

TABLE 4

| Screening | |
|---|---|
| Primary tumor location and extent of disease TNM | Primary tumor staging and/or preferably staging |
| | Determination and documentation of tumor side (left) |
| Biomarker assessments | RAS or KRAS mutation analysis available from primary tumor locally (wild-type) |
| | FFPE tumor block for assessment of $\alpha v\beta 6$ integrin expression (high expression) |

Preferred objectives to be addressed by the method of treatment according to the invention preferably include Progression Free Survival (PFS), Overall Survival (OS), Objective response rate (ORR), Depth of response (DPR), Early tumor shrinkage (ETS) and/or Secondary resections rate with a potentially curative intent.

Depth of response (DPR) is preferably determined as the maximum percent tumor shrinkage during treatment.

Early tumor shrinkage (ETS) is preferably determined as the proportion of patients achieving a ≥20% decrease from baseline in the sum of longest tumor diameters.

Secondary resections rate with a potentially curative intent is preferably determined as follows Patients for whom the resectability of metastases becomes evident during the study therapy should undergo a surgical resection of the metastases.

Within the scope of this clinical study protocol, the conduct of secondary resection of metastases with a curative intent requires the prior demonstration of objective remission (CR or PR).

The known monoclonal anti-alpha v antibody with the registered and recommended International Non-proprietary Name (INN) "Abituzumab" is sometimes also referred to as DI-17E6, DI17E6, EMR62242 or EMD 525797.

Abituzumab or abituzumab, is an engineered specifically tailored IgG2 hybrid monoclonal antibody directed to alpha-v integrin (receptor). This antibody is described in detail in WO 2009/010290, the disclosure of which is incorporated herein by reference in its entirety.

Its hypervariable regions (CDRs) derive from murine mAb 17E6 (EMD 73034). This parent mouse IgG1 antibody is described, for example by Mitjans et al. (1995; J. Cell Sci. 108, 2825) and patents U.S. Pat. No. 5,985,278 and EP 719 859. Mouse mAb 17E6 is produced by hybridoma cell line 272-17E6 and deposited under accession number DSM ACC2160.

Its light chain domains derive from humanized monoclonal anti-EGFR antibody 425 (matuzumab). This antibody is described in detail for example in EP 0 531 472B1, and derives from its murine counterpart 425 (mouse MAb 425, ATCC HB9629), The antibody was raised against the human A431 carcinoma cell line and found to bind to a polypeptide epitope on the external domain of the human epidermal growth factor receptor (EGFR). Matuzumab has shown in clinical trials high efficacy.

Generally, the anti-αv integrin antibody Abituzumab/DI17E6 as used according to the invention comprises:

(i) a CDR light and a heavy chain region deriving from mouse monoclonal anti-αv integrin antibody 17E6

(ii) a light chain framework region which is taken from humanized monoclonal anti-EGFR antibody 425, (iii) a heavy chain framework region deriving from mouse monoclonal anti-αv integrin antibody 17E6, optionally comprising one or more mutations of amino acids at specific positions, and (iv) a heavy chain constant region deriving from human IgG2 and a human constant kappa light chain region, wherein in said IgG2 domain the IgG2 hinge region was replaced by the human IgG1 hinge domain, and; wherein optionally one or more mutations within the IgG2 has been carried out.

Specifically, Abituzumab/DI17E6 (also designated as "DI17E6γ2h(N297Q)" or "EMD 525797") as used for the treatment and in the clinical trials as described above and below, has the following amino acid sequence:

(i) variable and constant light chain sequences (SEQ ID No. 1):

DIQMTQSPSSLSASVGDRVTITCRASQDISNYLAWYQQKPGKAPKLLIYY

TSKIHS

GVPSRFSGSGSGTDYTFTISSLQPEDIATYYCQQGNTFPYTFGQGTKVEI

KRTVAA

PSVFIFPPSDEQLKSGTASVVCLLNNFYPREAKVQWKVDNALQSGNSQES

VTEQ

DSKDSTYSLSSTLTLSKADYEKHKVYACEVTHQGLSSPVTKSFNRGEC and (ii) variable and constant heavy chain sequences (SEQ ID No. 2):

QVQLQQSGGELAKPGASVKVSCKASGYTFSSFWMHWVRQAPGQGLEWI

GYINP

RSGYTEYNEIFRDKATMTTDTSTSTAYMELSSLRSEDTAVYYCASFLGRG

AMDY

WGQGTTVTVSSASTKGPSVFPLAPCSRSTSESTAALGCLVKDYFPEPVTV

SWNSG

ALTSGVHTFPAVLQSSGLYSLSSVVTVPSSNFGTQTYTCNVDHKPSNTKV

DKTV

EPKSSDKTHTCPPCPAPPVAGPSVFLFPPKPKDTLMISRTPEVTCVVVDV

SHEDPE

VQFNWYVDGVEVHNAKTKPREEQAQSTFRVVSVLTVVHQDWLNGKEYK

CKVS

NKGLPAPIEKTISKTKGQPREPQVYTLPPSREEMTKNQVSLTCLVKGFYP

SDIAVE

WESNGQPENNYKTTPPMLDSDGSFFLYSKLTVDKSRWQQGNVFSCSVM

HEALH

NHYTQKSLSLSPGK, wherein the underlined sequences represent the variable regions with the CDRs (in bold, identical with the parent mouse antibody). The modified IgG1 hinge region is represented by EPKSSDKTHTCPPCP (SEQ ID No. 3), and AQ is a substitution within the IgG2 domain.

However, as it was shown in WO 2009/010290, also variants of DI17E6 can be used according to the teaching of this invention. Thus, DI17E6 variants comprising one or more modifications within the heavy chain framework regions

|  |  | (SEQ ID No. 4) |
|---|---|---|
| FR1: | QVQLQQSGAELAEPGASVKMSCKASGYTFS | |
|  |  | (SEQ ID No. 5) |
| FR2: | WVKQRPGQGLEWIG | |
|  |  | (SEQ ID No. 6) |
| FR3: | KATMTADTSSSTAYMQLSGLTSEDSAVYYCAS | |
|  |  | (SEQ ID No. 7) |
| FR4: | WGQGTSVTVSS, | | wherein one or more of the bold and underlined positions are mutated, can be used in the treatment of prostate cancer patients as described. In more detail, the following position heavy chain framework region is mutated at one, more or all of the following positions can be mutated: A9, E13, M20, K38, R40, A72, S76, Q82, G85, T87, S91 and S113. These variants show the same or very similar biological activity and efficacy as compared to DI17E6 defined by its sequences above.

In general, the invention as described includes also modifications and variants of the DI17E6 antibody that are functionally and/or pharmaceutically identical or similar to unmodified DI17E6, and wherein the CDR regions and heavy and light chain variable regions are at least 90%, at least 95%, at least 98%, or at least 99% identical in their amino acid sequence compared to the respective variable regions of DI17E6. In addition, the invention preferably also includes modifications and variants of the DI17E6 antibody that are functionally and/or pharmaceutically identical or similar to unmodified DI17E6, and wherein the constant regions are at least 90%, at least 95%, at least 98%, or at least 99%, identical in their amino acid sequence compared to the respective constant regions of DI17E6. Changes in the constant regions of the IgG chains of the antibody may improve specific properties like immunogenicity, ADCC, and so on.

Preferably, the invention as described includes also modifications and variants of the DI17E6 antibody that are functionally and/or pharmaceutically identical or similar to (unmodified) DI17E6 or Abituzumab, and wherein the heavy and light chain variable regions are at least 95%, at least 98%, at least 99%, at least 99.5% or at least 99.9% identical in their amino acid sequence compared to the respective heavy and light chain variable regions of DI17E6. In addition, the invention also includes modifications and variants of the DI17E6 antibody that are functionally and/or pharmaceutically identical or similar to unmodified DI17E6, preferably as described above in this paragraph, wherein the constant regions are at least 90%, or at least 95%, or at least 99%, or at least 99.5%, or at least 99.9%, identical in their amino acid sequence compared to the respective constant regions of DI17E6. Changes in the constant regions of the IgG chains of the antibody may improve specific properties like immunogenicity, ADCC, and so on.

Even more preferably, the invention as described includes also modifications and variants of the DI17E6 antibody that are functionally and/or pharmaceutically identical or similar to (unmodified) DI17E6 or Abituzumab, and wherein the CDR regions on the variable heavy and/or light chain are at least 90%, at least 92%, at least 94%, at least 96%, at least 98% or at least 99% identical in their amino acid sequence compared to the respective CDR regions on the variable heavy and/or light chain regions of DI17E6. In addition, the invention also includes modifications and variants of the DI17E6 antibody that are functionally and/or pharmaceutically identical or similar to unmodified DI17E6, preferably as described above in this paragraph, wherein the constant regions are at least 90%, or at least 95%, or at least 99%, or at least 99.5%, or at least 99.9%, identical in their amino acid sequence compared to the respective constant regions of DI17E6.

Especially preferably, the invention as described includes also modifications and variants of the DI17E6 antibody that are functionally and/or pharmaceutically identical or similar to (unmodified) DI17E6 or Abituzumab, wherein the heavy and light chain CDR regions are 100% identical to (unmodified) DI17E6 or Abituzumab, but wherein the heavy and light chain variable regions other than said CDR regions are at least 95%, at least 98%, at least 99% or at least 99.5% identical in their amino acid sequence compared to the respective heavy and light chain variable regions of DI17E6. In addition, the invention preferably also includes modifications and variants of the DI17E6 antibody that are functionally and/or pharmaceutically identical or similar to unmodified DI17E6, preferably as described above in this paragraph, wherein the constant regions are at least 90%, or at least 95%, or at least 99%, or at least 99.5%, or at least 99.9%, identical in their amino acid sequence compared to the respective constant regions of DI17E6.

Especially preferably, the invention as described includes also modifications and variants of the DI17E6 antibody that are functionally and/or pharmaceutically identical or similar to (unmodified) DI17E6 or Abituzumab, wherein the CDR regions on the variable heavy and/or light chain are at least 90%, at least 92%, at least 94%, at least 96% or at least 98% identical in their amino acid sequence compared to the respective CDR regions on the variable heavy and/or light chain regions of DI17E6, and wherein the heavy and light chain variable regions other than said CDR regions are at least 95%, at least 98%, at least 99% or at least 99.5% identical in their amino acid sequence compared to the respective heavy and light chain variable regions of DI17E6. In addition, the invention preferably also includes modifications and variants of the DI17E6 antibody that are functionally and/or pharmaceutically identical or similar to unmodified DI17E6, preferably as described above in this paragraph, wherein the constant regions are at least 90%, or at least 95%, or at least 99%, or at least 99.5%, or at least 99.9%, identical in their amino acid sequence compared to the respective constant regions of DI17E6.

Further especially preferred for use as described herein is a modification or variant of the DI17E6 antibody that is preferably functionally and/or pharmaceutically identical or similar to (unmodified) DI17E6 or Abituzumab, comprising the sequence according to SEQ ID No. 1 and/or according to SEQ ID No. 2, wherein 1 to 10 amino acids, preferably 1 to 5 amino acids and especially 1 to 3 amino acids of the sequence of SEQ ID No. 1 and/or the sequence of SEQ ID No. 2 are substituted by different amino acids, preferably different naturally occurring amino acids. Thus, further especially preferred for use as described herein is a modification or variant of the DI17E6 antibody that is preferably functionally and/or pharmaceutically identical or similar to (unmodified) DI17E6 or Abituzumab, consisting of the sequence according to SEQ ID No. 1 and/or according to SEQ ID No. 2, wherein 1 to 10 amino acids, preferably 1 to 5 amino acids and especially 1 to 3 amino acids of the sequence of SEQ ID No. 1 and/or the sequence of SEQ ID No. 2 are substituted by different amino acids, preferably different naturally occurring amino acids. Thus, further especially preferred for use as described herein is a modification or variant of the DI17E6 antibody that is preferably functionally and/or pharmaceutically identical or similar to (unmodified) DI17E6 or Abituzumab, comprising a sequence that is at least 98%, preferably at least 99% and especially at least 99.9% identical to the sequence of SEQ ID No. 1 and/or SEQ ID No. 2. Thus, further especially preferred for use as described herein is a modification or variant of the DI17E6 antibody that is preferably functionally and/or pharmaceutically identical or similar to (unmodified) DI17E6 or Abituzumab, consisting of a sequence that is at least 98%, preferably at least 99% and especially at least 99.9% identical to the sequence of SEQ ID No. 1 and/or SEQ ID No. 2.

Especially preferably, the DI17E6 antibody or Abituzumab is a recombinant, de-immunized monoclonal antibody of the IgG2 subclass as described above and below which targets and inhibits ligand binding to human αv-integrins. Especially preferably, the carbohydrate structures normally present in the Fc region of said DI17E6 antibody or Abituzumab have been removed by genetically altering the amino acid residue that normally serves as the point of attachment rendering the molecule aglycosylated. The antibody is especially preferably composed of 4 polypeptide chains, 2 identical heavy chains consisting of 447 amino acids each and 2 identical light chains consisting of 214 amino acids each. Typically, the 4 chains are held together by a combination of covalent (disulfide) and non-covalent bonds. The approximate molecular weight of the molecule is 145 kDa.

However, most preferred for all methods, uses and treatments is the antibody with the registered International Non-proprietary Name (INN) Abituzumab.

PK assessment after single and multiple doses of Abituzumab preferably suggests that it behaves in accordance with a receptor-mediated clearance model as described for other antibodies targeting membrane-associated receptors. Consistent with the findings of an earlier study in healthy volunteers, PKs of Abituzumab in mCRPC patients are dose-dependent with clearance determined predominantly by the availability of unbound receptors. At the doses of Abituzumab preferably used, it can be assumed that at doses of 1000 mg or higher, preferably almost all receptors will be saturated and preferably do not contribute to drug clearance, or only to a minor extent.

The term "chemotherapy", as used herein, understood in the art. Preferably, it is understood as a type of cancer treatment that uses one or more anti-cancer drugs (chemotherapeutic agents) as part of a chemotherapy regimen.

The term "chemotherapeutic" or "chemotherapeutic agent" or "anti-neoplastic agent" is preferably regarded according to the understanding of this invention as a member of the class of "cytotoxic agents" and/or "cytostatic agents", and includes chemical agents that exert anti-neoplastic effects, i.e., prevent the development, maturation, or spread of neoplastic cells, directly on the tumor cell, and not indirectly through mechanisms such as biological response modification. Suitable chemotherapeutic agents according to the invention are preferably natural or synthetic chemical compounds, but biological molecules, other than proteins, polypeptides etc. are preferably not expressively excluded. Examples of chemotherapeutic or agents preferably include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; cytotoxic antibiotics and camptothecin derivatives. Preferred chemotherapeutic agents or chemotherapy include amifostine (ethyol), cabazitaxel, cisplatin, dacarbazine (DTIC), dactinomycin, docetaxel, mechlorethamine, streptozocin, cyclophosphamide, carmustine (BCNU), lomustine (CCNU), doxorubicin (adriamycin), doxorubicin lipo (doxil), gemcitabine (gemzar), daunorubicin, daunorubicin lipo (daunoxome), procarbazine, ketoconazole, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof. More preferred chemotherapeutic agents according to the invention in combination with Abituzumab are cabazitaxel, cisplatin, docetaxel, gemcitabine, doxorubicin, paclitaxel (taxol), irinotecan and bleomycin. Even more preferred chemotherapeutic agents according to invention for combination with Abituzumab are preferably selected from the group consisting of irinotecan, fluorouracil (5-FU), tegafur/uracil (UFT), folinic acid (leucovorin), Oxaliplatin (Eloxatin), aflibercept, regorafenib, capecitabine, and the prodrugs thereof, and the salts and solvates thereof. Most preferred chemotherapeutic agents according to invention for combination with Abituzumab are preferably either selected from the group consisting of irinotecan, fluorouracil (5-FU) and folinic acid (leucovorin), and the prodrugs thereof, or selected from the group consisting of Oxaliplatin, fluorouracil (5-FU) and folinic acid (leucovorin), and the prodrugs thereof, and the salts and solvates thereof.

Abituzumab is typically administered by intravenous injection, however other administration forms convenient in the art for antibody/protein drugs are applicable. All standard infusion solutions and formulation are applicable, such as described in WO 2005/077414 or WO 2003/053465, including liposomal formulations. It is, in addition, favorable to provide human serum albumin nanoparticles loaded with DI17E6 and optionally (to increase cytotoxicity) chemotherapeutic drugs (Biomaterials 2010, 8, 2388-98; Wagner et al.).

If not explicitly defined otherwise, the naming of an active ingredient, active principle (API), medicament or international nonproprietary name (INN) thereof preferably includes all prodrugs, salts and solvates thereof, especially those that are functionally equivalent and/or are deemed a suitable substitute from a clinical point of view.

If not explicitly defined otherwise, the terms humans, human beings, human patients or patients are preferably used herein as interchangeable or as synonyms.

If not explicitly defined otherwise, the terms human (being), human patient or (just) patient are preferably used herein as interchangeable or as synonyms.

If not explicitly defined otherwise, or detrimental to the context a certain term is used, usage of a term in singular is preferably meant to include that very term in plural, and the usage of a term in plural is preferably meant to include that very term in singular.

Especially preferred according to the invention are subjects as described herein, wherein the characteristics of two or more preferred, more preferred and/or especially preferred embodiments, aspects and/or subjects are combined into one embodiment, aspect and/or subject. Preferably, according to this invention, preferred subjects or embodiments can be combined with other preferred subjects or embodiments; more preferred subjects or embodiments can be combined with other less preferred or even more preferred subjects or embodiments; especially preferred subjects or embodiments can be combined with other just preferred or just even more preferred subjects or embodiments, and the like.

The term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of plus/minus 15% and especially of plus/minus 10%.

In any case, the term "about" as used herein with respect to numbers, figures, ranges and/or amounts is preferably meant to mean "circa" and/or "approximately". The meaning of those terms is well known in the art and preferably includes a variance, deviation and/or variability of the respective number, figure, range and/or amount of at least plus/minus 5%.

The terms "disorder(s)" and "disease(s)" as used herein are well-known and understood in the art. In the context of the present invention they are preferably used as synonyms and thus are preferably interchangeable, if the context they are used herein does not strongly implicate otherwise. Accordingly, the terms "fibrotic disorder(s)" and "fibrotic disease(s)" as used herein are also well-known and understood in the art. In the context of the present invention they are preferably used as synonyms and thus are preferably interchangeable, if the context they are used herein does not strongly implicate otherwise.

In the medical context, including, but not limited to treatment regimens, dosing schedules and clinical trial designs, for convenience and/or ease of use by patients, medical staff and/or physicians, as well as reliability and/or reproducibility of results etc., the terms "week"/"a week", "month"/"a month" and/or "year"/"a year" can used with slight deviations from the definitions of the Gregorian calendar. For example, in said medical context, a month is often referred to as 28 days, and a year is often referred to 48 weeks.

Thus, in the context of the instant invention, the term "week" or "a week" preferably refers to a period of time of about 5, about 6 or about 7 days, more preferably about 7 days.

In the medical context, the term "month" or "a month" preferably refers to a period of time of about 28, about 29, about 30 or about 31 days, more preferably about 28, about 30 or about 31 days.

In the medical context, the term "year" or "a year" preferably refers to a period of time of about 12 months or to a period of time of about 48, about 50, or about 52 weeks, more preferably 12 months, or about 48 or about 52 weeks.

The invention is explained in greater detail below by means of examples. The invention preferably can be carried out throughout the range claimed and is not restricted to the examples given here.

Moreover, the following examples are given in order to assist the skilled artisan to better understand the present invention by way of exemplification. The examples are not intended to limit the scope of protection conferred by the claims. The features, properties and advantages exemplified for the processes, compounds, compositions and/or uses defined in the examples may be assigned to other processes, compounds, compositions and/or uses not specifically described and/or defined in the examples, but falling under the scope of what is defined in the claims.

Thus, the following examples describe the invention in more detail but do not limit the invention and its scope as claimed The following examples describe the invention in more details but do not limit the invention and its scope as claimed.

EXAMPLES

Example 1

Abituzumab Combined with Cetuximab Plus Irinotecan Versus Cetuximab Plus Irinotecan Alone for Patients with KRAS Wild-Type Metastatic Colorectal Cancer: The Randomised Phase I/II POSEIDON Trial See also: Annals of Oncology 26: 132-140, 2015

Background: Integrins are involved in tumour progression and metastasis, and differentially expressed on colorectal cancer (CRC) cells. Abituzumab (EMD 525797), a humanised monoclonal antibody targeting integrin $\alpha v$ heterodimers, has demonstrated preclinical activity. This trial was designed to assess the tolerability of different doses of Abituzumab in combination with cetuximab and irinotecan (phase I) and explore the efficacy and tolerability of the combination versus that of cetuximab and irinotecan in patients with metastatic CRC (mCRC) (phase II part).

Methods: Eligible patients had KRAS (exon 2) wild-type mCRC and had received prior oxaliplatin-containing therapy. The trial comprised an initial safety run-in using Abituzumab doses up to 1000 mg combined with a standard of care (SoC: cetuximab plus irinotecan) and a phase II part in which patients were randomised 1:1:1 to receive Abituzumab 500 mg (arm A) or 1000 mg (arm B) every 2 weeks combined with SoC, or SoC alone (arm C). The primary end point was investigator-assessed progression-free survival (PFS). Secondary end points included overall survival (OS), response rate (RR) and tolerability. Associations between tumour integrin expression and outcomes were also assessed.

Results: Phase I showed that Abituzumab doses up to 1000 mg were well tolerated in combination with SoC. Seventythree (arm A), 71 (arm B) and 72 (arm C) patients were randomised to the phase II part. Baseline characteristics were balanced. PFS was similar in the three arms: arm A versus SoC, hazard ratio (HR) 1.13 [95% confidence interval (CI) 0.78-1.64]; arm B versus SoC, HR 1.11 (95% CI 0.77-1.61). RRs were also similar. A trend toward improved OS was observed: arm A versus SoC, HR 0.83 (95% CI 0.54-1.28); arm B versus SoC, HR 0.80 (95% CI 0.52-1.25). Grade ≥3 treatment-emergent adverse events were observed in 72%, 78% and 67% of patients. High tumour integrin $\alpha v \beta 6$ expression was associated with longer OS in arms A [HR 0.55 (0.30-1.00)] and B [HR 0.41 (0.21-0.81)] than in arm C.

Conclusion: The primary PFS end point was not met, although predefined exploratory biomarker analyses identified subgroups of patients in whom Abituzumab may have benefit. The tolerability of Abituzumab combined with cetuximab and irinotecan was acceptable. Further study is warranted.

ClinicalTrials.gov Identifier: NCT01008475

Key Words: Abituzumab, colorectal cancer, integrin, biomarker, monoclonal antibody, phase I/II

Introduction

Over the past 20 years, treatment options for metastatic colorectal cancer (mCRC) have expanded, particularly with the introduction of chemotherapies such as irinotecan and oxaliplatin and targeted agents such as cetuximab, panitumumab, aflibercept, regorafenib and bevacizumab [Van Cutsem E, Cervantes A, Nordlinger B et al. Metastatic colorectal cancer: ESMO Clinical Practice Guidelines for diagnosis, treatment and follow-up. Ann Oncol 2014; 25(suppl 3): iii1-iii9]. This has improved patient outcomes, but most patients die due to their disease. With increasing understanding of the molecular biology of CRC, novel therapies targeting factors essential to tumour growth and progression offer the best hope of improvement in patient outcomes [Ciombor K K, Berlin J. Targeting metastatic colorectal cancer-present and emerging treatment options. Pharmgenomics Pers Med 2014; 7: 137-144]. Integrins constitute a family of transmembrane, heterodimeric glycoproteins (comprising an a and a β subunit) that mediate a variety of cell-to-cell and cell-to-extracellular matrix (ECM) interactions in both normal and tumour cells [Goodman S L, Picard M. Integrins as therapeutic targets. Trends Pharmacol Sci 2012; 33: 405-412]. Integrins promote tumour cell survival, metastasis and angiogenesis [Nemeth J A, Nakada M T, Trikha M et al. Alpha-v integrins as therapeutic targets in oncology. Cancer Invest 2007; 25: 632-646]. Studies have shown that the integrins $\alpha v \beta 5$ and $\alpha v \beta 6$ are expressed on CRC cells, and integrins $\alpha v \beta 3$ and $\alpha v \beta 5$ are expressed on tumour-associated blood vessels [Goodman S L, Grote H J, Wilm C. Matched rabbit monoclonal antibodies against $\alpha v$-series integrins reveal a novel $\alpha v \beta 3$-LIBS epitope, and permit routine staining of archival paraffin samples of human tumors. Biol Open 2012; 1: 329-340; Agrez M V, Bates R C, Mitchell D et al. Multiplicity of fibronectin-binding alpha V integrin receptors in colorectal cancer. Br J Cancer 1996; 73: 887-892]. Overexpression of integrin $\alpha v \beta 6$ is associated with a significant reduction in median overall survival (OS) in patients with early stage mCRC [Bates R C, Bellovin D I, Brown C et al. Transcriptional activation of integrin β6 during the epithelial-mesenchymal transition defines a novel prognostic indicator of aggressive colon carcinoma. J Clin Invest 2005; 115: 339-347]. Therefore, $\alpha v$ integrins, and $\alpha v \beta 6$ in particular, represent a rational target for therapy in mCRC. The humanised monoclonal IgG2 antibody Abituzumab (EMD 525797) specifically binds to the αv integrin subunit, inhibiting the interaction with ligands in the ECM. This may prevent cell attachment and motility and induce apoptosis [Goodman S L, Picard M. Integrins as therapeutic targets. Trends Pharmacol Sci 2012; 33: 405-412; Mitjans F, Sander D, Adan J et al. An anti-alpha v-integrin antibody that blocks integrin function inhibits the development of a human melanoma in nude mice. J Cell Sci 1995; 108(Pt 8): 2825-2838]. In preclinical studies, anti-tumour activity has been observed with Abituzumab in human tumour xenograft models; greater activity than with either agent alone was observed when Abituzumab was combined with either cetuximab or irinotecan [Merck KGaA, data on file]. Furthermore, clinical studies of Abituzumab monotherapy have demonstrated its tolerability [Uhl W, Zuhlsdorf M, Koernicke T et al. Safety, tolerability, and pharmacokinetics of the novel alphav-integrin antibody EMD 525797 (DI17E6) in healthy subjects after ascending single intravenous doses. Invest New Drugs 2014; 32: 347-354; Wirth M, Heidenreich A, Gschwend J E et al. A multicenter phase 1 study of EMD 525797 (DI17E6), a novel humanized monoclonal antibody targeting alphav integrins, in progressive castration-resistant prostate cancer with bone metastases after chemotherapy. Eur Urol 2014; 65: 897-904]. We have conducted a phase I/II trial to characterise the tolerability of different doses of Abituzumab in combination with irinotecan and cetuximab, a standard of care (SoC) option for mCRC, in patients with KRAS exon 2 wild-type mCRC who had received prior therapy with an oxaliplatin-containing regimen. The phase II part of the trial compared the efficacy of Abituzumab in combination with irinotecan and cetuximab to that of irinotecan plus cetuximab in these patients.

Patients and Methods

Study Design and Treatment

Figure 4:
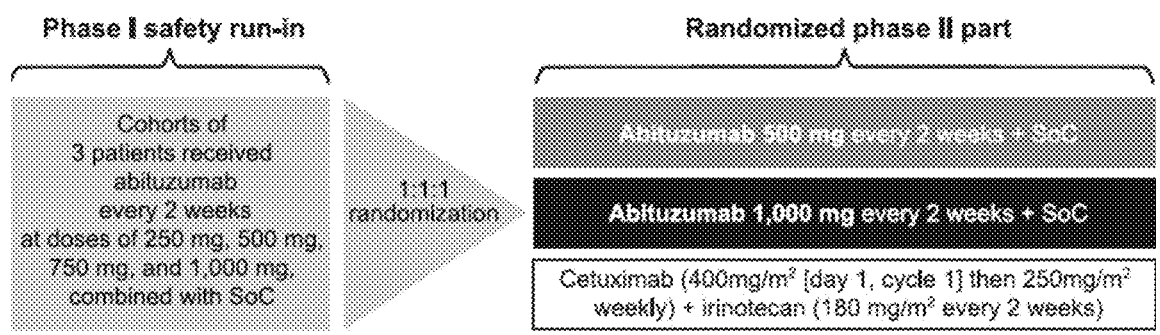
FIG. 4 shows a study design for Example 1.

This open-label, multicentre phase I/II study (ClinicalTrials.gov identifier: NCT01008475) was approved by the Institutional Review Board at each institution. All patients gave informed consent before enrolment. The study was conducted according to the principles of the Declaration of Helsinki. In the phase I dose-escalation part, a classical '3+3' design was used in which eligible patients received Abituzumab 250, 500, 750 or 1000 mg i.v. every 2 weeks in combination with SoC. Abituzumab doses were selected based on pharmacokinetic (PK) modelling of the potentially active dose range with reference to the degree of target saturation. Patients received cetuximab 400 mg/m2 on day 1 of cycle 1 and 250 mg/m2 weekly thereafter. Abituzumab was administered ≥60 min after the completion of cetuximab infusion, and irinotecan 180 mg/m2 (maximum body surface area of 2.0 m2) was administered 60 min after the completion of Abituzumab infusion to allow assessment of infusion-related side-effects. Treatment was continued until disease progression or unacceptable toxicity. Dose-limiting toxicities (DLTs) were defined as: treatment-related death within the first 2 weeks of treatment; or any grade ¾ non-haematologic toxicity or grade 4 haematologic toxicity related to study treatment. Toxicities expected with cetuximab and irinotecan, such as grade 4 neutropenia or leukopenia without fever and lasting ≤5 days and grade ¾ diarrhoea without adequate supportive care, were not included as DLTs [Elez E, Kocákova I, Höhler T et al. Phase I study of EMD 525797 (DI17E6), an antibody targeting αvβ integrins, in combination with cetuximab and irinotecan, as a second-line treatment for patients with k-ras wild-type metastatic colorectal cancer. J Clin Oncol 2012; 30(suppl): abstract 3539]. In the randomised phase II part of the trial, patients were centrally randomised 1:1:1 to treatment with either Abituzumab 500 mg or Abituzumab 1000 mg every 2 weeks combined with SoC, or SoC (cetuximab weekly and irinotecan every 2 weeks) (FIG. 4). The selection of two Abituzumab doses for the phase II part was due to the availability of insufficient data from the phase I part to allow selection of one dose and mainly PK-guided to achieve different levels of target saturation: Abituzumab 500 mg every 2 weeks is likely to provide serum concentrations at which preclinical activity has been observed; Abituzumab 1000 mg every 2 weeks was selected to provide steady-state serum trough concentrations constantly above the IC99 of the nonlinear clearance pathway between doses. Patients were stratified based on whether or not anti-vascular endothelial growth factor (VEGF) therapy had been administered previously. Treatment continued until radiographically documented disease progression as assessed by the investigator, unacceptable toxicity, eligibility for curative resection (investigator's assessment) or withdrawal of consent.

Patients

Adults aged 8 years with histologically confirmed KRAS exon 2 wild-type mCRC, documented distant metastases and at least one radiographically documented measurable lesion in a previously non-irradiated area were eligible. All patients must have failed a prior oxaliplatin/fluoropyrimidine-containing regimen, defined as disease progression within 6 months of the last dose or intolerance. Patients had an Eastern Cooperative Oncology Group (ECOG) performance status of 0 or 1 or Karnofsky performance status ≥80%, and acceptable laboratory parameters (including absolute neutrophil count ≥1.5×109/l, platelets ≥100×109/l, haemoglobin ≥9 g/dl and bilirubin≥1.5×upper limit of normal). Key exclusion criteria included prior treatment with any epidermal growth factor receptor inhibitor, known brain metastases, clinically relevant coronary artery disease, uncontrolled hypertension and history of myocardial infarction in the past 12 months.

Assessments

All patients were required to provide tumour blocks for KRAS mutation analysis and assessment of integrin expression during screening. Integrin αvβ3, αvβ5, αvβ6, αvβ8 and pan-αv expression was assessed using immunohistochemistry on formalin-fixed, paraffin-embedded tumour tissue as previously described [Goodman S L, Grote H J, Wilm C. Matched rabbit monoclonal antibodies against αv-series integrins reveal a novel αvβ3-LIBS epitope, and permit routine staining of archival paraffin samples of human tumors. Biol Open 2012; 1: 329-340]. Data on intensity and frequency of staining were used to calculate histoscores on a continuous scale of 0-300, as previously described [Pirker R, Pereira J R, von Pawel J et al. EGFR expression as a predictor of survival for first-line chemotherapy plus cetuximab in patients with advanced non-small cell lung cancer: analysis of data from the phase 3 FLEX study. Lancet Oncol 2012; 13: 33-42]. Patients were monitored for treatment-emergent adverse events (TEAEs) from the time of study entry until 31 days after the final dose of study drug. The causal relationship between the study drug and a TEAE was assessed by the investigator. Tumours were assessed by imaging using computed tomography (CT) or magnetic resonance imaging (MRI) scans at baseline and every 6 weeks from the date of randomisation until disease progression or death. RECIST was used to objectively assess response [Therasse P, Arbuck S G, Eisenhauer E A et al. New guidelines to evaluate the response to treatment in solid tumors. European Organization for Research and Treatment of Cancer, National Cancer Institute of the United States, National Cancer Institute of Canada. J Natl Cancer Inst 2000; 92: 205-216]. Complete and partial responses (CR or PR) had to be confirmed by a scan weeks after the initial scan. During the randomised phase II part of the trial, all scans were reviewed by an Independent Review Committee. All patients withdrawing from the trial for any reason other than death without a tumour assessment after initial screening underwent a final treatment assessment including CT or MRI scan. statistical considerations Descriptive statistics were used to summarise the phase I primary end point of protocol-defined DLT and other data for each dose level. The primary end point of the randomised phase II part of the trial was progression-free survival (PFS), defined as the time from randomisation to disease progression or death from any cause within 12 weeks after last tumour assessment. A sample size of 213 patients (71 per arm) was planned to observe the 173 PFS events needed to reject the null hypothesis of no drug activity with a power of 85% assuming a hazard ratio (HR) of 0.67 versus SoC, an increase in median PFS from 4.0 months with SoC to 6.0 months with Abituzumab-based therapy and significance level (a) of 25% (two-sided). Secondary end points for the phase II part included OS, time to progression, time to treatment failure, response and disease control rates and safety. Predefined exploratory end points included the association of tumour integrin expression with efficacy. The primary analysis of efficacy used the intent-to-treat (ITT) population comprising all patients randomised. The safety analysis population included all patients who received at least one dose of any study drug. Data were summarised using descriptive statistics. Log-rank tests stratified by previous anti-cancer treatment (anti-VEGF yes/no) were used to analyse time-to-event end points. The Cox proportional hazards model with treatment and previous anti-cancer treatment (anti-VEGF yes/no) as covariates was used to estimate HRs. Statistical analyses were carried out using the SAS® System (version 8.2 or later). For the assessment of the exploratory end point of association of tumour integrin expression with patient outcomes, the median histoscore was initially used as a cut-off between high and low expression. The cut-off was then varied around the median to assess whether the median was acceptable for the patient population in the trial.

Results

Phase I Dose-Escalation Study

Sixteen patients were enrolled into the phase I dose-escalation study between October 2009 and October 2010. No DLTs were observed at any dose level (Table 5). However, an additional three patients were enrolled at the 750 mg dose because one of the first three patients died due to causes unrelated to Abituzumab after the DLT observation period. A fourth additional patient was enrolled because one patient received Abituzumab 250 mg rather than the planned 750 mg dose. Abituzumab-related TEAEs were uncommon and included grade 3 hypokalaemia (one patient at 250 mg) and grade 3 tachyarrhythmia (one patient at 1000 mg) (Table 5). No grade 4 neutropenia, grade 3/4 thrombocytopenia or grade 3/4 decrease in haemoglobin was observed; the study regimen did not worsen renal, liver or pulmonary function nor cardiac output. Abituzumab dose duration generally increased with increasing dose; median relative dose intensity was >96% at all dose levels. The relative dose intensity of cetuximab and irinotecan was maintained. Evidence of anti-tumour activity was observed at all dose levels, with one CR and four PRs, as well as seven patients with stable disease (Table 5). Together, these data justified further evaluation of Abituzumab combined with cetuximab and irinotecan.

TABLE 5

Characteristics, safety and efficacy for patients enrolled into the phase I dose-escalation study

| | Abituzumab dose (mg) | | | |
|---|---|---|---|---|
| | 250 (n = 3) | 500 (n = 3) | 750 (n = 7) | 1,000 (n = 3) |
| Characteristic | | | | |
| Median age, years (range) | 61 (51-74) | 62 (45-66) | 60 (53-66) | 65 (55-69) |
| Male:female, n (%) | 1 (33)/2 (67) | 2 (67)/1 (33) | 3 (43)/4 (57) | 1 (33)/2 (67) |
| Caucasian, n (%) | 3 (100) | 3 (100) | 7 (100) | 3 (100) |
| ECOG performance status, n (%) | | | | |
| 0 | 3 (100) | 2 (67) | 4 (57) | 1 (33) |
| 1 | 0 | 1 (33) | 2 (29) | 2 (67) |
| 2 | 0 | 0 | 1 (14) | 0 |
| Stage IV, n (%) | 3 (100) | 3 (100) | 7 (100) | 3 (100) |
| Prior chemotherapy, n (%)* | 3 (100) | 3 (100) | 7 (100) | 3 (100) |
| Prior radiotherapy, n (%) | 0 | 0 | 4 (57) | 1 (33) |
| Safety | | | | |
| DLT, n (%) | 0 | 0 | 0 | 0 |
| Grade 3/4 TEAE, n (%) | 3 (100) | 1 (33) | 5 (71) | 3 (100) |
| Abituzumab-related grade 3/4 TEAE, n (%) | 1 (33) | 0 | 0 | 1 (33) |
| Abituzumab-related serious TEAE, n (%) | 1 (33) | 0 | 0 | 1 (33) |

TABLE 5-continued

Characteristics, safety and efficacy for patients enrolled into the phase I dose-escalation study

| | Abituzumab dose (mg) | | | |
|---|---|---|---|---|
| | 250 (n = 3) | 500 (n = 3) | 750 (n = 7) | 1,000 (n = 3) |
| Abituzumab-related TEAE leading to study discontinuation, n (%) | 1 (33) | 0 | 0 | 0 |
| Fatal TEAE, n (%) | 0 | 0 | 2 (29) | 0 |
| Treatment-related fatal TEAE, n (%) | 0 | 0 | 0 | 0 |
| Efficacy | | | | |
| CR/PR/SD, n (%) | 0 (0)/1 (33)/2 (67) | 0 (0)/0 (0)/1 (33) | 1 (14)/1 (14)/3 (43)[554] | 0 (0)/2 (67)/1 (33) |
| Disease control, n (%)‡ | 2 (67) | 0 | 4 (57) | 3 (100) |

Figure 5:
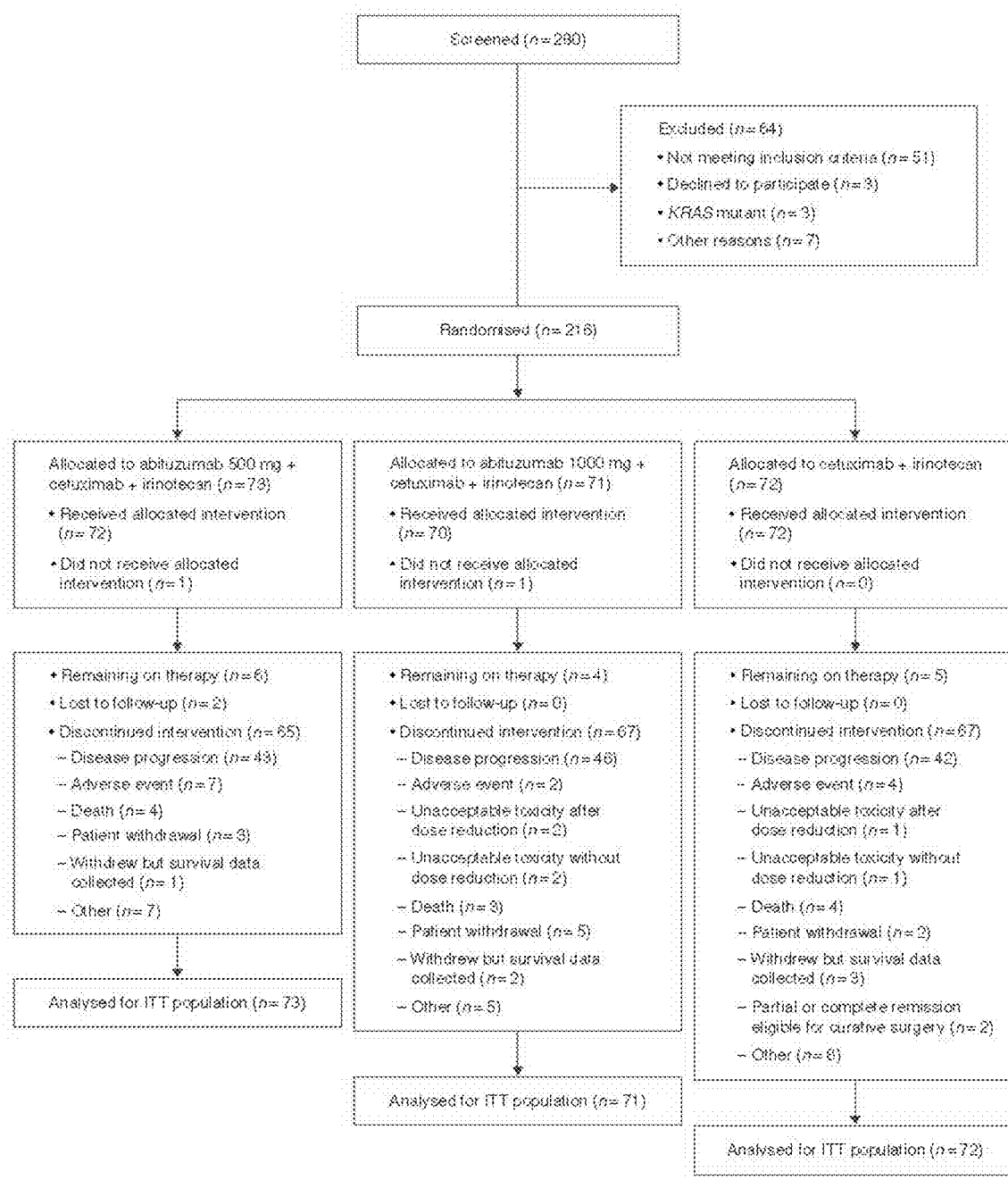
FIG. 5 shows a CONSORT diagram for the phase II part of the trial.

*All patients had received first-line oxaliplatin/fluoropyrimidine-containing therapy for mCRC.
†Two patients were not evaluable.
‡Defined as CR, PR or SD for 42 days.
CR, complete response
ECOG, Eastern Cooperative Oncology Group;
PR, partial response;
SD, stable disease
TEAE, treatment-emergent adverse events Randomised Phase II Study
Patients A total of 216 patients were enrolled and randomised between April 2011 and October 2013. A CONSORT diagram is shown in FIG. 5.

Figure 6A:
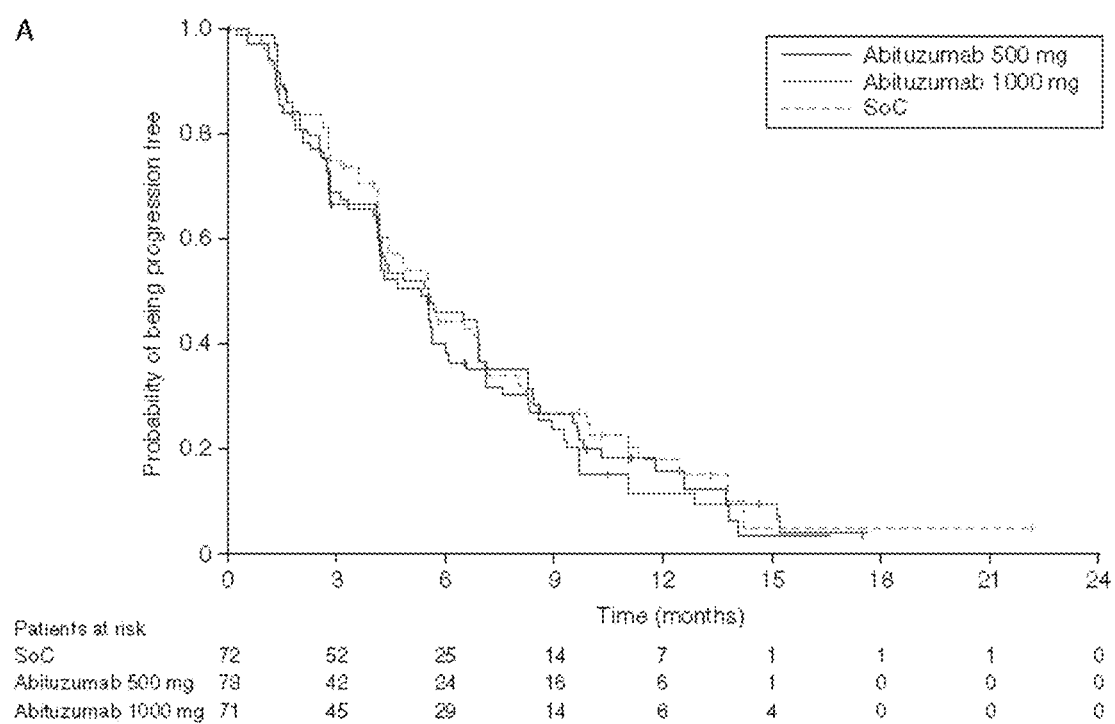
FIG. 6A shows the Kaplan-Meier curve for PFS in the ITT population, where SoC, Abituzumab 500 mg, and Abituzumab 1000 mg are all curves which are identical at 16 months.
Figure 6B:
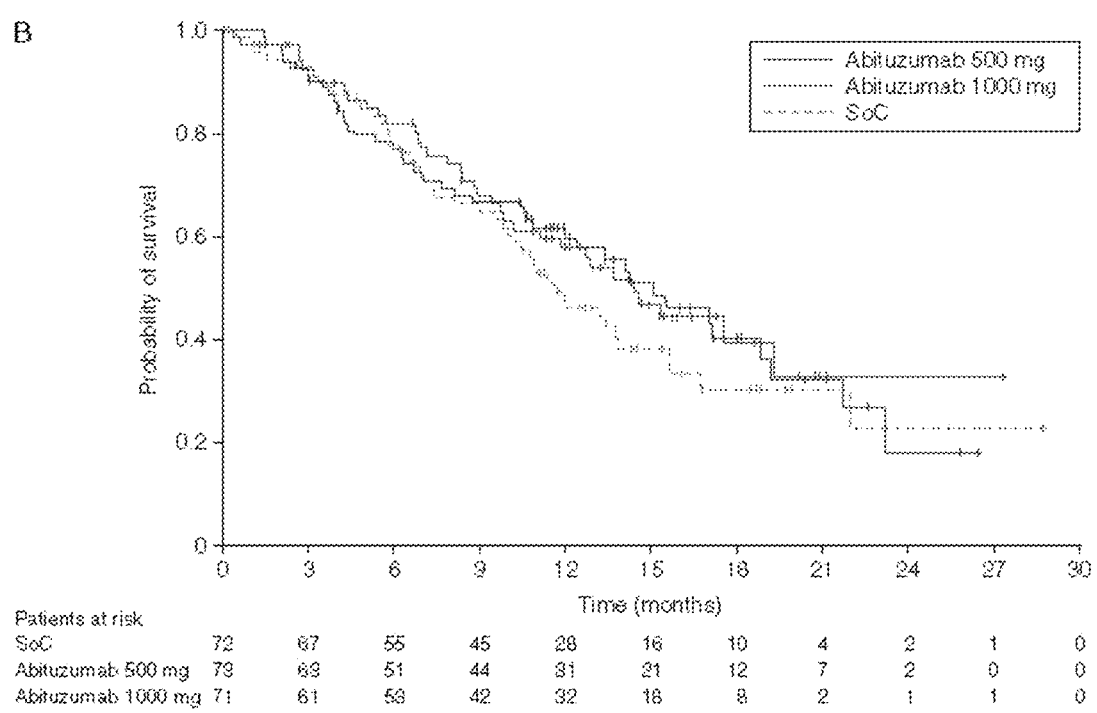
FIG. 6B shows the Kaplan-Meier curve for OS in the ITT population, where SoC is the median curve at 24 months; Abituzumab 500 mg is the lowest curve at 24 months; and Abituzumab 1000 mg is the highest curve at 24 months.

Median (range) time on trial (informed consent to death, discontinuation or last assessment on trial) was 13.6 (0.1-26.2), 12.3 (0.5-27.3+) and 11.6 (0.6-28.8+) months in the Abituzumab 500 mg, Abituzumab 1000 mg and SoC arms, respectively. The median duration of Abituzumab treatment overall was 4.1 months at a median relative dose intensity of 98%. Baseline characteristics of patients in the three treatment arms were generally well balanced (Table 6). safety. All patients in the Abituzumab arms and all except one (99%) in the SoC arm experienced a TEAE (Table 2); TEAEs of grade ≥3 were observed in 72%, 78% and 67% of patients in the Abituzumab 500 mg, Abituzumab 1000 mg and SoC arms, respectively. These data indicate that Abituzumab has an acceptable safety profile in combination with cetuximab and irinotecan. However, ~50% of TEAEs in the Abituzumab arms, including grade ≥3 TEAEs in 17% and 29% of patients in the Abituzumab 500 and 1000 mg arms, were suspected to be related to Abituzumab based on investigator assessment; serious Abituzumab related TEAEs included febrile neutropenia, colitis, rectal abscess, peripheral neuropathy and acute renal failure, each occurring in one patient treated with Abituzumab 500 mg; and neutropenia, gastrointestinal infection and deep vein thrombosis, each occurring in one patient treated with Abituzumab 1000 mg. At the time of data cut-off, 39 (54%), 35 (51%) and 45 (62%) patients had died in the Abituzumab 500 mg, Abituzumab 1000 mg and SoC arms, respectively. Two deaths, one in the Abituzumab 1000 mg arm and one in the SoC arm, both due to sepsis, were considered to be related to irinotecan; 32/39, 30/35 and 38/45 deaths were due to disease progression. efficacy. Efficacy data for the ITT population are shown in Table 7 and FIG. 6A-B. These show that neither PFS nor response rate (RR) differed between the treatment arms. Median OS was 15.0 [95% confidence interval (CI) 10.9-19.2] months with Abituzumab 500 mg [HR 0.83 (95% CI 0.54-1.28) versus SoC], 14.4 (95% CI 9.8-19.3) months with Abituzumab 1000 mg [HR 0.80 (95% CI 0.52-1.25) versus SoC] and 11.6 (95% CI 9.8-15.7) months with SoC (FIG. 6B).

TABLE 6

Baseline demographics (ITT population)

| Characteristic | Abitazumab 500 mg + cetuximab + irinotecan (N = 73) | Abitimurnab 1000 mg + cetuximab + irinotecan (N = 71)[a] | Cetuximab + irinotecan (N = 72) |
|---|---|---|---|
| Median age, years (range) | 60 (27-83) | 61 (25-83) | 58 (26-76) |
| Median time since CRC diagnosis, months (range) | 13 (3-108) | 14 (2-118) | 13 (3-95) |
| Male/female, n (%) | 37 (51)/36 (49) | 48 (68)/23 (32) | 45 (63)/27 (37) |
| ECOG performance status, n (%) | | | |
| 0 | 35 (48) | 30 (42) | 30 (42) |
| 1 | 37 (51) | 40 (56) | 42 (58) |
| Missing | 1 (1) | 1 (1) | 0 |
| Confirmed stage IV disease, n (%) | 72 (95) | 71 (100) | 72 (100) |
| Prior surgery, n (%) | 68 (93) | 53 (75) | 62 (86) |
| Prior radiotherapy, n (%) | 10 (14) | 10 (14) | 11 (15) |
| Prior anti-cancer drug therapy, n (%) | 73 (100) | 71 (100) | 72 (100) |
| Prior anti-VEGF therapy, n (%) | 32 (44) | 30 (42) | 32 (44) |

[a]One patient did not receive abituzumab, but did receive a single cetuximab infusion and is considered in the SoC arm for the purposes of safety analyses.

TABLE 7

Efficacy data for the ITT population and by integrin αvβ6 expression level

| | ITT population | | | High integrin αvβ6 expression | | | Low integrin αvβ6 expression | | |
|---|---|---|---|---|---|---|---|---|---|
| Outcome | Abituzumab 500 mg + cetuximab + irinotecan (N - 73) | Abituzumab 1000 mg + cetuximab + irinotecan (N - 73) | Cetuximab + irinotecan (N - 72) | Abituzumab 500 mg + cetuximab + irinotecan (N - 36) | Abituzumab 1000 mg + cetuximab + irinotecan (N - 31) | Cetuximab + irinotecan (N - 31) | Abituzumab 500 mg + cetuximab + irinotecan (N - 30) | Abituzumab 1000 mg + cetuximab + irinotecan (N - 35) | Cetuximab + irinotecan (N - 34) |
| Median PFS (months) | 5.4 | 5.6 | 5.6 | 5.6 | 6.9 | 4.2 | 4.2 | 4.9 | 5.8 |
| 95% CI | 4.1  6.0 | 4.1  6.9 | 4.2  6.9 | 2.8  8.3 | 2.7  9.7 | 2.6  6.9 | 2.8  6.0 | 2.8  6.9 | 4.2  9.9 |
| HR | 1.13 | 1.11 | | 0.84 | 0.71 | | 1.50 | 1.74 | |
| 95% CI | 0.78  1.64 | 0.77  1.61 | | 0.49  1.45 | 0.40  1.26 | | 0.84  2.65 | 1.02  3.00 | |
| P value | | | | 0.535 | 0.245 | | 0.168 | 0.044 | |
| Median OS (months) | 15.0 | 14.4 | 11.6 | 15.0 | NR | 10.2 | 13.4 | 12.8 | 13.8 |
| 95% CI | 10.9  19.2 | 9.8  19.3 | 9.8  15.7 | 10.5  23.2 | 9.7  NR | 5.8  13.1 | 6.2  21.7 | 7.9  17.5 | 10.0  NR |
| HR | 0.83 | 0.80 | | 0.55 | 0.41 | | 1.48 | 1.58 | |
| 95% CI | 0.54  1.28 | 0.52  1.25 | | 0.30  1.00 | 0.21  0.81 | | 0.74  2.97 | 0.82  3.06 | |
| P value | | | | 0.048 | 0.010 | | 0.271 | 0.172 | |
| Response rate (%) | 27 | 25 | 26 | 30.6 | 32.3 | 16.1 | 27 | 23 | 32 |
| 95% CI | 18  39 | 16  37 | 17  38 | 16.3  48.1 | 16.7  51.4 | 5.5  33.7 | 12  46 | 10  40 | 17  51 |
| OR | 1.05 | 0.95 | | 2.29 | 2.48 | | 0.76 | 0.62 | |
| 95% CI | 0.51  2.19 | 0.45  2.00 | | 0.70  7.53 | 0.73  8.37 | | 0.26  2.24 | 0.21  1.80 | |

NR, not reached; OR, odds ratio.

Biomarker Analysis

Figure 7:
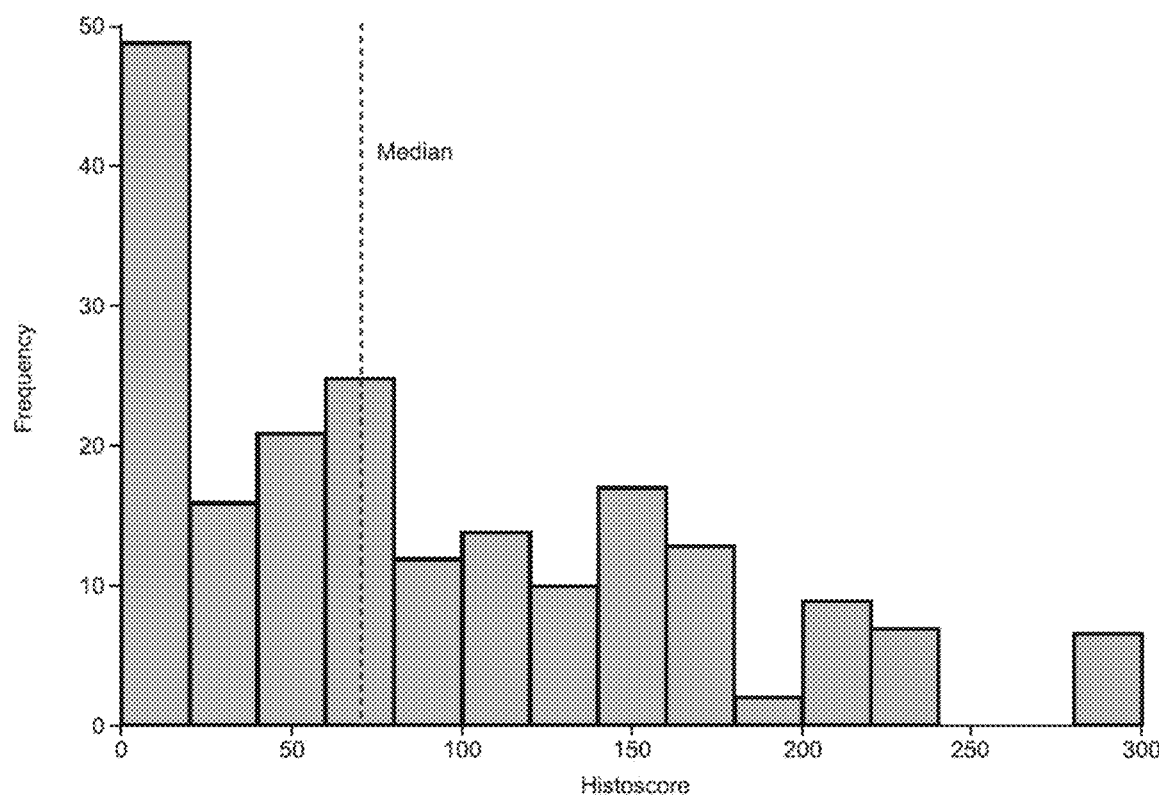
FIG. 7 shows histogram showing αvβ6 histoscores for all patients with tumor blocks available (n=197) and the median histoscore (70) for this population. Histoscores were generated for each patient by integrating data relating to the intensity and frequency of αvβ6 staining, using the formula: 1×(percentage of cells staining weakly [1+])+2×(percentage of cells staining moderately [2+])+3×(percentage of cells staining strongly [3+]) [12].

A pre-planned exploratory biomarker analysis carried out to better understand the relationship between αv integrin expression and outcomes suggested that high integrin αvβ6 expression [above the median of the population studied (n=197); median histoscore=70] (FIG. 7) may be negatively prognostic for OS in the SoC arm and predictive for prolonged OS with Abituzumab treatment (FIG. 6 and Table 7). The analysis also suggested that RR may be improved in patients with tumours with high integrin αvβ6 expression. In contrast, patients with tumours with low integrin αvβ6 expression (below the median) did not appear to benefit from Abituzumab therapy (Table 7). Too few patients with a tumour integrin αvβ6 histoscore of 0 (n=24) were included to allow analysis of this population. The predictive and prognostic value of pan-αv integrin levels (median histoscore=230) appeared similar to those of integrin αvβ6, whereas levels of integrin αvβ5 did not appear to be predictive or prognostic and integrins αvβ3 and αvβ8 were not expressed (data not shown).

DISCUSSION

This is the first reported clinical trial of an integrin inhibitor in patients with CRC. The addition of Abituzumab to cetuximab plus irinotecan had limited activity in an unselected mCRC population who have received prior oxaliplatin therapy; however, a pre-specified exploratory biomarker analysis suggested that Abituzumab may produce an OS benefit in patients with tumours showing high integrin αvβ6 expression. OS represents the gold standard end point for clinical trials in cancer [European Medicines Agency. Guideline on the evaluation of anticancer medicinal products in man. In Committee for Medicinal Products for Human Use (ed), London, UK: European Medicines Agency 2013; Food and Drug Administration. Guidance for industry: clinical trial endpoints for the approval of cancer drugs and biologics. In Services USDoHaH (ed), Rockville, MD, USA: Food and Drug Administration 2007], and while OS was a secondary end point in this trial, the exploratory biomarker data suggest that further studies in a patient population with high tumour αvβ6 expression with a primary OS end point are warranted. The development of a companion diagnostic test to select the appropriate patient population will be crucial for further trials. The pre-planned exploratory analysis suggested that integrin αvβ6 expression may be a negative prognostic factor, with patients with high levels having median OS ~4 months shorter than patients with low levels [HR 1.95 (95% CI 1.04-3.67)], in agreement with a previous study showing significantly inferior OS in patients with early-stage mCRC with high tumour integrin αvβ6 expression [Bates R C, Bellovin D I, Brown C et al. Transcriptional activation of integrin β6 during the epithelial-mesenchymal transition defines a novel prognostic indicator of aggressive colon carcinoma. J Clin Invest 2005; 115: 339-347]. However, with Abituzumab treatment, the analysis suggested that the risk of death for patients with high tumour integrin αvβ6 expression may be reduced by up to 59% compared with the control arm. PFS and RR also appeared to be increased with Abituzumab therapy in this biomarker-selected population with poor prognosis. In contrast, we did not demonstrate any association between integrin αvβ5 levels and clinical outcomes; no previous studies have reported a prognostic or predictive role for integrin αvβ5 in CRC. Studies in early-stage cancer suggest that integrin αvβ6 is involved in the epithelial-mesenchymal transition (EMT), which enhances the invasive behaviour of epithelial tumours such as CRC [Bates R C. Colorectal cancer progression: integrin alphavbeta6 and the epithelial mesenchymal transition (EMT). Cell Cycle 2005; 4: 1350-1352]. The EMT process may also contribute to metastatic disease, and the high levels of integrin αvβ6 seen in hepatic and lymphatic metastases suggest a role for integrin αvβ6 in the aggressiveness of mCRC [Bates R C, Bellovin D I, Brown C et al. Transcriptional activation of integrin β6 during the epithelial-mesenchymal transition defines a novel prognostic indicator of aggressive colon carcinoma. J Clin Invest 2005; 115: 339-347; Bates R C. Colorectal cancer progression: integrin alphavbeta6 and the epithelial mesenchymal transition (EMT). Cell Cycle 2005; 4: 1350-1352]. Furthermore, integrin αvβ6 is a known activator of latent transforming growth factor-β (TGF-β), which stimulates tumour growth and invasion during colon cancer progression [Bates R C. Colorectal cancer progression: integrin alphavbeta6 and the epithelial mesenchymal transition (EMT). Cell Cycle 2005; 4: 1350-1352]. Therefore, therapies inhibiting integrin αvβ6 would have the potential to target invading and metastasising tumour cells, possibly explaining the improvements in OS and PFS observed with Abituzumab in patients with tumours with high αvβ6 expression in this trial. TGF-β also has a key role in regulating immune function and integrins are critical to this process [Travis M A, Sheppard D. TGF-beta activation and function in immunity. Annu Rev Immunol 2014; 32: 51-82]. The potential of tumour integrin αvβ6 inhibition by Abituzumab to decrease the inhibitory activity of TGF-6 on anti-tumour immune responses might explain the apparently more pronounced effect of Abituzumab on OS than PFS and RR. This study has several limitations that need to be considered when interpreting the data. The keys ones are that the trial was a phase II trial and that the biomarker data, while hypothesis-generating, are based on a pre-planned exploratory analysis. Further trials will need to be conducted to confirm the prognostic and predictive value of αv integrins in patients with mCRC treated with Abituzumab. In conclusion, our data indicate that integrin-targeted therapy may have a role in the treatment of selected patients with mCRC. Exploratory analyses indicated that Abituzumab based therapy may be effective in patients with tumours with high integrin αvβ6 expression, who have otherwise poor prognosis. Further trials in this population and potentially development of a companion diagnostic test are warranted to further assess the activity of Abituzumab in mCRC.

REFERENCES

1. Van Cutsem E, Cervantes A, Nordlinger B et al. Metastatic colorectal cancer: ESMO Clinical Practice Guidelines for diagnosis, treatment and follow-up. Ann Oncol 2014; 25(suppl 3): iii1-iii9.
2. Ciombor K K, Berlin J. Targeting metastatic colorectal cancer—present and emerging treatment options. Pharmgenomics Pers Med 2014; 7: 137-144.
3. Goodman S L, Picard M. Integrins as therapeutic targets. Trends Pharmacol Sci 2012; 33: 405-412.
4. Nemeth J A, Nakada M T, Trikha M et al. Alpha-v integrins as therapeutic targets in oncology. Cancer Invest 2007; 25: 632-646.
5. Goodman S L, Grote H J, Wilm C. Matched rabbit monoclonal antibodies against αv-series integrins reveal a novel αvβ3-LIBS epitope, and permit routine staining of archival paraffin samples of human tumors. Biol Open 2012; 1: 329-340.
6. Agrez M V, Bates R C, Mitchell D et al. Multiplicity of fibronectin-binding alpha V integrin receptors in colorectal cancer. Br J Cancer 1996; 73: 887-892.
7. Bates R C, Bellovin D I, Brown C et al. Transcriptional activation of integrin β6 during the epithelial-mesenchymal transition defines a novel prognostic indicator of aggressive colon carcinoma. J Clin Invest 2005; 115: 339-347.
8. Mitjans F, Sander D, Adan J et al. An anti-alpha v-integrin antibody that blocks integrin function inhibits the development of a human melanoma in nude mice. J Cell Sci 1995; 108(Pt 8): 2825-2838.
9. Uhl W, Zuhlsdorf M, Koernicke T et al. Safety, tolerability, and pharmacokinetics of the novel alphav-integrin antibody EMD 525797 (DI17E6) in healthy subjects after ascending single intravenous doses. Invest New Drugs 2014; 32: 347-354.
10. Wirth M, Heidenreich A, Gschwend J E et al. A multicenter phase 1 study of EMD 525797 (DI17E6), a novel humanized monoclonal antibody targeting alphav integrins, in progressive castration-resistant prostate cancer with bone metastases after chemotherapy. Eur Urol 2014; 65: 897-904.
11. Elez E, Kocáková I, Höhler T et al. Phase I study of EMD 525797 (DI17E6), an antibody targeting αvβ integrins, in combination with cetuximab and irinotecan, as a second-line treatment for patients with k-ras wild-type metastatic colorectal cancer. J Clin Oncol 2012; 30(suppl): abstract 3539.
12. Pirker R, Pereira J R, von Pawel J et al. EGFR expression as a predictor of survival for first-line chemotherapy plus cetuximab in patients with advanced non-small cell lung cancer: analysis of data from the phase 3 FLEX study. Lancet Oncol 2012; 13: 33-42.
13. Therasse P, Arbuck S G, Eisenhauer E A et al. New guidelines to evaluate the response to treatment in solid tumors. European Organization for Research and Treatment of Cancer, National Cancer Institute of the United States, National Cancer Institute of Canada. J Natl Cancer Inst 2000; 92: 205-216.
14. European Medicines Agency. Guideline on the evaluation of anticancer medicinal products in man. In Committee for Medicinal Products for Human Use (ed), London, UK: European Medicines Agency 2013.
15. Food and Drug Administration. Guidance for industry: clinical trial endpoints for the approval of cancer drugs and biologics. In Services USDoHaH (ed), Rockville, MD, USA: Food and Drug Administration 2007.
16. Bates R C. Colorectal cancer progression: integrin alphavbeta6 and the epithelial mesenchymal transition (EMT). Cell Cycle 2005; 4: 1350-1352.
17. Travis M A, Sheppard D. TGF-beta activation and function in immunity. Annu Rev Immunol 2014; 32: 51-82.

Example 2

Patient Selection for Targeting Integrin with Abituzumab in Patients with Metastatic Colorectal Cancer (mCRC). A Retrospective Analysis of the Randomized Phase I/II Poseidon Study.

Introduction

Targeting integrins, specifically αvβ6, is a novel approach to the treatment of mCRC. Histochemical data have shown that the targets of Abituzumab (αv integrins) are expressed on the tumor vasculature and tumor cells of CRC.

In particular, αvβ6 integrin expression has also been proposed as a prognostic factor in CRC as it was analyzed in more than 700 mCRC patients. (Bates R C, et al. J Clin Invest. 2005; 115(2):339-347; Niu Z, et al. Cell Biosci; 2014; 4:23; Yang G Y, et al. World J Gastroenterol. 2015; 21(24):7457-7467; Elez E, et al. Ann Oncol. 2015; 26:132-140). High αvβ6 expression in colon cancer tumors were indicators of tumor's progression and poor survival of these patients.

There is increasing evidence that mCRC is a genetically heterogeneous disease and that tumors arising from different sides of the colon (left versus right) have different clinical outcomes. (Arnold D, et al. Ann Oncol. 2017; 28:1713-1729). Previous analyses comparing the activity of different classes of targeted agents in patients with k-RAS wild-type (WT) or RAS WT mCRC suggest that primary tumor location (side), might be both prognostic and predictive for clinical outcome.

This retrospective data analysis of αvβ6 investigates the difference between right- and left-sided k-RAS WT CRC based on exploratory data from the Poseidon study and whether there is a difference in patients with right- versus left-sided mCRC and their outcome when treated with Abituzumab.

Background

Figure 8:
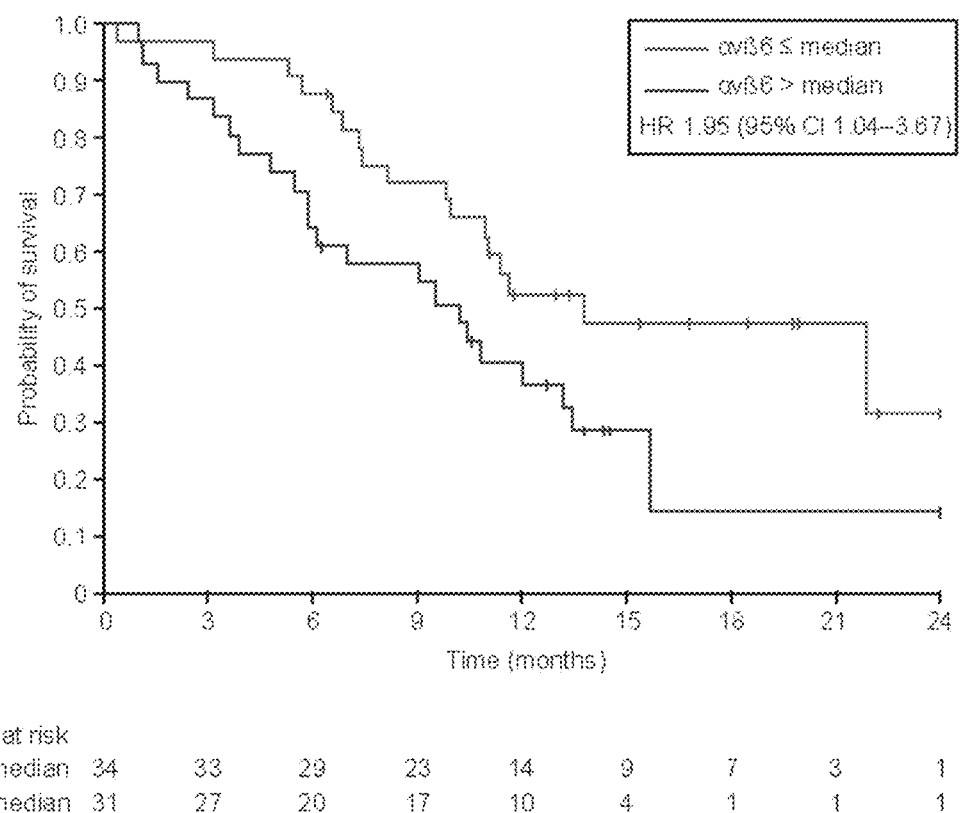
FIG. 8 shows an OS curve in Patients with High and Low αvβ6 Expression who Received Cetuximab+Irinotecan Alone (Poseidon Study), where αvβ6>median is the lower curve at 24 months; αvβ6<median is the higher curve at 24 months; CI is confidence interval; and HR is hazard ratio.

In the Poseidon study (NCT01008475)(Elez E, et al. Ann Oncol. 2015; 26:132-140) exploring the activity of Abituzumab in combination with cetuximab and irinotecan in 2nd-line k-RAS WT mCRC, the analysis of the cetuximab+irinotecan alone group also demonstrated that high αvβ6 expression is associated with a poorer outcome, suggesting that a high αvβ6 expression is a negative prognostic factor (FIG. 8).

The primary endpoint, progression free survival (PFS), in the intention-to-treat population, failed to demonstrate a statistically significant benefit in a phase I/II in 2nd-line k-RAS WT (k-RAS WT exon-2) mCRC in the previous Poseidon study. (Elez E, et al. Ann Oncol. 2015; 26:132-140). A pre-planned exploratory biomarker analysis suggested that high integrin αvβ6 expression may be negatively prognostic for overall survival (OS) in the control arm and predictive for prolonged OS under Abituzumab treatment. (Elez E, et al. Ann Oncol. 2015; 26:132-140)

Figure 9:
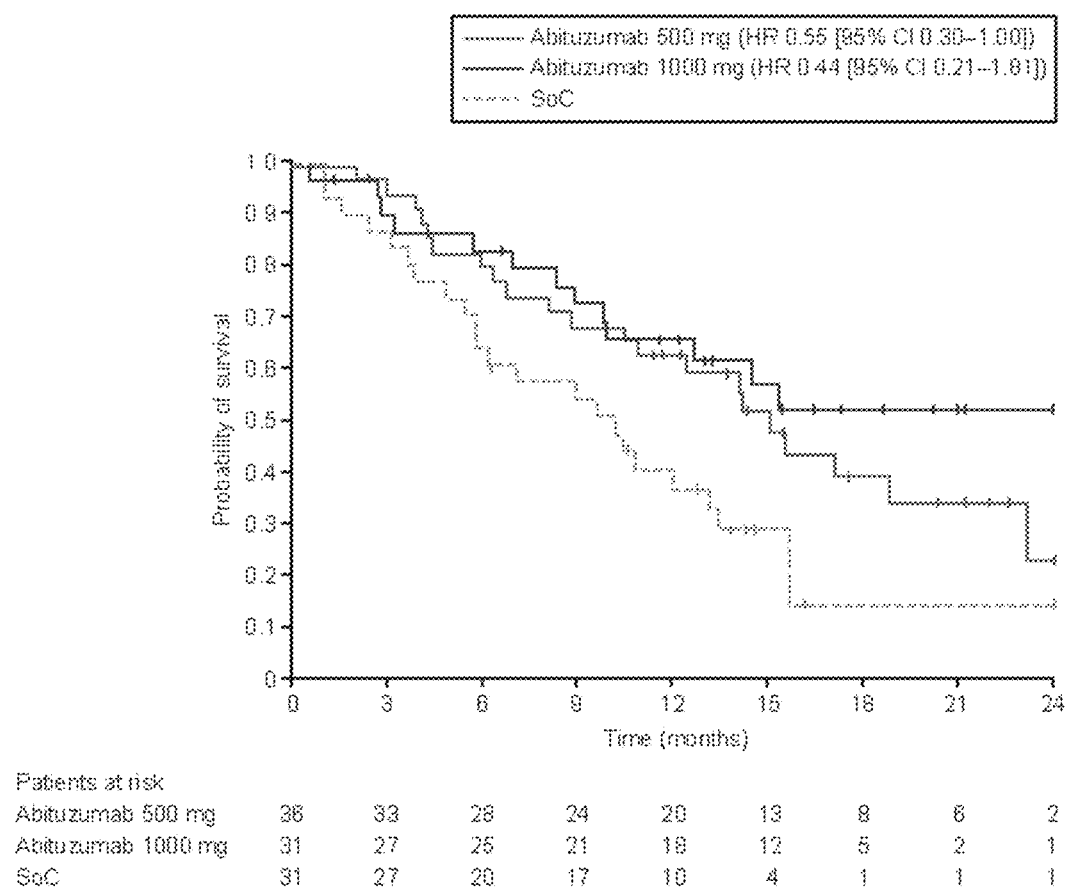
FIG. 9 shows an OS Curve in Patients with High αvβ6 expression Treated with Abituzumab+Cetuximab+Irinotecan versus Cetuximab+Irinotecan Alone (SOC) in Patients with Both Right and Left-sided Tumors (Poseidon Study), where SoC is the lowest curve at 24 months; Abituzumab 500 mg is the median curve at 24 months; Abituzumab 1000 mg is the highest curve at 24 months; CI is confidence interval; HR is hazard ratio; and SoC is standard of care.

The previous exploratory data analysis of the Poseidon study showed that patients with high αvβ6 expression (histoscore >70) treated with Abituzumab achieved a higher PFS, OS and objective response rate (ORR), suggesting that high αvβ6 expression (histoscore >70) is predictive for response to Abituzumab (FIG. 9).

Methods

Retrospective Analysis Poseidon Study

Analysis of integrin αvβ6 expression in formalin-fixed paraffin-embedded tumor tissue was part of the Poseidon study; a pre-planned retrospective analysis of the patient material was conducted (n=98 patients with high and n=99 low αvβ6 expression).

Figure 10A:
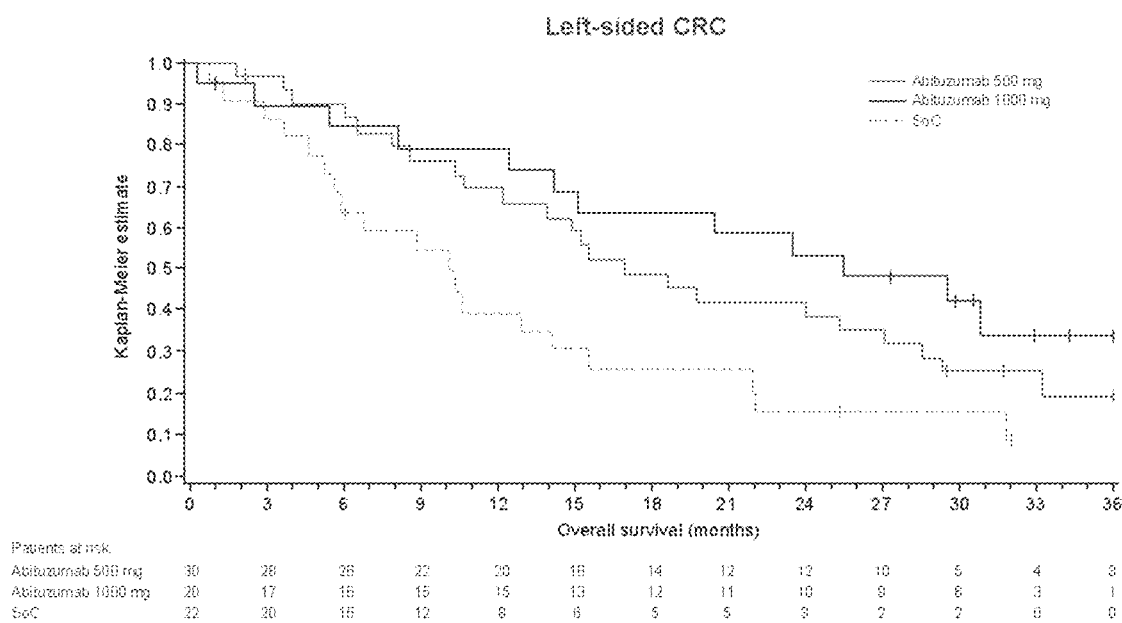
FIG. 10A shows a retrospective analysis of OS in Patients with High αvβ6 Expression, Left-sided (Poseidon Study), where SoC is the lowest curve at 24 months; Abituzumab 500 mg is the median curve at 24 months; Abituzumab 1000 mg is the highest curve at 24 months.
Figure 10B:
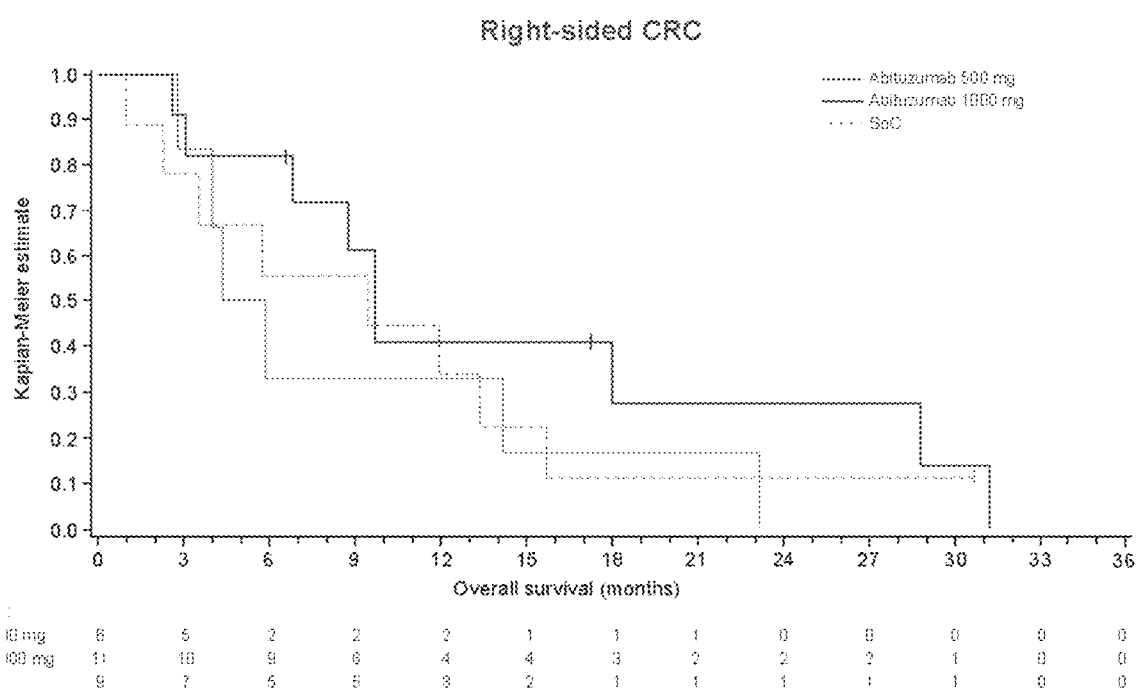
FIG. 10B shows a retrospective analysis of OS in Patients with High αvβ6 Expression, Right-sided (Poseidon Study), where SoC is the lowest curve at 18 months; Abituzumab 500 mg is the median curve at 18 months; and Abituzumab 1000 mg is the highest curve at 18 months.

Retrospective analyses of Poseidon study data were performed to correlate the impact of tumor location (left n=152 versus right n=44, one patient had both right and left colorectal cancer) and integrin αvβ6 expression (low versus high); OS, PFS and ORR for Abituzumab added to irinotecan+cetuximab were analyzed (Table 8, FIGS. 10A, 10B).

TABLE 8

Retrospective Analysis Poseidon Study: PFS, ORR and OS

| | High Histoscore | | | Low Histoscore | |
|---|---|---|---|---|---|
| | Abituzumab 1000 mg + cetuximab + irinotecan | Abituzumab 500 mg + cetuximab + irinotecan | cetuximab + irinotecan | Abituzumab 1000 mg + cetuximab + irinotecan | cetuximab + irinotecan |
| PFS, months (n) | | | | | |
| All Patients | 6.9 (31) | 5.6 (36) | 4.2 (26) | 4.9 (35) | 5.8 (34) |
| Right CRC | 2.6 (11) | 2.8 (6) | 4.2 (9) | 3.5 (8) | 4.2 (5) |
| Left CRC | 8.6 (20) | 5.6 (30) | 4.2 (22) | 5.4 (27) | 6.5 (29) |
| ORR, % (n) | | | | | |
| All Patients | 35.5 (31) | 30.6 (36) | 16.1 (26) | 20.0 (35) | 32.4 (34) |
| Right CRC | 18.2 (11) | 0 (6) | 0 (9) | 12.5 (8) | 20.0 (5) |
| Left CRC | 45.0 (20) | 36.7 (30) | 22.7 (22) | 22.2 (27) | 34.5 (29) |
| OS (n) | | | | | |
| All Patients | 20.6 (31) | 15.5 (36) | 10.2 (31) | 12.8 (35) | 15.9 (34) |
| Right CRC | 9.8 (11) | 5.1 (6) | 9.5 (9) | 8.6 (8) | 10.0 (5) |
| Left CRC | 25.6 (20) | 17.1 (30) | 10.2 (22) | 13.6 (27) | 15.9 (29) |

CRC, colorectal cancer;
ORR, objective response rate;
OS, overall survival;
PFS, progression free survival

TABLE 9

Retrospective Analysis Poseidon Study: HR for OS

| Abituzumab | Population | HR | HR 95% confidence survival | P-value |
|---|---|---|---|---|
| 500/1000 mg | Left/αvβ6- above | 0.454 | 0.257-0.805 | 0.0068 |
| 500 mg | Left/αvβ6- above | 0.527 | 0.284-0.976 | 0.0416 |
| 1000 mg | Left/αvβ6- above | 0.357 | 0.171-0.746 | 0.0061 |

HR, hazard ratio;
OS, overall survival

CONCLUSIONS

Although the sample size is small, patients with left sided k-RAS WT mCRC and high expression of αvβ6 integrin in their tumor seem to benefit most from the addition of Abituzumab to irinotecan+cetuximab compared with irinotecan+cetuximab alone.

No benefit was seen in patients with a low histoscore.

Abituzumab doses up to 1000 mg were well tolerated in combination with irinotecan+cetuximab in the Poseidon study. (Arnold D, et al. Ann Oncol. 2017; 28:1713-1729).

This retrospective data analysis of the 2nd-line Poseidon study confirms the observation of a treatment effect difference for left-sided versus right-sided in k-RAS WT mCRC in patients who received an EGFR-inhibitor such as cetuximab or panitumumab for their 1st-line metastatic disease. (Arnold D, et al. Ann Oncol. 2017; 28:1713-1729).

Independently, αvβ6 integrin expression may serve as a new biomarker in mCRC.

REFERENCES

1. Bates R C, et al. J Clin Invest. 2005; 115(2):339-347.
2. Niu Z, et al. Cell Biosci; 2014; 4:23.
3. Yang G Y, et al. World J Gastroenterol. 2015; 21(24): 7457-7467
4. Elez E, et al. Ann Oncol. 2015; 26:132-140.
5. Arnold D, et al. Ann Oncol. 2017; 28:1713-1729.

Example 3

RAS Wild-Type, KRAS Wild-Type and/or NRAS Wild-Type Testing Procedures Therascreen® KRAS RGQ PCR Kit & Method I. General Information Device Generic Name: Real-time PCR test
Device Trade Name: Therascreen® KRAS RGQ PCR Kit
Device Procode: OWD
Applicant's Name and Address: QIAGEN Manchester Ltd. Skelton House, Lloyd Street North Manchester, UK M15 6SH
Date(s) of Panel Recommendation: None
Premarket Approval Application (PMA) Number: P110027
Date of FDA Notice of Approval: May 23, 2014
Expedited: Not applicable The original PMA (P110030) for the Therascreen® KRAS RGQ PCR Kit was approved on Jul. 6, 2012 and is indicated to aid in the identification of CRC patients for treatment with Erbitux® (cetuximab) based on a KRAS no mutation detected test result. The SSED to support the indication is available on the CDRH website and is incorporated by reference here. The current PMA (P110027) was submitted to expand the indication for the Therascreen® KRAS RGQ PCR Kit.

II. Indications for Use

The Therascreen® KRAS RGQ PCR Kit is a real-time qualitative PCR assay used on the Rotor-Gene Q MDx instrument for the detection of seven somatic mutations in the human KRAS oncogene, using DNA extracted from formalin-fixed paraffin-embedded (FFPE), colorectal cancer (CRC) tissue. The Therascreen® KRAS RGQ PCR Kit is intended to aid in the identification of CRC patients for treatment with Erbitux® (cetuximab) and Vectibix® (panitumumab) based on a KRAS no mutation detected test result.

III. Contraindications

None.

IV. Warnings and Precautions

The warnings and precautions can be found in the Therascreen® KRAS RGQ PCR Kit labeling.

V. Device Description

The following components comprise the overall device:
QIAGEN QIAamp® DSP DNA FFPE Tissue Kit
QIAGEN Therascreen® KRAS RGQ PCR Kit
QIAGEN Rotor-Gene Q MDx. Software version 2.1.0, and KRAS Assay Package
Specimen Preparation Formalin-fixed, paraffin-embedded (FFPE) blocks are sectioned onto glass slides. A stained slide is used to confirm that the tumor content exceeds 20% of the tissue and that a minimum tumor area of 4 mm$^2$ is available. A single non-stained tissue section is scraped from the slide for DNA extraction. If sections have a tumor content of less than 20%, the section should be macrodissected. DNA is manually extracted and purified from 5 μm glass-mounted sections of FFPE tissue taken from colorectal cancer patients using the QIAGEN QIAamp® DSP DNA FFPE Tissue Kit and a modified protocol. The tumor tissue is deparaffinized with xylene and the xylene is extracted with ethanol. The sample is lysed under denaturing conditions with proteinase K for one hour. The sample is heated at 90° C. to reverse formalin cross-linking of genomic DNA. The sample is passed through a silica-based membrane so that genomic DNA binds to the membrane and contaminants are removed. Purified genomic DNA is eluted from the membrane into 200 μL of elution buffer. Extracted DNA is stored at −20° C.
PCR Amplification and Detection The QIAGEN Therascreen® KRAS RGQ PCR Kit contains reagents for eight separate reactions; seven mutation specific reactions to amplify and detect mutations in codons 12 and 13 in exon 2 of the KRAS oncogene, and one Control Reaction that amplifies and detects a region of exon 4 in the KRAS oncogene. Each reaction in the KRAS RGQ Kit makes use of an amplification refractory mutation system (ARMS®) allele specific polymerase chain reactions (PCR) to selectively amplify mutated genomic DNA templates (mutation-positive) in a background of non-mutated genomic DNA (mutation-negative; wild-type) combined with a fluorophore-labeled Scorpion® primer to detect any resultant amplification product. ARMS technology exploits the ability of Taq polymerase to distinguish between a match and a mismatch at the 3' end of a PCR primer. Scorpions are bifunctional molecules containing a PCR primer covalently linked to a probe. The probes incorporate both a fluorophore, [carboxyfluorescein (FAM™)] and a quencher which quenches the fluorescence of the fluorophore. During PCR, when the probe binds to the ARMS amplicon, the fluorophore and quencher become separated leading to a detectable increase in fluorescence.

Before testing with the mutation-specific test reactions, each DNA sample must be tested with the Control Reaction to determine whether the quality and quantity of DNA is sufficient and appropriate for the working range of the assay. The Control Reaction Ct value is used to assess the total amplifiable DNA in a sample and must fall within prespecified ranges for each sample.

The interpretation of the results obtained from the Control reaction is as follows:

TABLE 10

Interpretation of the results obtained from the Control reaction

| Control Ct value | Interprotation | Action |
| --- | --- | --- |
| >32.00 | Quantity of amplifiable DNA is not sufficientfor mutation analysis. | Additional samples should be extracted and tested |
| <21.92 | Quantity of amplifiable DNA is too high for mutation analysis. | Dilute with the sample diluent water supplied in the kit |
| 21.92 ≤ Control Ct ≥ 32.00 | Quantity of amplifiable DNA is suitable for mutation analysis | — |

The run parameters used for assessing the DNA sample with the Control Reaction mix are the same run parameters for mutation analysis using the Mutation Reaction mixes. The run parameters are: (1) Hold at 95° C. for 15 minutes to activate the Taq polymerase; (2) PCR for 40 cycles of 95° C. for 30 seconds, to denature, and 60° C. for 1 minute, to anneal/extend. The PCR cycle at which the fluorescence from a particular reaction crosses the pre-defined threshold value is defined as the Ct value. The seven mutations in codons 12 and 13 of the KRAS oncogene detected by the Therascreen® KRAS RGQ Kit are listed below:

TABLE 11

Seven mutations in codons 12 and 13 of the KRAS oncogene detected by the therascreen ® KRAS RGQ Kit

| Mutation | Base Change |
| --- | --- |
| GLY12ALA (G12A) | GGT > GCT |
| GLY12ASP (G12D) | GGT > GAT |
| GLY12ARG (G12R) | GGT > CGT |
| GLY12CYS (G12C) | GGT > TGT |
| GLY12SER (G12S) | GGT > AGT |
| GLY12VAL (G12V) | GGT > GTT |
| GLY12ASP (G12D) | GGT > GAC |

Test Controls

Each test run must contain an Internal Control, the Positive Control, and the Negative Control. A test run is considered invalid if the Negative Control indicates that the test run has been contaminated (Ct value above a set value for the FAM channel) or if the Positive Control Ct value lies outside a set range (both FAM and HEX channels).

TABLE 12

Run Validity Criteria

| Reaction | Sample | RGQ Channel | Valid Ct Range |
| --- | --- | --- | --- |
| Control | Positive Control | FAM | 23.50 to 29.50 |
| Control | No Template Control | FAM | No amplification |
| Control | No Template Control | HEX | 31.90 to 35.16 |
| Mutation | Positive Control | FAM | 23.50 to 29.50 |
| Mutation | No Template Control | FAM | No amplification |
| Mutation | No Template Control | HEX | 31.91 to 35.16 |

*Ranges are inclusive

Internal Control:

All eight reactions contain an additional ARMS primer and a HEX-labeled Scorpion primer for the amplification and detection of a synthetic non KRAS related oligonucleotide template that is used as an Internal Control. The Scorpion primer is labeled with HEX to distinguish from the FAM-labeled Scorpions in the control and mutation reactions. In each reaction, the Internal Control reaction is designed to be the weaker of the two reactions. This is achieved through the use of a very low concentration of Internal Control template. The Internal Control reaction is designed to work independently of mutation-specific amplification, but can fail in the presence of strong amplification if it is "out-competed" by the FAM reaction. A mutation negative result with a failed Internal Control reaction in any one of the seven mutation reactions will be reported as an invalid result. The Internal Control is used to detect inhibitors or gross reaction failures.

Positive Control:

The positive control is comprised of a mixture of synthetic oligonucleotides representing each of the mutations detected by the Therascreen® KRAS RGQ Kit. Detection of the positive control confirms the proper functioning of each of the reaction mixes in the Kit.

Negative Control:

The Therascreen® KRAS RGQ Kit contains nuclease-free water to be used as a no template control (NTC) reaction. The NTC serves as a negative control and assesses potential contamination during assay set up.

Instrument and Software

The Rotor-Gene Q (RGQ) MDx Instrument is a real-time PCR analyzer designed for thermocycling and real-time detection of amplified DNA. The RGQ MDx Instrument controls and monitors PCR reactions and includes the software that determines mutation status based upon PCR results. It incorporates a centrifugal rotor design for thermal cycling during PCR reactions where each tube spins in a chamber of moving air. Samples are heated and cooled in a low-mass-air oven according to a software determined cycle that initiates the different phases of the PCR cycle for a total of 40 cycles for each PCR run. In the RGQ MDx Instrument, samples are excited from the bottom of the chamber by a light emitting diode. Energy is transmitted through the thin walls at the base of the tube. Emitted fluorescence passes through the emission filters on the side of the chamber and is detected by a photomultiplier tube. Detection is performed as each tube aligns with the detection optics; tubes spin past the excitation/detection optics every 150 milliseconds. The fluorescence signals monitor the progress of the PCR reactions. The instrument is capable of supporting up to six optical channels (six excitation sources and six detection filters), however only two of these channels (the FAM and HEX channels) are used with the Therascreen® KRAS RGQ Kit.

The Therascreen® KRAS Assay Package consists of two templates: the "Therascreen® KRAS QC Locked Template" (for DNA sample assessment) and the "Therascreen® KRAS Locked Template" (for detection of KRAS mutations). These templates contain the PCR run parameters and calculate the results. The same run parameters are used for both the DNA sample assessment with the Control Reaction Mix and for detection of KRAS mutations using the mutation reaction mixes.

The RGQ MDx Instrument software supports real-time analysis procedures. The software determines Ct values, calculates ΔCt values, and compares these to the mutation-specific cut-off values incorporated into the software as described above. A system of Flags/Warnings is embedded within the software in order to inform the user of potential problems with the assay and to indicate non-valid test runs or non-valid samples within a valid test run (inappropriate level of DNA or Internal Control failure). No results are reported for invalid runs or for non-valid samples. Users of the KRAS RGQ Kit cannot make subjective determinations of mutation status as they do not have access to the Ct or ΔCt values and only see the mutation status calls reported by the software.

Interpretation of Results

The Ct for the control reaction reflects the total amount of amplifiable KRAS template in the sample, while the Ct for the allele specific reactions reflect the amount of KRAS mutation within the sample. The difference in Ct values (ΔCt) between the control reaction and the allele-specific reaction indicates the proportion of mutation within the sample. The ΔCt value approaches 0 as the proportion of mutant DNA in the samples increases. The ΔCt value increases (approaches the threshold for positive vs. negative call) as the proportion of mutant DNA in the sample decreases. When the ΔCt measure exceeds ΔCt cut-off values for the mutant reactions, the assay reports no mutation detected (e.g., negative for the 7 mutations).

For each sample, a calculation is performed by the RGQ MDx Instrument software to determine the ΔCt value (FAM channel) for each of the 7 mutation-specific reactions:

[Mutation reaction $Ct$ value]−[Control Reaction $Ct$ value]=Δ$Ct$

Based on pre-determined analytical Ct and ΔCt values, the Rotor-Gene Q software qualitatively determines the mutation status of the DNA samples and reports which samples contain which mutation. Each sample will have seven possible ΔCt values (one per mutation). These values are compared to pre-established specifications (cut-off values) incorporated into the RGQ MDx Instrument software to determine whether a sample is mutation positive or negative and which mutation, if any, is present. When the mutation reaction ΔCt value is less than or equal to the cut-off value for that reaction, the sample is KRAS mutation-positive. The assay results will be displayed as "Mutation Positive," "No Mutation Detected," "Invalid" or, if a run control fails, "Run Control Failed." For the mutation-positive samples, specific mutations are reported.

Cobas® KRAS Mutation Test

I. General Information

Device Generic Name: Real-time PCR test
Device Trade Name: Cobas® KRAS Mutation Test
Device Procode: OWD
Applicant's Name and Address: Roche Molecular Systems, Inc. (RMS) 4300 Hacienda Drive Pleasanton, CA 94588-2722
Date of Panel Recommendation: None
Premarket Approval Application (PMA) Number: P140023
Date of Notice of Approval: May 7, 2015
Expedited: Not Applicable II. Indications for Use The Cobas® KRAS Mutation Test, for use with the Cobas® 4800 System, is a real-time PCR test for the detection of seven somatic mutations in codons 12 and 13 of the KRAS gene in DNA derived from formalin-fixed paraffin-embedded human colorectal cancer (CRC) tumor tissue. The test is intended to be used as an aid in the identification of CRC patients for whom treatment with Erbitux® (cetuximab) or with Vectibix® (panitumumab) may be indicated based on a no mutation detected result. Specimens are processed using the Cobas® DNA Sample Preparation Kit for manual sample preparation and the cobas z 480 analyzer for automated amplification and detection.

III. Contraindications

There are no known contraindications for use for this test.

IV. Warnings and Precautions

Warnings and precautions can be found in the Cobas® KRAS Mutation Test product labeling.

V. Device Description

The Cobas® KRAS Mutation Test consists of two reagent kits and a system platform. Details of the Cobas® 4800

TABLE 13

Mutation assays and cut-offs

| Mutation Assay | 12ALA | 12ASP | 12ARG | 12CYS | 12SER | 12VAL | 13ASP |
|---|---|---|---|---|---|---|---|
| Cut-Off (ΔCt) | ≤8.0 | ≤6.6 | ≤8.0 | ≤8.0 | ≤8.0 | ≤7.5 | ≤7.5 |

VI. Alternative Practices and Procedures

There are several other alternatives for the correction of colorectal cancer: surgery, radiofrequency ablation, cryosurgery, chemotherapy, radiation therapy, and targeted therapy. Each alternative has its own advantages and disadvantages. A patient should fully discuss these alternatives with his/her physician to select the method that best meets expectations and lifestyle.

For the selection of patients who may benefit with Vectibix (panitumumab) targeted therapy, there are no other FDA-cleared or approved alternatives for the testing of colorectal cancer tissue for detecting mutations in the KRAS oncogene.

System platform are described below in "Instrumentation and Software". The reagent kits provide the necessary reagents to perform the two major processes of the test:
1. The Cobas® DNA Sample Preparation kit provides reagents for manual specimen preparation to obtain genomic DNA from formalin-fixed, paraffin-embedded tissue (FFPET).
2. The Cobas® KRAS Mutation Test kit provides reagents for automated real-time PCR amplification and detection of the KRAS mutations.

Specimen Preparation

FFPET specimens are processed and genomic DNA isolated using the Cobas® DNA Sample Preparation Kit, a manual specimen preparation based on nucleic acid binding to glass fibers. A deparaffinized 5 μm section of an FFPET specimen is lysed by incubation at an elevated temperature with a protease and chaotropic lysis/binding buffer that releases nucleic acids and protects the released genomic DNA from DNases. Subsequently, isopropanol is added to the lysis mixture that is then centrifuged through a column with a glass fiber filter insert. During centrifugation, the genomic DNA is bound to the surface of the glass fiber filter. Unbound substances, such as salts, proteins and other cellular impurities, are removed by centrifugation. The adsorbed nucleic acids are washed and then eluted with an aqueous solution. The amount of genomic DNA is spectrophotometrically determined and adjusted to a fixed concentration of 2 ng/µL. Twenty-five (25) µL of the eluate containing 50 ng genomic DNA is combined with 25 µL of each activated master mix reagent, from the Cobas® KRAS Mutation Test kit, in a 96 well plate. Once the controls and samples have been added to the 96 well plate, the plate is transferred to the cobas z 480 analyzer for automated amplification and detection.

PCR Amplification

Target Selection and Amplification

The Cobas® KRAS Mutation Test kit uses primers that define an 85 base pair sequence for exon 2 containing KRAS codons 12 and 13 in human genomic DNA. Amplification occurs only in the region of the KRAS gene between the primers; the entire KRAS gene is not amplified. The intended target mutations are provided in Table 14 below.

TABLE 14

List of Intended Target Mutations for cobas ® KRAS Mutation Test

| Codon | Mutation ID | Nucleotide Change | AA Change | COSMIC ID |
|---|---|---|---|---|
| 12 | c.34G > T | GGT > TGT | G12C | 516 |
|    | c.34G > A | GGT > AGT | G12S | 517 |
|    | c.34G > C | GGT > CGT | G12R | 518 |
|    | c.35G > T | GGT > GTT | G12V | 520 |
|    | c.35G > A | GGT > GAT | G12D | 521 |
|    | c.35G > C | GGT > GCT | G12A | 522 |
| 13 | c.35G > A | GGT > GAC | G12D | 532 |

A derivative of *Thermus* species Z05 DNA polymerase is utilized for target amplification. First, the PCR reaction mixture is heated to denature the genomic DNA and expose the primer target sequences. As the mixture cools, the upstream and downstream primers anneal to the target DNA sequences. The Z05 DNA polymerase, in the presence of a divalent metal ion and excess dNTPs, extends each annealed primer, thus synthesizing a second DNA strand. This completes the first cycle of PCR, yielding a double-stranded DNA copy which includes the targeted 85 base pair region of the KRAS gene. This process is repeated for a number of cycles, with each cycle effectively doubling the amount of amplicon DNA.

Selective amplification of target nucleic acids from the specimen is achieved in the Cobas® KRAS Mutation Test by the use of AmpErase (uracil-N-glycosylase) enzyme and deoxyuridine triphosphate (dUTP). The AmpErase enzyme catalyzes the destruction of DNA strands containing deoxyuridine but not DNA containing thymidine. Deoxyuridine is not present in naturally occurring DNA but is always present in amplicons due to the use of dUTP in place of thymidine triphosphate as one of the nucleotide triphosphates in the Reaction Mix reagent; therefore, only the amplicon contains deoxyuridine. Deoxyuridine renders contaminating amplicons susceptible to destruction by AmpErase enzyme prior to amplification of the target DNA. The AmpErase enzyme is inactive at temperatures above 55° C., i.e., throughout the thermal cycling steps, and therefore does not destroy the target amplicon.

Automated Real-Time Mutation Detection

The cobas z 480 analyzer measures, in real-time, the amount of fluorescence generated by specific PCR products. After amplification, each amplicon generated using the Cobas® KRAS Mutation Test is subjected to a melting program in which the temperature is ramped from 40° C. to 95° C. (TaqMelt). The wild-type specific probe is bound to both the wild-type and mutant amplicon at low temperatures. In the bound state, the fluorescein reporter dye on the 5' end of the probe is sufficiently far away from the 3' end quencher dye, allowing the fluorescent dye to emit a specific wavelength of light. As the temperature rises, the probe dissociates from the amplicon, allowing the quencher dye to come into close proximity to the fluorescent dye, decreasing the amount of measurable fluorescence. An amplicon with a perfect match to the probe (wild-type) melts at a higher temperature than an amplicon with one or more mismatches (mutant). The amount of fluorescence at each temperature increment is measured and the melting temperature(s) are calculated. The presence of a mutant KRAS sequence in codons 12 and 13 can be detected when the melting temperatures are within specified ranges. To avoid detection of codon 12 and codon 13 silent mutations (no amino acid change), a modified base serves as a universal base and produces a melting temperature within the wild-type range.

Instrumentation and Software

The Cobas® 4800 system is controlled by the Cobas® 4800 system SR2.1 software which provides the core software engines and user interfaces. This core system software was designed to allow multiple assays to be performed on the system using analyte specific analysis package software (ASAP). The cobas z 480 analyzer component of the test system also has its own internal instrument control software which is driven by the core software. All of these software components were developed under design control processes and related software standards.

A dedicated Control Unit computer runs the Cobas® 4800 SR2.1 System software and provides an interface to the cobas z 480 and Laboratory Information System (LIS). The computer also processes the fluorescent signals with the ASAP and stores the test results in a controlled database. The complete system allows a user to create a test work order for each specimen manually. A software wizard guides the user through the necessary steps to perform a run which includes cobas z 480 maintenance handling, test selection, specimen ID entry, reagent and microwell plate bar code entry, microwell plate loading and run start.

The Cobas® 4800 System tracks each specimen during processing and analysis on the cobas z 480 analyzer. Once the thermal run is complete the ASAP processes the fluorescence data using data analysis algorithms, assesses the validity of the controls and determines the results using the assay specific result interpretation logic. The software then provides the results to the user in three formats: a printable PDF results report, a Graphical User Interface (GUI) based result viewer and a result export to the LIS. The Cobas® 4800 System software includes a validated KRAS data analysis algorithm to determine sample results and run validity.

Interpretation of Results

Melting temperature (Tm) and peak height (PH) of the melting curves are calculated by the analysis software, and the values from all Mutant control, Negative control, and Calibrator reactions are used to determine if the run is valid. If the run is valid, the analysis software will determine validity and mutation status of the specimens by evaluating the Tm and PH against acceptable ranges of Tm and PH.

Specimens for which a mutant Tm is observed are reported as "Mutation Detected" and the mutant reaction is reported (Table 15). Due to the number of mutations possible and the nature of melting technology, the specific mutation within the codon is not specified.

Specimens for which no mutant Tm is observed are reported as "No Mutation Detected" (Table 15). Specimens for which the codon 12/13 reaction well is invalid are reported as "Invalid". Specimens for which an out-of-range Tm is observed (neither wild-type nor mutant range) are reported as "Invalid". All valid specimens will have at least one melt peak (mutant, wild-type, or both). Specimens with no melt peaks are invalid.

TABLE 15

Result Interpretation of the cobas ® KRAS Mutation Test

| Test Result | cobas ® KRAS Mutation Test Results Mutation Results | Interpretation |
| --- | --- | --- |
| Mutation Detected | Codon 12/13 | Mutation Detected in KRAS Codon 12 or Codon 13 |
| No Mutation Detected | N/A | No Mutation Detetcted in KRAS Codon 12 or 13 |
| Invalid | N/A | Result is inavalid. Repeat the testing of specimens with invalid results following the instructions outlined in the Package Insert |
| Failed | N/A | Failed run due to hardware or software failure |

Test Controls and Calibrator

One KRAS Mutant Control (MC) and one KRAS Negative Control are provided to serve as external run controls. Detection of wild-type codons 12 and 13 by the probe serves as an internal, full process control.

1. KRAS Mutant Control: The Mutant Control is a blend of a double mutant linearized DNA plasmid and genomic DNA from a wild-type cell line. The plasmid contains mutant sequence for KRAS codon 12 (Asp, GAT) and KRAS codon 61 (His, CAC).

The Mutant Control is included in every run and serves as a process control for every step except sample preparation. The Mutant Control reaction must have KRAS wild-type and KRAS codon 12/13 Mutant Melt Temperatures within the respective acceptable ranges for the run to be considered valid.

2. KRAS Negative Control: The Negative Control is a full-process control and serves to identify potential reagent or process contamination for the Cobas® DNA Sample Preparation kit and the Cobas® KRAS Mutation kit. The melt peak height values must be below the pre-established cut-off value for the run to be considered valid. No reagent is provided for the Negative Control. DNA Specimen Diluent (DNA SD) is used as Negative Control.

3. KRAS Calibrator: The KRAS Calibrator consists of wild-type genomic DNA and serves as a melting temperature (Tm) calibrator to compensate for run-to-run and instrument-to-instrument temperature variability. The wild-type peak Tm is used by the analysis software to adjust Tm values of the Mutant Control and all specimens prior to analysis for mutation status.

VI. Alternative Practices and Procedures

There is currently one FDA-approved alternative for testing formalin-fixed, paraffin-embedded CRC tissue for KRAS mutation status in the selection of patients who are eligible for cetuximab (Erbitux) or panitumumab (Vectibix) treatment. Namely, the QIAGEN therascreen KRAS RGQ PCR kit was approved under PMAs P110030 and P110027. FoundationOne Cdx™

I. General Information

Device Generic Name: Next generation sequencing oncology panel, somatic or germline variant detection system
Device Trade Name: FoundationOne CDx™
Device Procode: PQP
Applicant's Name and Address: Foundation Medicine, Inc. 150 Second Street Cambridge, MA 02141
Date(s) of Panel Recommendation: None
Premarket Approval Application (PMA) Number: P170019
Date of FDA Notice of Approval: Nov. 30, 2017
Breakthrough Device: Granted breakthrough device status [previously Expedited Access Pathway (EAP)] on Jun. 15, 2016 because the device (1) is intended to diagnose a life threatening or irreversibly debilitating disease or condition (2) represents a breakthrough technology that provides a clinically meaningful advantage over existing legally marketed technology, and (3) the availability of the device is in the best interest of patients.

II. Indications for Use

FoundationOne CDx™ (F1CDx) is a next generation sequencing based in vitro diagnostic device for detection of substitutions, insertion and deletion alterations (indels) and copy number alterations (CNAs) in 324 genes and select gene rearrangements, as well as genomic signatures including microsatellite instability (MSI) and tumor mutational burden (TMB) using DNA isolated from formalin-fixed paraffin embedded (FFPE) tumor tissue specimens. The test is intended as a companion diagnostic to identify patients who may benefit from treatment with the targeted therapies listed Table 16 in accordance with the approved therapeutic product labeling. Additionally, F1CDx is intended to provide tumor mutation profiling to be used by qualified health care professionals in accordance with professional guidelines in oncology for cancer patients with solid malignant neoplasms. The F1CDx test is a single-site assay performed at Foundation Medicine, Inc.

TABLE 16

Companion diagnostic indications

| Indication | Biomarker | Therapy |
| --- | --- | --- |
| Non-small cell lung cancer (NS CLC) | EGFR exon 19 deletions and EGFR exon 21 L858R alterations | Gilotriif ® (afatinib), Iressa ® (gefitinib), or Tarceva ® (erl otinib) |

TABLE 16-continued

Companion diagnostic indications

| Indication | Biomarker | Therapy |
|---|---|---|
| | EGFR exon 20 T790M alterations | Tagrisso ® (osimertinib) |
| | ALK rearrangements | Alecensa ® (alectinib), Xalkori ® (crizofinib), or Zykadia ® (celitinib) |
| | BRAF V600E | Tafinlar ® (dabrafenib) in combination with Mekinist ® (trametinib) |
| Melanoma | BRAF V600E | Tafinlar ® (dabrafenib) or Zelboraf ® (vemurafenib) |
| | BRAF V600E and V600K | Mekinist ® (trametinib) or Cotellic ® (cobimetinib) in combination with Zelborat ® (vemurafenib) |
| Breast cancer | ERBB2 (HER2) amplification | Herceptin ® (trastuzumab), Kadcyle ® (ado-trastuzumab-emtansine), or Perjeta ® (pertuzumab) |
| Colorectal cancer | KRAS wild-type (absence of mutations in codons 12 and 13) | Erbitux ® (cetuximab) |
| | KRAS (exons 2,3, and 4) and NRAS (exons 2,3, and 4) | Vectibix ® (panitumumab) |
| Ovarian cancer | BRCA1/2 alterations | Rubraca ® (rucaparib) |

III. Contraindications

There are no known contraindications.

IV. Warnings/Precautions and Limitations

The warnings/precautions and limitations are included in the FoundationOne CDx assay labeling.

V. Device Description

FoundationOne CDx (F1CDx) is a single-site assay performed at Foundation Medicine, Inc. The assay includes reagents, software, instruments and procedures for testing DNA extracted from formalin-fixed, paraffin-embedded (FFPE) tumor samples. The assay employs a single DNA extraction method from routine FFPE biopsy or surgical resection specimens, 50-1000 ng of which undergoes whole-genome shotgun library construction and hybridization-based capture of all coding exons from 309 cancer-related genes, 1 promoter region, 1 non-coding RNA (ncRNA), and select intronic regions from 34 commonly rearranged genes, 21 of which also include the coding exons (refer to Table 17 and Table 18 below for complete list of genes included in F1CDx). In total, the assay therefore detects alterations in a total of 324 genes. Using the Illumine® Hi Seq 4000 platform, hybrid-capture-selected libraries will be sequenced to high uniform depth (targeting >500× median coverage with >99% of exons at coverage >100×). Sequence data is processed using a customized analysis pipeline designed to detect all classes of genomic alterations, including base substitutions, indels, copy number alterations (amplifications and homozygous deletions), and selected genomic rearrangements (e.g., gene fusions). Additionally, genomic signatures including microsatellite instability (MSI) and tumor mutational burden (TMB) will be reported.

TABLE 17

Genes with full coding exonic regions included in F1CDs for the detection of substitutions, insertion-deletions (indels), and copy number alterations (CNAs)

| ABL1 | BRAF | CDKN1A | EPHA3 | FGFR4 | IKZF1 | MCL1 | NKX2-1 | PMS2 | RNF43 | TET2 |
|---|---|---|---|---|---|---|---|---|---|---|
| ACVR1B | BRCA1 | CDKN1B | EPHB1 | FH | INPP4B | MDM2 | NOTCH1 | POLD1 | ROS1 | TGFBR2 |
| AKT1 | BRCA2 | CDKN2A | EPHB4 | FLCN | IRF2 | MDM4 | NOTCH2 | POLE | RPTOR | TIPARP |
| AKT2 | BRD4 | CDKN2B | ERBB2 | FLT1 | IRF4 | MED12 | NOTCH3 | PPARG | SDHA | TNFAIP3 |
| AKT3 | BRIP1 | CDKN2C | ERBB3 | FLT3 | IRS2 | MEF2B | NPM1 | PPP2R1A | SDHB | TNFRSF14 |
| ALK | BTG1 | CEBPA | ERBB4 | FOXL2 | JAK1 | MEN1 | NRAS | PPP2R2A | SDHC | TP53 |
| ALOX12B | BTG2 | CHEK1 | ERCC4 | FUBP1 | JAK2 | MERTK | NT5C2 | PRDM1 | SDHD | TSC1 |
| AMER1 | BTK | CHEK2 | ERG | GABRA6 | JAK3 | MET | NTRK1 | PRKAR1A | SETD2 | TSC2 |
| APC | C11orf30 | CIC | ERRF11 | GATA3 | JUN | MITF | NTRK2 | PRKCI | SF3B1 | TYRO3 |
| AR | CALR | CREBBP | ESR1 | GATA4 | KDM5A | MKNK1 | NTRK3 | PTCH1 | SGK1 | U2AF1 |
| ARAF | CARD11 | CRKL | EZH2 | GATA6 | KDM5C | MLH1 | P2RY8 | PTEN | SMAD2 | VEGFA |
| ARFRP1 | CASP8 | CSF1R | FAM46C | GID4 (C17orf39) | KDM6A | MPL | PALB2 | PTPN11 | SMAD4 | VHL |
| ARID1A | CBFB | CSF3R | FANCA | GNA11 | KDR | MRE11A | PARK2 | PTPRO | SMARCA4 | WHSC1 |
| ASXL1 | CBL | CTCF | FANCC | GNA13 | KEAP1 | MSH2 | PARP1 | QKI | SMARCB1 | WHSC1L1 |
| ATM | CCND1 | CTNNA1 | FANCG | GNAQ | KEL | MSH3 | PARP2 | RAC1 | SMO | WT1 |
| ATR | CCND2 | CTNNB1 | FANCL | GNAS | KIT | MSH6 | PARP3 | RAD21 | SNCAIP | XPO1 |
| ATRX | CCND3 | CUL3 | FAS | GRM3 | KLHL6 | MST1R | PAX5 | RAD51 | SOCS1 | XRCC2 |
| AURKA | CCNE1 | CUL4A | FBXW7 | GSK3B | KMT2A (MLL) | MTAP | PBRM1 | RAD51B | SOX2 | ZNF217 |

TABLE 17-continued

Genes with full coding exonic regions included in F1CDs for the detection of substitutions, insertion-deletions (indels), and copy number alterations (CNAs)

| AURKB | CD22 | CXCR4 | FGF10 | H3F3A | KMT2D (MLL2) | MTOR | PDCD1 | RAD51C | SOX9 | ZNF703 |
|---|---|---|---|---|---|---|---|---|---|---|
| AXIN1 | CD274 | CYP17A1 | FGF12 | HDAC1 | KRAS | MUTYH | PDCD1LG2 | RAD51D | SPEN | |
| AXL | CD70 | DAXX | FGF14 | HGF | LTK | MYC | PDGFRA | RAD52 | SPOP | |
| BAP1 | CD79A | DDR1 | FGF19 | HNF1A | LYN | MYCL | PDGFRB | RAD54L | SRC | |
| BARD1 | CD79B | DDR2 | FGF23 | HRAS | MAF | MYCN | PDK1 | RAF1 | STAG2 | |
| BCL2 | CDC73 | DIS3 | FGF3 | HSD3B1 | MAP2K1 | MYD88 | PIK3C2B | RARA | STAT3 | |
| BCL2L1 | CDH1 | DNMT3A | FGF4 | ID3 | MAP2K2 | NBN | PIK3C2G | RB1 | STK11 | |
| BCL2L2 | CDK12 | DOT1L | FGF6 | IDH1 | MAP2K4 | NF1 | PIK3CA | RBM10 | SUFU | |
| BCL6 | CDK4 | EED | FGFR1 | IDH2 | MAP3K1 | NF2 | PIK3CB | REL | SYK | |
| BCOR | CDK6 | EGFR | FGFR2 | IGF1R | MAP3K13 | NFE2L2 | PIK3R1 | RET | TBX3 | |
| BCORL1 | CDK8 | EP300 | FGFR3 | IKBKE | MAPK1 | NFKBIA | PIM1 | RICTOR | TEK | |

TABLE 18

Genes with select intronic regions for the detection of gene rearrangements, a promoter region, and ncRNA gene

| ALK introns 18, 19 | BRCA1 introns 2, 7, 8, 12, 16, 19, 20 | ETV4 introns 5, 6 | EZR introns 9-11 | KIT intron 16 | MYC intron 1 | NUTM1 intron 1 | RET introns 7-11 | SLC34A2 intron 4 |
|---|---|---|---|---|---|---|---|---|
| BCL2 3'UTR | BRCA2 intron 2 | ETV5 introns 6, 7 | FGFR1 intron 1, 5, 17 | KMT2A (MLL) introns 6-11 | NOTCH2 intron 26 | PDGFRA introns 7, 9, 11 | ROS1 introns 31-35 | TERC ncRNA |
| BCR introns 8, 13, 14 | CD74 introns 6-8 | ETV6 introns 5, 6 | FGFR2 intron 1, 17 | MSH2 intron 5 | NTRK1 introns 8-10 | RAF1 introns 4-8 | RSPO2 intron 1 | TERT Promoter |
| BRAF introns 7-10 | EGFR introns 7, 15, 24-27 | EWSR1 introns 7-13 | FGFR3 intron 17 | MYB intron 14 | NTRK2 Intron 12 | RARA intron 2 | SDC4 intron 2 | TMPRSS2 introns 1-3 |

Test Output

The output of the test includes:

Category 1: CDx Claims noted in Table 16 of the Intended Use

Category 2: Cancer Mutations with Evidence of Clinical Significance

Category 3: Cancer Mutations with Potential Clinical Significance

Genomic findings other than those listed in Table 16 of the intended use statement (i.e., Categories 2 and 3) are not prescriptive or conclusive for labeled use of any specific therapeutic product.

Test Kit Contents

The test includes a sample shipping kit, which is sent to ordering laboratories. The shipping kit contains the following components:

Specimen Preparation Instructions
Shipping Instructions
Return Shipping Label

Instruments

The F1CDx assay is intended to be performed with serial number-controlled instruments as indicated in Table 19, below. All instruments are qualified by Foundation Medicine, Inc. (FMI) under FMI's Quality System.

TABLE 19

Instruments for use with the F1CDx assay Instrument

Illumina HiSeq 4000
Illumina cBot

TABLE 19-continued

Instruments for use with the F1CDx assay Instrument

Beckinan Biornck NXP Span-8 Liquid Handler
Thermo Scientific Kingfisher Flex DW 96

Test Process

All assay reagents included in the F1CDx assay process are qualified by FMI and are compliant with the medical device Quality System Regulation (QSR).

A. Specimen Collection and Preparation

Formalin-fixed, paraffin-embedded (FFPE) tumor specimens are collected and prepared following standard pathology practices. FFPE specimens may be received either as unstained slides or as an FFPE block.

Prior to starting the assay, a Hematoxylin and Eosin (H&E) stained slide is prepared, and then reviewed by a board-certified pathologist to confirm disease ontology and to ensure that adequate tissue (0.6 mm$^3$), tumor content (≥20% tumor) and sufficient nucleated cells are present to proceed with the assay.

B. DNA Extraction

Specimens passing pathology review are queued for DNA extraction which begins with lysis of cells from FFPE tissue by digestion with a proteinase K buffer followed by automated purification using the 96-well KingFisher™ FLEX Magnetic Particle Processor.

After completion of DNA extraction, double-stranded DNA (dsDNA) is quantified by the Quant-iT™ PicoGreen® fluorescence assay using the provided lambda DNA standards (Invitrogen) prior to Library Construction (LC). The sample must yield a minimum of 55 ng of genomic DNA to ensure sufficient DNA for quality control (QC) and to proceed with LC.

C. Library Construction

Library Construction (LC) begins with the normalization of DNA to 50-1000 ng. The normalized DNA samples are randomly sheared (fragmented) to ~200 bp by adaptive focused acoustic sonication using a Covaris LE220 before purification using a 1.8× volume of AMPure® XP Beads (Agencourt®). Solid-phase reversible immobilization (SPRI) purification and subsequent library construction with the NEBNext® reagents (custom-filled kits by NEB), including mixes for end repair, dA addition and ligation, are performed in 96-well plates (Eppendorf) on a Bravo Benchbot (Agilent) using the "with-bead" protocol to maximize reproducibility and library yield. Indexed (6 bp barcodes) sequencing libraries are PCR amplified with HiFi™ (Kapa) for 10 cycles, and subsequently 1.8×SPRI purified. Purification and dilution for QC are performed.

Following LC, a QC procedure is performed by quantifying single-stranded DNA (ssDNA) from purified libraries using the Quant-iT™ OliGreen® ssDNA Assay Kit (Life Technologies) read on a Molecular Devices Multimode SpectraMax M2 plate Reader. Libraries yielding insufficient sequencing library are failed.

D. Hybrid Capture

Hybrid Capture (HC) begins with normalization of each library to 500-2000 ng. Normalized samples then undergo solution hybridization which is performed using a >50-fold molar excess of a pool of individually synthesized 5'-biotinylated DNA 120 bp oligonucleotides. The baits target ~1.8 Mb of the human genome including all coding exons of 309 cancer-related genes, introns or non-coding regions of 35 genes, plus >3,500 single nucleotide polymorphisms (SNPs) located throughout the genome. Baits are designed by tiling overlapping 120 bp DNA sequence intervals covering target exons (60 bp overlap) and introns (20 bp overlap), with a minimum of three baits per target; SNP targets are allocated one bait each. Intronic baits are filtered for repetitive elements as defined by the UCSC Genome RepeatMasker track.

After hybridization, the library-bait duplexes are captured on paramagnetic MyOne™ streptavidin beads (Invitrogen) and off-target material is removed by washing one time with 1×SSC at 25° C. and four times with 0.25×SSC at 55° C. The PCR master mix is added to directly amplify (12 cycles) the captured library from the washed beads. 3 After 12 cycles of amplification, the samples are 1.8×SPRI purified. Purification and dilution for QC are performed.

Quality Control for Hybrid Capture is performed by measuring dsDNA yield using a Quant-iT™ PicoGreen® dsDNA Assay Kit (Life Technologies) read on a Molecular Devices Multimode SpectraMax M2 plate Reader. Captured libraries yielding less than 140 ng of sequencing library are failed.

E. Sequencing

Sequencing is performed using off-board clustering on the Illumina cBot with patterned flow cell technology to generate monoclonal clusters from a single DNA template followed by sequencing using sequencing by synthesis (SBS) chemistry on the Illumina HiSeq 4000. Fluorescently labeled 3'-blocked dNTP's along with a polymerase are incorporated through the flow cell to create a growing nucleotide chain that is excited by a laser. A camera captures the emission color of the incorporated base and then is cleaved off. The terminator is then removed to allow the nucleotide to revert to its natural form and to allow the polymerase to add another base to the growing chain. A new pool of fluorescently labeled 3'-blocked dNTPs are added with each new sequencing cycle. The color changes for each new cycle as a new base is added to the growing chain. This method allows for millions of discrete clusters of clonal copies of DNA to be sequenced in parallel.

F. Sequence Analysis

Sequence data is analyzed using proprietary software developed by FMI. Sequence data is mapped to the human genome (hg19) using Burrows-Wheeler Aligner (BWA) v0.5.9. PCR duplicate read removal and sequence metric collection is performed using Picard 1.47 (http://picard.sourceforge.net) and SAMtools 0.1.12a. Local alignment optimization is performed using Genome Analysis Toolkit (GATK) 1.0.4705. Variant calling is performed only in genomic regions targeted by the test.

Base substitution detection is performed using a Bayesian methodology, which allows for the detection of novel somatic alterations at low mutant allele frequency (MAF) and increased sensitivity for alterations at hotspot sites through the incorporation of tissue-specific prior expectations. Reads with low mapping (mapping quality <25) or base calling quality (base calls with quality≥2) are discarded. Final calls are made at MAF≥5% (MAF≥1% at hotspots).

To detect indels, de novo local assembly in each targeted exon is performed using the de-Bruijn approach. Key steps are:

Collecting all read-pairs for which at least one read maps to the target region.

Decomposing each read into constituent k-mers and constructing an enumerable graph representation (de-Bruijn) of all candidate non-reference haplotypes present.

Evaluating the support of each alternate haplotype with respect to the raw read data to generate mutational candidates. All reads are compared to each of the candidate haplotypes via ungapped alignment, and a read 'vote' for each read is assigned to the candidate with best match. Ties between candidates are resolved by splitting the read vote, weighted by the number of re ads already supporting each haplotype. This process is iterated until a 'winning' haplotype is selected.

Aligning candidates against the reference genome to report alteration calls.

Filtering of indel candidates is carried out similarly to base substitutions, with an empirically increased allele frequency threshold at rep eats and adjacent sequence quality metrics as implemented in GA TK: % of neighboring bases mismatches<25%, average neighboring base quality>25, average number of supporting read mismatches≤2. Final calls are made at MAF≥5% (MAF 3% at hotspots).

Copy number alterations (CNAs) are detected using a comparative genomic hybridization (CGH)-like method. First, a log-ratio profile of the sample is acquired by normalizing the sequence coverage obtained at all exons and genome-wide SNPs (~3,500) against a process-matched normal control. This profile is segmented and interpreted using allele frequencies of sequenced SNPs to estimate tumor purity and copy number at each segment. Amplifications are called at segments with ≥6 copies (or ≥7 for triploid/≥8 for tetraploid tumors) and homozygous deletions at 0 copies, in samples with tumor purity ≥20%. Amplifications in ERBB2 are called positive at segments with ≥5 copies for diploid tumors.

Genomic rearrangements are identified by analyzing chimeric read pairs. Chimeric read pairs are defined as read pairs for which reads map to separate chromosomes, or at a distance of over 10 megabase (Mb). Pairs are clustered by genomic coordinate of the pairs, and clusters containing at least five (5) chimeric pairs [three (3) for known fusions] are identified as rearrangement candidates. Filtering of candidates is performed by mapping quality (average read mapping quality in the cluster must be 30 or above) and distribution of alignment positions. Rearrangements are annotated for predicted function (e.g., creation of fusion gene).

To determine microsatellite instability (MSI) status, 95 intronic homopolymer repeat loci (10-20 bp long in the human reference genome) with adequate coverage on F1CDx Assay are analyzed for length variability and compiled into an overall MSI score via principal components analysis. Using the 95 loci, for each sample the repeat length is calculated in each read that spans the locus. The means and variances of repeat lengths is recorded. Principal components analysis (PCA) is used to project the 190-dimension data onto a single dimension (the first principal component) that maximizes the data separation, producing an MSI score. Each sample is assigned a qualitative status of MSI-High (MSI-H) or MSI-Stable (MSS); ranges of the MSI score are assigned MSI-H or MSS by manual unsupervised clustering. Samples with low coverage (<250× median) are assigned a status of MSI-unknown.

Tumor mutational burden (TMB) is measured by counting all synonymous and nonsynonymous variants present at 5% allele frequency or greater, and filtering out potential germline variants according to published databases of known germline polymorphisms including Single Nucleotide Polymorphism database (dbSNP) and Exome Aggregation Consortium (ExAC). Additional germline alterations still present after database querying are assessed for potential germline status and filtered out using a somatic-germline/zygosity (SGZ) algorithm. Furthermore, known and likely driver mutations are filtered out to exclude bias of the data set. The resulting mutation number is then divided by the coding region corresponding to the number of total variants counted, or 793 kb. The resulting number is communicated as mutations per Mb unit (mut/Mb).

After completion of the Analysis Pipeline, variant data is displayed in the FMI custom-developed CATi software applications with sequence quality control metrics. As part of data analysis QC for every sample, the F1CDx assay assesses cross-contamination through the use of a SNP profile algorithm reducing the risk of false-positive calls that could occur as a result of an unexpected contamination event. Sequence data is reviewed by trained bioinformatics personnel. Samples failing any QC metrics are automatically held and not released.

G. Report Generation

Approved results are annotated by automated software with CDx relevant information and are merged with patient demographic information and any additional information provided by FMI as a professional service prior to approval and release by the laboratory director or designee.

H. Internal Process Controls Related to the System

Positive Control

Each assay run includes a control sample run in duplicate. The control sample contains a pool of ten HapMap cell lines and is used as a positive mutation detection control. One hundred (100) different germline SNPs present across the entire targeted region are required to be detected by the analysis pipeline. If SNPs are not detected as expected, this results in a QC failure as it indicates a potential processing error.

Sensitivity Control

The HapMap control pool used as the positive control is prepared to contain variants at 5%-10% MAF which must be detected by the analysis pipeline to ensure expected sensitivity for each run.

Negative Control

Samples are barcoded molecularly at the LC stage. Only reads with a perfect molecular barcode sequence are incorporated into the analysis. The Analysis Pipeline includes an algorithm that analyzes the SNP profile of each specimen to identify potential contamination that may have occurred prior to molecular barcoding, and can detect contamination lower than 1%.

VI. Alternative Practices and Procedures

There are FDA approved companion diagnostic (CDx) alternatives for the detection of genetic alterations using FFPE tumor specimens, as listed in Table 16 of the F1CDx intended use statement. The approved CDx tests are listed in Table 20 below; for additional details see FDA List of Cleared or Approved Companion Diagnostic Devices at https://www.fda.gov/MedicalDevices/ProductsandMedicalProcedures/InVitroDiagnostics/ucm301431.htm?source=govdelivery.

TABLE 20:

| | | | | | |
|---|---|---|---|---|---|
| List of FDA approved CDx assays for genes targeted by F1CDx | | | | | |
| | Device | Company | Technology | Therapy | Indication |
| HER2-Amplification | PathVysion HER-2 DNA Probe Kit | Abbott Molecular, Inc. | FISH | Herceptin (trastuzumab) | Breast cancer |
| | Pathway Anti-HER-2/neu (4B5) Rabbit Monoclonal Primary Antibody | Ventana Medical Systems, Inc. | IEIC | Herceptin (trastuzumab) | Breast cancer |
| | Insite HER-2/neu Kit | Biogenex Laboratori es, Inc. | IHC | Herceptin (trastuzumab) | Breast cancer |
| | Spot-Light HER2 CISH Kit | Life Technologies, Inc. | CISH | Herceptin (trastuzumab) | Breast cancer |
| | Bond Oracle Her2 IHC System | Leica Biosystems | IHC | Herceptin (trastuzumab) | Breast cancer |
| | HER2 CISH pharmDx Kit | Dako Denmark A/S | CISH | Herceptin (trastuzumab) | Breast cancer |

TABLE 20:-continued

List of FDA approved CDx assays for genes targeted by F1CDx

| | Device | Company | Technology | Therapy | Indication |
|---|---|---|---|---|---|
| | INFORM HER2 DUAL ISH DNA Probe Cocktail | Ventana Medical Systems, Inc. | Dual ISH | Herceptin (tratuzumab) | Breast cancer |
| | HercepTest | Dako Denmark A/S | IHC | Herceptin (trastuzumab) Perjeta (pertuzumab) Kadcyla (ado-trastuzumab emtansine) | Breast cancer Gastric or Gastroesophageal junction adenocarcinoma |
| | HIER2 FISH pharmDx Kit | Dako Denmark A/S | FISH | Herceptin (trastuzumab) Perjeta (pertuzumab) Kadcyla (ado-trastuzumab emtansine) | Breast cancer Gastric Of Gastroesophageal junction adenocarcinoma |
| BRAF-V600 | THxlID BRAF Kit | bioMerieux | PCR | Mekinist (tramatenib) | Melanoma |
| | cobas BRAF V600 Mutation Test | Roche Molecular Systems, Inc. | PCR | Zelboraf (vemurafenib) | Melanoma |
| BRAF-00E | THxlID BRAF Kit | bioMerieux | PCR | Tafinlar (dabrafenib) | Melanoma |
| | Oncomine Dx Target Test | Life Technologies, Inc. | NGS | Tafinlar (dabrafernib) Mekinist (trametinib) | Non-small cell lung cancer |
| NRAS | Praxis Extended Ras Panel | Illumina | NGS | Vectibix (panitumumab) | Colorectal cancer |
| KRAS | cobas KRAS Mutation Test | Roche Molecular Systems, Inc | PCR | Erbitux (cetuximab) Vectibix (panitumumab) | Colorectal cancer |
| | therascreen KRAS RGQ PCP Kit | QIAGEN | FCR | Erbitux (cetuximab) Vectibix (panitumumab) | Colorectal cancer |
| | Praxis Extended Ras Panel | Illumlna | NGS | Vectibix (panitumumab) | Colorectal cancer |
| ALK - fusion | Vysis ALK Break Apart FISH Probe Kit | Abbot Molecular, Inc. | FISH | Xalkori (crizotinib) | Non-small cell lung cancer |
| | ALK (D5F3) CDx Assay | Vontona Medical Systems, Inc. | IHC | Xalkori (crizotinib) | Non-small ccil lung cancer |
| EGFR - Exon 19 deletions & L858R | cobasEGFR Mutation Test v2 | Roche Molecular Systems, Inc. | PCR | Tarceva (erlotinib) | Non-small cell lung cancer |
| | therascreen EGFR RGQ PCR Kit | QIAGEN | PCR | Gilotrif (afatinib) Iressa (gefitinib) | Non-small cell lung cancer |
| | Oncoraine Dx Target Test | Lite Technologies, Inc. | NGS | Iressa (getitinib lung cancer | Non-small cell |
| EGFR T790M | cobas EGFR Mutation Test v2 | Roche Molecular Systems, Inc. | PCR | Tagrisso (osimertinib) | Non-small cell lung cancer |
| BRCA1/2 | FoundationFocus CDx$_{BRCA}$ | Foundation Medicine, Inc. | NGS | Rubraca (rucaparib) | Advanced Ovarian |

Abbreviations:
FISH—fluorescence in situ hybridization;
IHC—immunohistochemistry;
CISH—chromogenic in situ hybridization;
ISH—in situ hybridization;
PCR—polymerase chain reaction;
NGS—next generation sequencing.

VII. Marketing History

Foundation Medicine, Inc. initially designed and developed the FoundationOne® laboratory developed test (F1 LDT), and the first commercial sample was tested in 2012. The F1 LDT has been used to detect the presence of genomic alterations in FFPE tumor tissue specimens. The F1 LDT is not FDA-cleared or -approved.

The F1CDx assay has not been marketed in the United States or any foreign country.

Therascreen® KRAS RGQ PCR Kit (2012)

I. General Information

Device Generic Name: Real-time PCR test
Device Trade Name: Therascreen® KRAS RGQ PCR Kit
Device Procode: OWD
Applicant's Name and Address: QIAGEN Manchester Ltd. Skelton House, Lloyd Street North Manchester, UK M15 6SH
Date(s) of Panel Recommendation: None
Premarket Approval Application (PMA) Number: P110030
Date of FDA Notice of Approval: Jul. 6, 2012
Expedited: Not applicable

II. Indications for Use

The therascreen KRAS RGQ PCR Kit is a real-time qualitative PCR assay used on the Rotor-Gene Q MDx instrument for the detection of seven somatic mutations in the human KRAS oncogene, using DNA extracted from formalin-fixed paraffin-embedded (FFPE), colorectal cancer (CRC) tissue. The therascreen KRAS RGQ PCR Kit is intended to aid in the identification of CRC patients for treatment with Erbitux® (cetuximab) based on a KRAS no mutation detected test result.

III. Contraindications

None.

IV. Warnings and Precautions

The warnings and precautions can be found in the Therascreen® KRAS RGQ PCR Kit labeling.

V. Device Description

The following components comprise the overall device:
QIAGEN QIAamp® DSP DNA FFPE Tissue Kit
QIAGEN Therascreen® KRAS RGQ PCR Kit
QIAGEN Rotor-Gene Q MDx, Software version 2.1.0, and KRAS Assay Package Specimen Preparation Formalin-fixed, paraffin-embedded (FFPE) blocks are sectioned onto glass slides. A stained slide is used to confirm that the tumor content exceeds 20% of the tissue and that a minimum tumor area of 4 mm$^2$ is available. A single non-stained tissue section is scraped from the slide for DNA extraction. If sections have a tumor content of less than 20%, the section should be macrodissected. DNA is manually extracted and! purified from 5 μm glass-mounted sections of FFPE tissue taken from colorectal cancer patients using the QIAGEN QIAamp® DSP DNA FFPE Tissue Kit and a modified protocol. The tumor tissue is deparaffinized with xylene and the xylene is extracted with ethanol. The sample is lysed under denaturing conditions with proteinase K for one hour. The sample is heated at 90° C. to reverse formalin cross-linking of genomic DNA. The sample is passed through a silica-based membrane so that genomic DNA binds to the membrane and contaminants are removed. Purified genomic DNA is eluted from the membrane into 200 μL of elution buffer. Extracted DNA is stored at −20° C.

PCR Amplification and Detection

The QIAGEN Therascreen® KRAS RGQ PCR Kit contains reagents for eight separate reactions; seven mutation specific reactions to amplify and detect mutations in codons 12 and 13 in exon 2 of the K-Ras oncogene, and one Control Reaction that amplifies and detects a region of exon 4 in the K-Ras oncogene. Each reaction in the KRAS RGQ Kit makes use of an amplification refractory mutation system (ARMS®) allele specific polymerase chain reactions (PCR) to selectively amplify mutated genomic DNA templates (mutation-positive) in a background of non-mutated genomic DNA (mutation-negative; wild-type) combined with a fluorophore-labeled Scorpion® primer to detect any resultant amplification product. ARMS technology exploits the ability of Taq polymerase to distinguish between a match and a mismatch at the 3' end of a PCR primer. Scorpions are bifunctional molecules containing a PCR primer covalently linked to a probe. The probes incorporate both a fluorophore, [carboxyfluorescein (FAM™)] and a quencher which quenches the fluorescence of the fluorophore. During PCR, when the probe binds to the ARMS amplicon, the fluorophore and quencher become separated leading to a detectable increase in fluorescence.

Before testing with the mutation-specific test reactions, each DNA sample must be tested with the Control Reaction to determine whether the quality and quantity of DNA is sufficient and appropriate for the working range of the assay. The Control Reaction Ct value is used to assess the total amplifiable DNA in a sample and must fall within prespecified ranges for each sample.

The interpretation of the results obtained from the Control reaction is as follows:

TABLE 21

Interpretation of the results obtained from the Control reaction

| Control Ct value | Interprotation | Action |
| --- | --- | --- |
| >32.00 | Quantity of amplifiable DNA is not sufficientfor mutation analysis. | Additional samples should be extracted and tested |
| <21.92 | Quantity of amplifiable DNA is too high for mutation analysis. | Dilute with the sample diluent water supplied in the kit |
| 21.92 ≤ Control Ct ≥ 32.00 | Quantity of amplifiable DNA is suitable for mutation analysis | — |

The run parameters used for assessing the DNA sample with the Control Reaction mix are the same run parameters for mutation analysis using the Mutation Reaction mixes. The run parameters are: (1) Hold at 95° C. for 15 minutes to activate the Taq polymerase; (2) PCR for 40 cycles of 95° C. for 30 seconds, to denature, and 60° C. for 1 minute, to anneal/extend. The PCR cycle at which the fluorescence from a particular reaction crosses the pre-defined threshold value is defined as the Ct value. The seven mutations in codons 12 and 13 of the K-RAS oncogene detected by the Kit are listed below:

TABLE 22 seven mutations in codons 12 and 13 of the K-RAS oncogene detected by the Kit

| Mutation | Base Change |
|---|---|
| GLY12ALA (G12A) | GGT > GCT |
| GLY12ASP (G12D) | GGT > GAT |
| GLY12ARG (G12R) | GGT > CGT |
| GLY12CYS (G12C) | GGT > TGT |
| GLY12SER (G12S) | GGT > AGT |
| GLY12VAL (G12V) | GGT > GTT |
| GLY12ASP (G12D) | GGT > GAC |

Test Controls

Each test run must contain an Internal Control, the Positive Control, and the Negative Control. A test run is considered invalid if the Negative Control indicates that the test run has been contaminated (Ct value above a set value for the FAM channel) or if the Positive Control Ct value lies outside a set range (both FAM and HEX channels).

TABLE 23

Run Validity Criteria

| Reaction | Sample | RGQ Channel | Valid Ct Range |
|---|---|---|---|
| Control | Positive Control | FAM | 23.50 to 29.50 |
| Control | No Template Control | FAM | No amplification |
| Control | No Template Control | HEX | 31.90 to 35.16 |
| Mutation | Positive Control | FAM | 23.50 to 29.50 |
| Mutation | No Template Control | FAM | No amplification |
| Mutation | No Template Control | HEX | 31.91 to 35.16 |

*Ranges are inclusive

Internal Control:

All eight reactions contain an additional ARMS primer and a HEX-labeled Scorpion primer for the amplification and detection of a synthetic non K-Ras related oligonucleotide template that is used as an Internal Control. The Scorpion primer is labeled with HEX to distinguish from the FAM-labeled Scorpions in the control and mutation reactions. In each reaction, the Internal Control reaction is designed to be the weaker of the two reactions. This is achieved through the use of a very low concentration of Internal Control template. The Internal Control reaction is designed to work independently of mutation-specific amplification, but can fail in the presence of strong amplification if it is "out-competed" by the FAM reaction. A mutation negative result with a failed Internal Control reaction in any one of the seven mutation reactions will be reported as an invalid result. The Internal Control is used to detect inhibitors or gross reaction failures.

Positive Control:

The positive control is comprised of a mixture of synthetic oligonucleotides representing each of the mutations detected by the KRAS Kit. Detection of the positive control confirms the proper functioning of each of the reaction mixes in the Kit.

Negative Control:

The KRAS RGQ Kit contains nuclease-free water to be used as a no template control (NTC) reaction. The NTC serves as a negative control and assesses potential contamination during assay set up.

Instrument and Software

The Rotor-Gene Q (RGQ) MDx Instrument is a real-time PCR analyzer designed for thermocycling and real-time detection of amplified DNA. The RGQ MDx Instrument controls and monitors PCR reactions and includes the software that determines mutation status based upon PCR results. It incorporates a centrifugal rotor design for thermal cycling during PCR reactions where each tube spins in a chamber of moving air. Samples are heated and cooled in a low-mass-air oven according to a software determined cycle that initiates the different phases of the PCR cycle for a total of 40 cycles for each PCR run. In the RGQ MDx Instrument, samples are excited from the bottom of the chamber by a light emitting diode. Energy is transmitted through the thin walls at the base of the tube. Emitted fluorescence passes through the emission filters on the side of the chamber and is detected by a photomultiplier tube. Detection is performed as each tube aligns with the detection optics; tubes spin past the excitation/detection optics every 150 milliseconds. The fluorescence signals monitor the progress of the PCR reactions. The instrument is capable of supporting up to six optical channels (six excitation sources and six detection filters), however only two of these channels (the FAM and HEX channels) are used with the KRAS Kit.

The therascreen KRAS Assay Package consists of two templates: the "therascreen KRAS QC Locked Template" (for DNA sample assessment) and the "therascreen KRAS Locked Template" (for detection of KRAS mutations). These templates contain the PCR run parameters and calculate the results. The same run parameters are used for both the DNA sample assessment with the Control Reaction Mix and for detection of KRAS mutations using the mutation reaction mixes.

The RGQ MDx Instrument software supports real-time analysis procedures. The software determines Ct values, calculates ΔCt values, and compares these to the mutation-specific cut-off values incorporated into the software as described above. A system of Flags/Warnings is embedded within the software in order to inform the user of potential problems with the assay and to indicate non-valid test runs or non-valid samples within a valid test run (inappropriate level of DNA or Internal Control failure). No results are reported for invalid runs or for non-valid samples. Users of the KRAS RGQ Kit cannot make subjective determinations of mutation status as they do not have access to the Ct or ΔCt values and only see the mutation status calls reported by the software.

Interpretation of Results

The Ct for the control reaction reflects the total amount of amplifiable K-Ras template in the sample, while the Ct for the allele specific reactions reflect the amount of K-Ras mutation within the sample. The difference in Ct values (ΔCt) between the control reaction and the allele-specific reaction indicates the proportion of mutation within the sample. The ΔCt value approaches 0 as the proportion of mutant DNA in the samples increases. The ΔCt value increases (approaches the threshold for positive vs. negative call) as the proportion of mutant DNA in the sample decreases. When the ΔCt measure exceeds ΔCt cut-off values for the mutant reactions, the assay reports no mutation detected (e.g., negative for the 7 mutations).

For each sample, a calculation is performed by the RGQ MDx Instrument software to determine the ΔCt value (FAM channel) for each of the 7 mutation-specific reactions:

$$[\text{Mutation reaction } Ct \text{ value}] - [\text{Control Reaction } Ct \text{ value}] = \Delta Ct$$

Based on pre-determined analytical Ct and ΔCt values, the Rotor-Gene Q software qualitatively determines the mutation status of the DNA samples and reports which samples contain which mutation. Each sample will have seven possible ΔCt values (one per mutation). These values are compared to pre-established specifications (cut-off values) incorporated into the RGQ MDx Instrument software to determine whether a sample is mutation positive or negative and which mutation, if any, is present. When the mutation reaction ΔCt value is less than or equal to the cut-off value for that reaction, the sample is K-Ras mutation-positive. The assay results will be displayed as "Mutation Positive," "No Mutation Detected," "Invalid" or, if a run control fails, "Run Control Failed." For the mutation-positive samples, specific mutations are reported.

TABLE 24

Mutation assays and cut-offs

| Mutation Assay | 12ALA | 12ASP | 12ARG | 12CYS | 12SER | 12VAL | 13ASP |
|---|---|---|---|---|---|---|---|
| Cut-Off (ΔCt) | ≤8.0 | ≤6.6 | ≤8.0 | ≤8.0 | ≤8.0 | ≤7.5 | ≤7.5 |

VI. Alternative Practices and Procedures

There are no other FDA-cleared or approved alternatives for the testing of colorectal cancer tissue for detecting mutations in the K-Ras oncogene for the selection of patients who may benefit with Erbitux® (cetuximab) therapy.

Detection Kit (Roche Diagnostics Deutschland GmbH) on Discovery® XT. Detailed staining procedures are e.g described in: Goodman S L, Grote H J, Wilm C. Matched rabbit monoclonal antibodies against αv-series integrins reveal a novel αvβ3-LIBS epitope, and permit routine staining of archival paraffin samples of human tumors. Biol Open 2012; 1: 329-340. Afterwards the slides were manually washed using hot water supplemented with detergent, followed by tap water only and dH2O in a final step. For dehydration, the slides were transferred to an ascending ethanol series (2×80%, 2×96%, 2×abs. EtOH) and incubated for 1-3 min, respectively. After dehydration, the slides were transferred to xylene (3×2 min) and finally automatically embedded in Pertex.

4.1.1 Anti-Integrin αvβ6
4.1.1.1 Anti-Integrin αvβ6 Antibody and Isotype Control

TABLE 25

Anti-Integrin αvβ6 antibody and isotype control

| Name | Clone | Provider | Host species | Stock conc. | Working dilution |
|---|---|---|---|---|---|
| Anti-Integrin αvβ6 | EM05201 | Merck Serono | Rabbit | 1.0 mg/ml | 1:2000 |
| Rabbit IgG | DA1E | Coll Gignaling Technology | Rabbit | 2.5 mg/ml | 1:5000 |

Example 4: Determination of High αvβ6 Integrin Expression Status

4. Method 4.1 Immunohistochemistry

Immunohistochemistry of FFPE tissues was performed using antibodies against integrins αvβ5 αvβ3, αv, αvβ6, αvβ8 and 133 as well as Vitronectin, Osteopontin, Ki67 and CD31. All anti-integrin antibodies and the related staining protocols were provided by Merck Serono. The protocols were further adjusted to the staining instruments in the lab of Indivumed. Immunohistochemistry protocols to detect Vitronectin, Osteopontin, Ki67 and CD31 were previously established at Indivumed and approved by Merck Serono. As quality control, IHC of cell lines and tissue were performed in each run (run controls). Furthermore, isotype controls were prepared for every run control.

For IHC staining, FFPE tissues were provided by Merck Serono/Covance. FFPE positive control samples (cells lines or tissues), which were used as run controls and isotype control, were sliced into 3 μm sections and mounted on positively charged Super Frost® Ultra Plus glass slides (Roth, Karlsruhe). IHC was implemented on Discovery® XT staining instruments (Roche/Ventana Medical Systems Inc.). FFPE slides were deparaffinized within the staining instrument and immunostained using the ChromoMap 4.2. Automatic Procedure/Protocol
Program steps (DiscoveryXT):
  Procedure: Res IHC Omni-UltraMap HRP XT (Protocol Summary)
  Discovery XT Staining Module
  Indivumed, Falkenried 88, 20251 Hamburg
  Protocol No 307
  Protocol Name: A-avb6 (107)
  Creation Date: 10 May 2013
    1 Tissue Sample [Selected]
    2 Paraffin [Selected]
    3 Deparaffinization [Selected]
    4 Enzyme [Selected]
    5 Apply One Drop of [PROTEASE 2] (Enzyme) Apply Coverslip, and Incubate for [12 minutes]
    6 Antibody [Selected]
    7 Antibody Auto Dispense [Selected]
    7 Standard Ab incubation (Selected)
    8 Apply One Drop of [ANTIBODY 23] (Antibody), and Incubate for [32 minutes]
    9 Apply One Drop of [OMap anti-Rb HRP] (Multimer HRP), Apply Coverslip, and
    10 Incubate for [16 Minutes]
    11 Counterstain [Selected]
    12 Standard [Selected]
    13 Apply Ore Drop of [HEMATOXYLIN II] (Counterstain), Apply Coverslip, and Incubate for [8 Minutes]

14 Post Counterstain [Selected]
15 Apply One Drop of [BLUING REAGENT] (Post Counterstain), Apply Coverslip, and incubate for [4 minutes]
16 Slide Cleaning [Selected]

4.2. Histopathological Evaluation

Immunohistochemically stained FFPE samples were evaluated by the pathologist of Indivumed. In general, the pathologist quantifies the predominant staining intensity, specifies the staining pattern and estimates the percentages of positively stained tumor tissue. The tumor content as well as the tissue type was determined using H&E stained sections. Scoring systems for the semi-quantitative evaluation are described below. Furthermore, immunohistochemically stained subcellular compartments were defined. Therefore, the pathologist distinguished between membranes (m), nuclei (n) and cytoplasm (c). As required, a more detailed description of the staining pattern was mentioned in the comment. To analyze the proliferative rate of tumor tissue anti-Ki67 IHC was performed. The pathologist determined the percentage of Ki67-positive tumor cells by the evaluation of 100 tumor cells.

4.2.1 Histoscore (H-Score): Evaluation of Tumor Cells

For the semi-quantitative evaluation of immunohistochemically stained tumor tissue a H-score classification was applied as described in: McCarty Jr K S, Miller L S, Cox E B, Konrath J, McCarty Sr K S "Estrogen receptor analyses: Correlation of biochemical and immunohistochemical methods using monoclonal antireceptor antibodies". Arch Pathol Lab Med 109: 716-721 (1985) the disclosure of which is preferably incorporated herein by reference in its entirety. Therefore, negative (0), weakly stained (1), moderately stained (2) and strongly stained (3) areas were estimated as percentage of tumor tissue. Subsequently the H-score was calculated as follows.

$$H\text{-score}=(\text{weak})\%+(\text{moderate})\%\times 2+(\text{strong})\%\times 3$$

TABLE 26

| Histoscores | |
|---|---|
| H-score | Classification |
| 0-50 | negative |
| 51-100 | weak positive |
| 101-200 | moderate positive |
| 201-300 | strong positive |

An accordingly obtained histoscore of higher than 70 (>70) was preferably deemed a suitable threshold for fulfilling the criterion of "high αvβ6 integrin expression" in the context of Abituzumab treatment.

The invention claimed is:

1. A method of treating colorectal cancer in a human, said method comprising:
   selecting a human having left-sided colorectal cancer with an αvβ6 integrin expression corresponding to a histoscore of 51 to 300; and
   administering Abituzumab to said selected human.

2. The method according to claim 1, wherein said human also receives at least one growth factor or growth factor receptor targeting monoclonal antibody, and/or chemotherapy.

3. The method according to claim 1, wherein said left-sided colorectal cancer is stage II, stage III or stage IV left-sided colorectal cancer.

4. The method according to claim 1, wherein said left-sided colorectal cancer is left-sided metastatic colorectal cancer.

5. The method according to claim 1, wherein said left-sided colorectal cancer is RAS wild-type and/or KRAS wild-type left-sided colorectal cancer.

6. The method according to claim 1, wherein said left-sided colorectal cancer is RAS wild-type and/or KRAS wild-type left-sided colorectal cancer or RAS wild-type and/or KRAS wild-type left-sided metastatic colorectal cancer.

7. The method according to claim 1, wherein said left-sided colorectal cancer is stage II, stage III or stage IV RAS wild-type and/or KRAS wild-type left-sided colorectal cancer or RAS wild-type and/or KRAS wild-type left-sided metastatic colorectal cancer.

8. The method according to claim 1, wherein said left-sided colorectal cancer is RAS wild-type and/or KRAS wild-type left-sided metastatic colorectal cancer.

9. The method according to claim 1, wherein said left-sided colorectal cancer is newly diagnosed colorectal cancer.

10. The method according to claim 1, wherein said method is applied in at least one treatment setting selected from the group consisting of a first-line treatment setting, a concomitant treatment setting, an adjuvant treatment setting, and a neoadjuvant treatment setting.

11. The method according to claim 2, wherein said human receives said at least one growth factor or growth factor receptor targeting monoclonal antibody and/or said chemotherapy concomitantly to said Abituzumab.

12. The method according to claim 2, wherein said human receives said at least one growth factor or growth factor receptor targeting monoclonal antibody, which is selected from the group consisting of Cetuximab, Bevacizumab and Panitumumab.

13. The method according to claim 2, wherein said human receives said at least one growth factor or growth factor receptor targeting monoclonal antibody, which is selected from the group consisting of Cetuximab and Bevacizumab.

14. The method according to claim 2, wherein said human receives said chemotherapy, which comprises one or more compounds selected from the group consisting of irinotecan, fluorouracil (5-FU), tegafur/uracil (UFT), folinic acid, Oxaliplatin, aflibercept, regorafenib, capecitabine, and the prodrugs thereof, and the salts and solvates thereof.

15. The method according to claim 2, wherein said chemotherapy is administered according to a FOLFIRI protocol or FOLFOX protocol.

16. The method according to claim 2, wherein said human receives said chemotherapy, which comprises:
   a) one or more compounds selected from the group consisting of irinotecan, fluorouracil (5-FU), and folinic acid (leucovorin), and the prodrugs thereof, or
   b) one or more compounds selected from the group consisting of oxaliplatin, fluorouracil (5-FU), and folinic acid (leucovorin), and the prodrugs thereof, and the salts and solvates thereof.

17. The method according to claim 1, wherein said Abituzumab is administered to said human in an amount of 375 mg to 750 mg per week, in an amount of 750 mg to 1500 mg every second week or in an amount of 1500 mg to 3000 mg per month.

18. The method according to claim 17, wherein said Abituzumab is administered to said human in an amount of about 500 mg per week, in an amount of about 1000 mg every second week or in an amount of about 2000 mg per month.

19. The method according to claim 1, wherein said Abituzumab is administered to said human for at least 6 cycles, each cycle having a duration of about 1 week, of about 2 weeks, of about 4 weeks or of about a month.

20. The method according to claim 19, wherein said Abituzumab is administered to said human for at least 6 cycles, each cycle having a duration of about 2 weeks.

21. The method according to claim 2, wherein said at least one growth factor or growth factor receptor targeting monoclonal antibody is administered to said human in an amount of 75 mg to 1000 mg per week, 150 mg to 2000 mg every second week, or in an amount of 300 mg to 4000 mg per month.

22. The method according to claim 12, wherein said Cetuximab is administered to said human in an amount of about 150 mg/m$^2$ to 550 mg/m$^2$ per week, 300 mg/m$^2$ to 1100 mg/m$^2$ every second week, or in an amount of about 600 mg/m$^2$ to per 2200 mg/m$^2$ per month.

23. The method according to claim 12, wherein the at least one growth factor or growth factor receptor targeting monoclonal antibody is administered to said human for at least 6 cycles, each cycle having a duration of about 1 week, of about 2 weeks, of about 4 weeks, or of about a month.

24. The method according to claim 23, wherein the at least one growth factor or growth factor receptor targeting monoclonal antibody is administered to said human for at least 6 cycles, each cycle having a duration of about 2 weeks, wherein said at least one growth factor or growth factor receptor targeting monoclonal antibody is administered to said human every week or every second week.

25. The method according to claim 12, wherein said at least one growth factor or growth factor receptor targeting monoclonal antibody is Cetuximab,
wherein said Cetuximab is administered to said human for at least 6 cycles, each cycle having a duration of about 2 weeks,
wherein said Cetuximab is administered to said human either:
a) in an amount of about 500 mg/m$^2$ during each cycle, or
b) in an amount of about 400 mg/m$^2$ at the beginning of the first week of each cycle and in an amount of about 250 mg/m$^2$ at the beginning of the second week of each cycle.

26. The method according to claim 12, wherein said Bevacizumab is administered to said human in an amount of about 1 mg/kg to 10 mg/kg per week, 3 mg/kg to 15 mg/kg every second week, or in an amount of about 6 mg/kg to per 30 mg/kg per month.

27. The method according to claim 12, wherein said Bevacizumab is administered to said human for at least 6 cycles, each cycle having a duration of about 2 weeks, wherein said Bevacizumab is administered to said human either
a) in an amount of 3 mg/kg to 15 mg/kg or in an amount of 5 mg/kg to 10 mg/kg during each cycle, or
b) in an amount of about 7.5 mg/kg during each cycle.

28. The method according to claim 12, wherein said Panitumumab is administered to said human in an amount of about 1 mg/kg to 10 mg/kg per week, 3 mg/kg to 15 mg/kg every second week, or in an amount of about 6 mg/kg to per 30 mg/kg per month.

29. The method according to claim 12, wherein said Panitumumab is administered to said human for at least 6 cycles, each cycle having a duration of about 2 weeks, wherein said Panitumumab is administered to said human either
a) in an amount of 3 mg/kg to 15 mg/kg or in an amount of 4 mg/kg to 10 mg/kg during each cycle, and preferably at the beginning of each cycle, or
b) in an amount of about 6 mg/kg during each cycle, and preferably at the beginning of each cycle.

30. The method according to claim 12, wherein said colorectal cancer is RAS wild-type and/or KRAS wild-type colorectal cancer.

31. The method according to claim 12, wherein said left-sided colorectal cancer is RAS wild-type and/or KRAS wild-type left-sided colorectal cancer or RAS wild-type and/or KRAS wild-type left-sided metastatic colorectal cancer.

32. The method according to claim 2, wherein said chemotherapy is administered to said human for at least 6 cycles, each cycle having a duration of about 2 weeks, wherein
a) irinotecan, and/or a prodrug, a salt and/or a solvate thereof,
b) folinic acid, and/or a prodrug, a salt and/or a solvate thereof, and/or
c) fluorouracil (5-FU), and/or a prodrug, a salt and/or a solvate thereof, is administered to said human during each cycle.

33. The method according to claim 32, wherein said chemotherapy comprises:
a) irinotecan, and/or a prodrug, a salt and/or a solvate thereof, in an amount of 50 mg/m$^2$ to 150 mg/m$^2$ per week, in an amount of 100 mg/m$^2$ to 300 mg/m$^2$ every second week, or in an amount of 200 mg/m$^2$ to 600 mg/m$^2$ per month,
b) folinic acid, and/or a prodrug, a salt and/or a solvate thereof, in an amount of 150 mg/m$^2$ to 250 mg/m$^2$ per week, in an amount of 300 mg/m$^2$ to 500 mg/m$^2$ every second week, or in an amount of 600 mg/m$^2$ to 1000 mg/m$^2$ per month, and/or
c) fluorouracil (5-FU), and/or a prodrug, a salt and/or a solvate thereof, in an amount of 150 mg/m$^2$ to 250 mg/m$^2$ per week, in an amount of 300 mg/m$^2$ to 500 mg/m$^2$ every second week, or in an amount of 600 mg/m$^2$ to 1000 mg/m$^2$ per month.

34. The method according to claim 32, wherein said chemotherapy comprises:
a) irinotecan, and/or a prodrug, a salt and/or a solvate thereof, in an amount of 50 mg/m$^2$ to 150 mg/m$^2$ per week, in an amount of 100 mg/m$^2$ to 300 mg/m$^2$ every second week, or in an amount of 200 mg/m$^2$ to 600 mg/m$^2$ per month,
b) folinic acid, and/or a prodrug, a salt and/or a solvate thereof, in an amount of 150 mg/m$^2$ to 250 mg/m$^2$ per week, in an amount of 300 mg/m$^2$ to 500 mg/m$^2$ every second week, or in an amount of 600 mg/m$^2$ to 1000 mg/m$^2$ per month, and/or
c) fluorouracil (5-FU), and/or a prodrug, a salt and/or a solvate thereof, in an amount of 1000 mg/m$^2$ to 3000 mg/m$^2$ per week, in an amount of 2000 mg/m$^2$ to 6000 mg/m$^2$ every second week, or in an amount of 4000 mg/m$^2$ to 12000 mg/m$^2$ per month.

35. The method according to claim 2, wherein said chemotherapy is administered to said human for at least 6 cycles, each cycle having a duration of about 1 week, of about 2 weeks, of about 4 weeks, or of about a month.

36. The method according to claim 14, wherein said chemotherapy is administered to said human for at least 6 cycles, each cycle having a duration of about 2 weeks, wherein
a) said oxaliplatin, and/or a prodrug, a salt and/or a solvate thereof,
b) said folinic acid, and/or a prodrug, a salt and/or a solvate thereof, and/or
c) said fluorouracil (5-FU), and/or a prodrug, a salt and/or a solvate thereof, is administered to said human during each cycle.

37. The method according to claim 36, wherein said chemotherapy comprises:
a) oxaliplatin, and/or a prodrug, a salt and/or a solvate thereof, in an amount of 20 mg/m$^2$ to 120 mg/m$^2$ per week, in an amount of 40 mg/m² to 240 mg/m² every second week, or in an amount of 80 mg/m² to 480 mg/m² per month,
b) folinic acid, and/or a prodrug, a salt and/or a solvate thereof, in an amount of 150 mg/m² to 250 mg/m² per week, in an amount of 300 mg/m² to 500 mg/m² every second week, or in an amount of 600 mg/m² to 1000 mg/m² per month, and/or
c) 5-FU, and/or a prodrug, a salt and/or a solvate thereof, in an amount of 150 mg/m² to 250 mg/m² per week, in an amount of 300 mg/m² to 500 mg/m² every second week, or in an amount of 600 mg/m² to 1000 mg/m² per month.

38. The method according to claim 36, wherein said chemotherapy comprises:
a) oxaliplatin, and/or a prodrug, a salt and/or a solvate thereof, in an amount of 20 mg/m² to 120 mg/m² per week, in an amount of 40 mg/m² to 240 mg/m² every second week, or in an amount of 80 mg/m² to 480 mg/m² per month,
b) folinic acid, and/or a prodrug, a salt and/or a solvate thereof, in an amount of 150 mg/m² to 250 mg/m² per week, in an amount of 300 mg/m² to 500 mg/m² every second week, or in an amount of 600 mg/m² to 1000 mg/m² per month, and/or
c) 5-FU, and/or a prodrug, a salt and/or a solvate thereof, in an amount of 1000 mg/m² to 3000 mg/m² per week, in an amount of 2000 mg/m² to 6000 mg/m² every second week, or in an amount of 4000 mg/m² to 12000 mg/m² per month.

39. The method according to claim 1, wherein a primary tumor is located in the left-side of the colon.

* * * * *

SEQUENCE LISTING

```
<160> NUMBER OF SEQ ID NOS: 7

<210> SEQ ID NO 1
<211> LENGTH: 214
<212> TYPE: PRT
<213> ORGANISM: Artificial Sequence
<220> FEATURE:
<223> OTHER INFORMATION: Abituzumab variable and constant light chain
      sequences

<400> SEQUENCE: 1

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Tyr Tyr Thr Ser Lys Ile His Ser Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Gly Asn Thr Phe Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 447
<212> TYPE: PRT
<213> ORGANISM: Artificial Sequence
<220> FEATURE:
<223> OTHER INFORMATION: Abituzumab variable and constant heavy chain
      sequences

<400> SEQUENCE: 2

Gln Val Gln Leu Gln Gln Ser Gly Gly Glu Leu Ala Lys Pro Gly Ala
1               5                   10                  15

Ser Val Lys Val Ser Cys Lys Ala Ser Gly Tyr Thr Phe Ser Ser Phe
            20                  25                  30

Trp Met His Trp Val Arg Gln Ala Pro Gly Gln Gly Leu Glu Trp Ile
        35                  40                  45

Gly Tyr Ile Asn Pro Arg Ser Gly Tyr Thr Glu Tyr Asn Glu Ile Phe
    50                  55                  60

Arg Asp Lys Ala Thr Met Thr Thr Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Phe Leu Gly Arg Gly Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Pro Lys Ser Ser Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Ala Gln Ser Thr Phe Arg Val Val Ser
    290                 295                 300

Val Leu Thr Val Val His Gln Asp Trp Leu Asn Gly Lys Glu Tyr Lys
305                 310                 315                 320
```

```
Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 3
<211> LENGTH: 15
<212> TYPE: PRT
<213> ORGANISM: Artificial Sequence
<220> FEATURE:
<223> OTHER INFORMATION: Abituzumab modified IgG1 hinge region

<400> SEQUENCE: 3

Glu Pro Lys Ser Ser Asp Lys Thr His Thr Cys Pro Pro Cys Pro
1               5                   10                  15

<210> SEQ ID NO 4
<211> LENGTH: 30
<212> TYPE: PRT
<213> ORGANISM: Artificial Sequence
<220> FEATURE:
<223> OTHER INFORMATION: Abituzumab variant FR1 comprising modifications
      within the heavy chain framework region

<400> SEQUENCE: 4

Gln Val Gln Leu Gln Gln Ser Gly Ala Glu Leu Ala Glu Pro Gly Ala
1               5                   10                  15

Ser Val Lys Met Ser Cys Lys Ala Ser Gly Tyr Thr Phe Ser
            20                  25                  30

<210> SEQ ID NO 5
<211> LENGTH: 14
<212> TYPE: PRT
<213> ORGANISM: Artificial Sequence
<220> FEATURE:
<223> OTHER INFORMATION: Abituzumab variant FR2 comprising modifications
      within the heavy chain framework region

<400> SEQUENCE: 5

Trp Val Lys Gln Arg Pro Gly Gln Gly Leu Glu Trp Ile Gly
1               5                   10

<210> SEQ ID NO 6
<211> LENGTH: 32
<212> TYPE: PRT
<213> ORGANISM: Artificial Sequence
<220> FEATURE:
<223> OTHER INFORMATION: Abituzumab variant FR3 comprising modifications
      within the heavy chain framework region

<400> SEQUENCE: 6
```

```
Lys Ala Thr Met Thr Ala Asp Thr Ser Ser Ser Thr Ala Tyr Met Gln
1               5                   10                  15

Leu Ser Gly Leu Thr Ser Glu Asp Ser Ala Val Tyr Tyr Cys Ala Ser
            20                  25                  30

<210> SEQ ID NO 7
<211> LENGTH: 11
<212> TYPE: PRT
<213> ORGANISM: Artificial Sequence
<220> FEATURE:
<223> OTHER INFORMATION: Abituzumab variant FR4 comprising a
      modification within the heavy chain framework region

<400> SEQUENCE: 7

Trp Gly Gln Gly Thr Ser Val Thr Val Ser Ser
1               5                   10
```